(12) United States Patent
Kim et al.

(10) Patent No.: US 11,046,975 B2
(45) Date of Patent: Jun. 29, 2021

(54) BICISTRONIC EXPRESSION VECTOR FOR ANTIBODY EXPRESSION AND METHOD FOR PRODUCING ANTIBODY USING SAME

(71) Applicant: Prestige Biopharma Pte. Ltd., Singapore (SG)

(72) Inventors: Soo Kwang Kim, Daejeon (KR); Young Min Kim, Gyeonggi-do (KR); Yong Gyu Son, Gyeongsangnam-do (KR); Yong Ho Ahn, Daejeon (KR); Dong Heon Lee, Daejeon (KR); Yang Soon Lee, Daejeon (KR); Hee Jung Jun, Daejeon (KR); Yu Bin Choi, Daejeon (KR); Eun A Kim, Incheon (KR)

(73) Assignee: PRESTIGE BIOPHARMA PTE. LTD., Singapore (SG)

( * ) Notice: Subject to any disclaimer, the term of this patent is extended or adjusted under 35 U.S.C. 154(b) by 0 days.

(21) Appl. No.: 15/027,929

(22) PCT Filed: Oct. 7, 2014

(86) PCT No.: PCT/KR2014/009398
§ 371 (c)(1),
(2) Date: Apr. 7, 2016

(87) PCT Pub. No.: WO2015/053523
PCT Pub. Date: Apr. 16, 2015

(65) Prior Publication Data
US 2016/0281106 A1 Sep. 29, 2016

(30) Foreign Application Priority Data

Oct. 7, 2013 (KR) .................. 10-2013-0119511
Feb. 20, 2014 (KR) .................. 10-2014-0019780
Feb. 20, 2014 (KR) .................. 10-2014-0019781
Feb. 20, 2014 (KR) .................. 10-2014-0019782
Jul. 9, 2014 (KR) .................. 10-2014-0085932
Jul. 9, 2014 (KR) .................. 10-2014-0085933
Jul. 9, 2014 (KR) .................. 10-2014-0085934

(51) Int. Cl.
*C12N 15/85* (2006.01)
*C07K 16/24* (2006.01)
*C07K 16/00* (2006.01)
*C07K 1/14* (2006.01)
*C07K 16/18* (2006.01)
*C07K 16/22* (2006.01)
*C07K 16/28* (2006.01)

(52) U.S. Cl.
CPC .............. *C12N 15/85* (2013.01); *C07K 1/14* (2013.01); *C07K 16/00* (2013.01); *C07K 16/18* (2013.01); *C07K 16/22* (2013.01); *C07K 16/24* (2013.01); *C07K 16/241* (2013.01); *C07K 16/244* (2013.01); *C07K 16/2818* (2013.01); *C07K 16/2866* (2013.01); *C12N 2510/02* (2013.01); *C12N 2840/203* (2013.01)

(58) Field of Classification Search
CPC ........ C07K 16/00; C07K 16/18; C07K 16/22; C07K 16/24; C07K 16/241; C07K 16/244; C07K 16/2818; C07K 16/2866; C07K 1/14; C12N 15/85; C12N 2510/02; C12N 2840/203
See application file for complete search history.

(56) References Cited

U.S. PATENT DOCUMENTS

| | | | |
|---|---|---|---|
| 6,479,258 B1 * | 11/2002 | Short | C07K 14/445 435/69.1 |
| 2005/0191723 A1 * | 9/2005 | Otte | C07K 16/00 435/69.1 |
| 2006/0195935 A1 * | 8/2006 | Otte | C12N 15/67 800/278 |

(Continued)

FOREIGN PATENT DOCUMENTS

| CN | 101163792 A | 4/2008 |
|---|---|---|
| CN | 101906435 A | 12/2010 |

(Continued)

OTHER PUBLICATIONS

Cacciatore et al., "Gene amplification and vector engineering to achieve rapid and high-level therapeutic protein production using the Dhfr-based CHO cell selection system" 28 Biotechnology Advances 673-681 (Year: 2010).*

Zhu et al., "Mammalian cell protein expression for biopharmaceutical production" 30 Biotechnology Advances 1158-1170 (Year: 2011).*

Fallot, S. et al., "Alternative-splicing-based bicistronic vectors for ratio-controlled protein expression and application to recombinant antibody production", Nucleic Acids Research, 2009, vol. 37, No. 20.

(Continued)

*Primary Examiner* — Nancy J Leith
(74) *Attorney, Agent, or Firm* — Umberg Zipser LLP

(57) ABSTRACT

The present invention relates to a bicistronic expression vector for antibody expression, an animal cell transfected with the expression vector, and a method for producing an antibody including culturing the animal cell, in which the expression vector includes a first expression cassette including 'promoter-UTR-intron-antibody light chain gene-polyA' and a second expression cassette including 'promoter-UTR-intron-antibody heavy chain gene-internal ribosome entry site (IRES)-amplification gene-polyA'. An expression vector capable of expressing a desired antibody with high efficiency can be constructed using the bicistronic expression vector including an intron for antibody expression according to the present invention, and the expression vector can produce the antibody by culturing the transfected animal cell with stability and high efficiency.

10 Claims, 13 Drawing Sheets
Specification includes a Sequence Listing.

(56) References Cited

U.S. PATENT DOCUMENTS

| | | | |
|---|---|---|---|
| 2006/0263882 A1 | 11/2006 | Fazio et al. | |
| 2007/0111260 A1* | 5/2007 | Gao | C07K 16/00 435/7.1 |
| 2009/0181424 A1* | 7/2009 | Albericio | C12N 15/85 435/69.1 |
| 2010/0144599 A1* | 6/2010 | Mendlein | A61K 38/39 514/1.1 |
| 2012/0301919 A1* | 11/2012 | Yang | C12P 21/02 435/69.6 |
| 2013/0039920 A1* | 2/2013 | Li | C07K 16/2863 424/141.1 |
| 2016/0194660 A1* | 7/2016 | Ye | C12N 15/85 435/69.6 |

FOREIGN PATENT DOCUMENTS

| | | |
|---|---|---|
| CN | 102392047 | 3/2012 |
| CN | 1023920447 A | 3/2012 |
| JP | 20090535065 | 10/2009 |
| JP | 20120500634 | 1/2012 |
| JP | 2013526829 | 6/2013 |
| KR | 20030062118 | 7/2003 |
| KR | 20030062118 A | 7/2003 |
| KR | 20120093903 | 8/2012 |
| WO | 2006111387 A2 | 10/2006 |
| WO | 2007130543 A2 | 11/2007 |
| WO | 2012018607 A2 | 2/2012 |
| WO | 2013092743 | 6/2013 |
| WO | 2013/180473 A1 | 12/2013 |

OTHER PUBLICATIONS

Robert Young, Important Topics in the Expression of Recombinant Antibodies from CHO Cells, Cell Line Development and Engineering Workshop, Lonza, Mar. 2008.

Steven Ho, IRES-Mediated Tricistronic Vectors for Enhancing Generation of High Monoclonal Antibody Expressing CHO Cell Lines, Journal of Biotechnology 157, (2012) 130-139.

Thomas Jostock, Expression of Antibody in Mammalian Cells, Novartis Pharma AG, CH-4002 Basel, Switzerland.

Ludwig, Dale L., "Mammalian Expression Cassette Engineering for High-Level Protein Production," BioProcess International, May 2006; 4(3):14-23.

Genbank No. X03922.1.

Peuscher, Anne Verena, "High level recombinant antibody production in Chinese hamster ovary (CHO) cells and characterisation of the carcinoembryonic antigen (CEA) specific human full-size IgG1 H10," PhD Thesis, Apr. 8, 2011; pp. 1-171. Retrieved from the Internet:URL:https://core.ac.uk/download/pdf/36430701.pdf [retrieved on Mar. 21, 2019].

Summons to Attend Oral Proceedings pursuant to Rule 115(1) EPC for European Appl. No. 14851589.3-1116 / 3059319 dated Apr. 16, 2019; 6 pgs.

Barrett et al., "Regulation of eukaryotic gene expression by the untranslated gene regions and other non-coding elements," Cell. Mol. Life Sci., 2012; 69:3613-3634.

Notice of Appeal issued for European Patent Application No. 14851589.3 dated Feb. 7, 2020; 12 pgs.

* cited by examiner

```
                              SEQUENCE LISTING

<160> NUMBER OF SEQ ID NOS: 39

<210> SEQ ID NO 1
<211> LENGTH: 1143
<212> TYPE: DNA
<213> ORGANISM: Unknown
<220> FEATURE:
<223> OTHER INFORMATION: Cytomegalovirus stain AD169 promoter

<400> SEQUENCE: 1
ctgcagtgaa taataaaatg tgtgtttgtc cgaaatacgc gttttgagat ttctgtcgcc      60
gactaaattc atgtcgcgcg atagtggtgt ttatcgccga tagagatggc gatattggaa     120
aaatcgatat ttgaaaatat ggcatattga aaatgtcgcc gatgtgagtt tctgtgtaac     180
tgatatcgcc attttccaa aagtgatttt tgggcatacg cgatatctgg cgatagcgct      240
tatatcgttt acggggatg gcgatagacg actttggtga cttgggcgat tctgtgtgtc      300
gcaaatatcg cagtttcgat ataggtgaca gacgatatga ggctatatcg ccgatagagg     360
cgacatcaag ctggcacatg gccaatgcat atcgatctat acattgaatc aatattggcc     420
attagccata ttattcattg gttatatagc ataaatcaat attggctatt ggccattgca    480
tacgttgtat ccatatcata atatgtacat ttatattggc tcatgtccaa cattaccgcc    540
atgttgacat tgattattga ctagttatta atagtaatca attacggggt cattagttca    600
tagcccatat atggagttcc gcgttacata acttacggta aatggcccgc ctggctgacc    660
gcccaacgac ccccgcccat tgacgtcaat aatgacgtat gttcccatag taacgccaat    720
agggactttc cattgacgtc aatgggtgga gtatttacgg taaactgccc acttggcagt    780
acatcaagtg tatcatatgc caagtacgcc ccctattgac gtcaatgacg gtaaatggcc    840
cgcctggcat tatgcccagt acatgacctt atgggacttt cctacttggc agtacatcta    900
cgtattagtc atcgctatta ccatggtgat gcggttttgg cagtacatca atgggcgtgg    960
atagcggttt gactcacggg gatttccaag tctccacccc attgacgtca atgggagttt   1020
gttttggcac caaaatcaac gggactttcc aaaatgtcgt aacaactccg ccccattgac   1080
gcaaatgggc ggtaggcgtg tacggtggga ggtctatata agcagagctc gtttagtgaa   1140
ccg                                                                  1143

<210> SEQ ID NO 2
<211> LENGTH: 121
<212> TYPE: DNA
<213> ORGANISM: Unknown
<220> FEATURE:
<223> OTHER INFORMATION: Cytomegalovirus stain AD169 UTR(5'UTR)

<400> SEQUENCE: 2
tcagatcgcc tggagacgcc atccacgctg ttttgacctc catagaagac accgggaccg      60
atccagcctc cgcggccggg aacggtgcat tggaacgcgg attccccgtg ccaagagtga     120
```

```
c                                                                  121

<210> SEQ ID NO 3
<211> LENGTH: 827
<212> TYPE: DNA
<213> ORGANISM: Unknown
<220> FEATURE:
<223> OTHER INFORMATION: Cytomegalovirus stain AD169 intron

<400> SEQUENCE: 3
gtaagtaccg cctatagagt ctataggccc acccccttgg cttcttatgc atgctatact    60
gtttttggct tggggtctat acaccccgc ttcctcatgt tataggtgat ggtatagctt   120
agcctatagg tgtgggttat tgaccattat tgaccactcc cctattggtg acgatacttt   180
ccattactaa tccataacat ggctctttgc cacaactctc tttattggct atatgccaat   240
acactgtcct tcagagactg acacggactc tgtatttta caggatgggg tctcatttat   300
tatttacaaa ttcacatata caacaccacc gtccccagtg cccgcagttt ttattaaaca   360
taacgtggga tctccacgcg aatctcgggt acgtgttccg gacatgggct cttctccggt   420
agcggcggag cttctacatc cgagccctgc tcccatgcct ccagcgactc atggtcgctc   480
ggcagctcct tgctcctaac agtggaggcc agacttaggc acagcacgat gcccaccacc   540
accagtgtgc cgcacaaggc cgtggcggta gggtatgtgt ctgaaaatga gctcggggag   600
cgggcttgca ccgctgacgc atttggaaga cttaaggcag cggcagaaga agatgcaggc   660
agctgagttg ttgtgttctg ataagagtca gaggtaactc ccgttgcggt gctgttaacg   720
gtggagggca gtgtagtctg agcagtactc gttgctgccg cgcgcgccac cagacataat   780
agctgacaga ctaacagact gttcctttcc atgggtcttt tctgcag                 827

<210> SEQ ID NO 4
<211> LENGTH: 576
<212> TYPE: DNA
<213> ORGANISM: Unknown
<220> FEATURE:
<223> OTHER INFORMATION: IRES (internal ribosome entry site)

<400> SEQUENCE: 4
cgcccctctc cctccccccc ccctaacgtt actggccgaa gccgcttgga ataaggccgg    60
tgtgcgtttg tctatatgtt attttccacc atattgccgt cttttggcaa tgtgagggcc   120
cggaaacctg gccctgtctt cttgacgagc attcctaggg gtctttcccc tctcgccaaa   180
ggaatgcaag gtctgttgaa tgtcgtgaag gaagcagttc ctctggaagc ttcttgaaga   240
caaacaacgt ctgtagcgac cctttgcagg cagcggaacc ccccacctgg cgacaggtgc   300
ctctgcggcc aaaagccacg tgtataagat acacctgcaa aggcggcaca accccagtgc   360
cacgttgtga gttggatagt tgtggaaaga gtcaaatggc tctcctcaag cgtattcaac   420
aaggggctga aggatgccca gaaggtaccc cattgtatgg gatctgatct ggggcctcgg   480
tgcacatgct ttcatgtgt ttagtcgagg ttaaaaaaac gtctaggccc cccgaaccac   540
ggggacgtgg ttttcctttg aaaaacacga tgataa                            576

<210> SEQ ID NO 5
<211> LENGTH: 2399
<212> TYPE: DNA
<213> ORGANISM: Unknown
<220> FEATURE:
<223> OTHER INFORMATION: Gln-LC

<400> SEQUENCE: 5
```

```
cctaggcgcg cctgcagtga ataataaaat gtgtgtttgt ccgaaatacg cgttttgaga      60
tttctgtcgc cgactaaatt catgtcgcgc gatagtggtg tttatcgccg atagagatgg     120
cgatattgga aaaatcgata tttgaaaata tggcatattg aaaatgtcgc cgatgtgagt     180
ttctgtgtaa ctgatatcgc cattttccaa aaagtgattt ttgggcatac gcgatatctg     240
gcgatagcgc ttatatcgtt tacgggggat ggcgatagac gactttggtg acttgggcga     300
ttctgtgtgt cgcaaaatcg cagtttcga tataggtgac agacgatatg aggctatatc      360
gccgatagag gcgacatcaa gctggcacat ggccaatgca tatcgatcta tacattgaat     420
caatattggc cattagccat attattcatt ggttatatag cataaatcaa tattggctat     480
tggccattgc atacgttgta tccatatcat aatatgtaca tttatattgg ctcatgtcca     540
acattaccgc catgttgaca ttgattattg actagttatt aatagtaatc aattacgggg     600
tcattagttc atagcccata tatggagttc gcgttacat  aacttacggt aaatggcccg     660
cctggctgac cgcccaacga cccccgccca ttgacgtcaa taatgacgta tgttcccata     720
gtaacgccaa tagggacttt ccattgacgt caatgggtgg agtatttacg gtaaactgcc     780
cacttggcag tacatcaagt gtatcatatg ccaagtacgc cccctattga cgtcaatgac     840
ggtaaatggc ccgcctggca ttatgcccag tacatgacct tatgggactt tcctacttgg     900
cagtacatct acgtattagt catcgctatt accatggtga tgcggttttg gcagtacatc     960
aatgggcgtg gatagcggtt tgactcacgg ggatttccaa gtctccaccc cattgacgtc    1020
aatgggagtt tgttttggca ccaaaatcaa cgggactttc caaaatgtcg taacaactcc    1080
gccccattga cgcaaatggg cggtaggcgt gtacggtggg aggtctatat aagcagagct    1140
cgtttagtga accgtcagat cgcctggaga cgccatccac gctgttttga cctccataga    1200
agacaccggg accgatccag cctccgcggc cgggaacggt gcattggaac gcggattccc    1260
cgtgccaaga gtgacgtaag taccgcctat agagtctata ggcccacccc cttggcttct    1320
tatgcatgct atactgtttt tggcttgggg tctatacacc cccgcttcct catgttatag    1380
gtgatggtat agcttagcct ataggtgtgg gttattgacc attattgacc actcccctat    1440
tggtgacgat actttccatt actaatccat aacatggctc tttgccacaa ctctctttat    1500
tggctatatg ccaatacact gtccttcaga gactgacacg gactctgtat ttttacagga    1560
tggggtctca tttattattt acaaattcac atatacaaca ccaccgtccc cagtgccgc     1620 agttttatt aaacataacg tgggatctcc acgcgaatct cgggtacgtg ttccggacat     1680
gggctcttct ccggtagcgg cggagcttct acatccgagc cctgctccca tgcctccagc    1740
gactcatggt cgctcggcag ctccttgctc ctaacagtgg aggccagact taggcacagc    1800
acgatgccca ccaccaccag tgtgccgcac aaggccgtgg cggtagggta tgtgtctgaa    1860
aatgagctcg gggagcgggc ttgcaccgct gacgcatttg gaagacttaa ggcagcggca    1920
gaagaagatg caggcagctg agttgttgtg ttctgataag agtcagaggt aactcccgtt    1980
gcggtgctgt taacggtgga gggcagtgta gtctgagcag tactcgttgc tgccgcgcgc    2040
gccaccagac ataatagctg acagactaac agactgttcc tttccatggg tcttttctgc    2100
agtcaccgtc cttgacacgt ctagaccaga tctttgcggc cgcattgatc ataatcagcc    2160
ataccacatt tgtagaggtt ttacttgctt taaaaaacct cccacacctc ccctgaacc    2220 tgaaacataa aatgaatgca attgttgttg ttaacttgtt tattgcagct tataatggtt    2280
acaaataaag caatagcatc acaaatttca caaataaagc attttttca  ctgcattcta    2340
```

```
gttgtggttt gtccaaactc atcaatgtat cttatcatgt ctggatccgc tagctcgag      2399
```

<210> SEQ ID NO 6
<211> LENGTH: 2125
<212> TYPE: DNA
<213> ORGANISM: Unknown
<220> FEATURE:
<223> OTHER INFORMATION: Gln-HC

<400> SEQUENCE: 6

```
cctaggcgcg cctgcagtga ataataaaat gtgtgtttgt ccgaaatacg cgttttgaga       60
tttctgtcgc cgactaaatt catgtcgcgc gatagtggtg tttatcgccg atagagatgg      120
cgatattgga aaatcgata tttgaaaata tggcatattg aaaatgtcgc cgatgtgagt      180
ttctgtgtaa ctgatatcgc catttttcca aaagtgattt ttgggcatac gcgatatctg      240
gcgatagcgc ttatatcgtt tacgggggat ggcgatagac gactttggtg acttgggcga      300
ttctgtgtgt cgcaaaatatc gcagtttcga tataggtgac agacgatatg aggctatatc      360
gccgatagag gcgacatcaa gctggcacat ggccaatgca tatcgatcta tacattgaat      420
caatattggc cattagccat attattcatt ggttatatag cataaatcaa tattggctat      480
tggccattgc atacgttgta tccatatcat aatatgtaca tttatattgg ctcatgtcca      540
acattaccgc catgttgaca ttgattattg actagttatt aatagtaatc aattacgggg      600
tcattagttc atagcccata tatggagttc cgcgttacat aacttacggt aaatggcccg      660
cctggctgac cgcccaacga cccccgccca ttgacgtcaa taatgacgta tgttcccata      720
gtaacgccaa tagggacttt ccattgacgt caatgggtgg agtatttacg gtaaactgcc      780
cacttggcag tacatcaagt gtatcatatg ccaagtacgc ccctattga cgtcaatgac      840
ggtaaatggc ccgcctggca ttatgcccag tacatgacct tatgggactt tcctacttgg      900
cagtacatct acgtattagt catcgctatt accatggtga tgcggttttg gcagtacatc      960
aatgggcgtg gatagcggtt tgactcacgg ggatttccaa gtctccaccc cattgacgtc     1020
aatgggagtt tgttttggca ccaaaatcaa cgggactttc caaaatgtcg taacaactcc     1080
gccccattga gcaaatgggc ggtaggcgt gtacggtggg aggtctatat aagcagagct     1140
cgtttagtga accgtcagat cgcctggaga cgccatccac gctgttttga cctccataga     1200
agacaccggg accgatccag cctccgcggc cgggaacggt gcattggaac gcggattccc     1260
cgtgccaaga gtgacgtaag taccgcctat agagtctata ggcccacccc cttggcttct     1320
tatgcatgct atactgtttt tggcttgggg tctatacacc cccgcttcct catgttatag     1380
gtgatggtat agcttagcct ataggtgtgg gttattgacc attattgacc actccctat      1440
tggtgacgat actttccatt actaatccat aacatggctc tttgccacaa ctctctttat     1500
tggctatatg ccaatacact gtccttcaga gactgacacg gactctgtat ttttacagga     1560
tggggtctca tttattattt acaaattcac atatacaaca ccaccgtccc cagtgcccgc     1620
agtttttatt aaacataacg tgggatctcc acgcgaatct cgggtacgtg ttccggacat     1680
gggctcttct ccggtagcgg cggagcttct acatccgagc cctgctccca tgcctccagc     1740
gactcatggt cgctcggcag ctccttgctc ctaacagtgg aggccagact taggcacagc     1800
acgatgccca ccaccaccag tgtgccgcac aaggccgtgg cggtagggta tgtgtctgaa     1860
aatgagctcg gggagcgggc ttgcaccgct gacgcatttg gaagacttaa ggcagcggca     1920
gaagaagatg caggcagctg agttgttgtg ttctgataag agtcagaggt aactcccgtt     1980
gcggtgctgt taacggtgga gggcagtgta gtctgagcag tactcgttgc tgccgcgcgc     2040
```

```
gccaccagac ataatagctg acagactaac agactgttcc tttccatggg tcttttctgc    2100
agtcaccgtc cttgacacgt ctaga                                          2125

<210> SEQ ID NO 7
<211> LENGTH: 28
<212> TYPE: DNA
<213> ORGANISM: Artificial Sequence
<220> FEATURE:
<223> OTHER INFORMATION: BamH1 Gln-F primer

<400> SEQUENCE: 7
ggccggatcc ggcgcgcctg cagtgaat                                         28

<210> SEQ ID NO 8
<211> LENGTH: 49
<212> TYPE: DNA
<213> ORGANISM: Artificial Sequence
<220> FEATURE:
<223> OTHER INFORMATION: Nhe1 Gln-R primer

<400> SEQUENCE: 8
ggccctcgag aaagatctgg cctagccgtg tcaaggacgg tgactgcag                  49

<210> SEQ ID NO 9
<211> LENGTH: 25
<212> TYPE: DNA
<213> ORGANISM: Artificial Sequence
<220> FEATURE:
<223> OTHER INFORMATION: SalI DHFR-F primer

<400> SEQUENCE: 9
ggccgtcgac atggttcgac cgctg                                            25

<210> SEQ ID NO 10
<211> LENGTH: 31
<212> TYPE: DNA
<213> ORGANISM: Artificial Sequence
<220> FEATURE:
<223> OTHER INFORMATION: NheI DHFR-R primer

<400> SEQUENCE: 10
ggccgctagc ttagcctttc ttctcataga c                                     31

<210> SEQ ID NO 11
<211> LENGTH: 728
<212> TYPE: DNA
<213> ORGANISM: Artificial Sequence
<220> FEATURE:
<223> OTHER INFORMATION: bevacizumab light chain

<400> SEQUENCE: 11
gctagcgcca ccatgggctg gtcctgcatc atcctgttcc tggtggccac cgccaccggc      60
gtgcactccg acatccagat gacccagtcc cctcctcccc tgtccgcctc cgtgggcgac     120
cgggtgacca tcacctgctc cgcctcccag gacatctcca actacctgaa ctggtaccag     180
cagaagcccg gcaaggcccc caaggtgctg atctacttca cctcctccct gcactccggc     240
gtgccctccc ggttctccgg ctccggctcc ggcaccgact caccctgac catctcctcc      300 ctgcagcccg aggacttcgc cacctactac tgccagcagt actccaccgt gccctggacc     360
ttcggccagg gcaccaaggt ggagatcaag cggaccgtgg ccgccccctc cgtgttcatc     420
ttcccccccc ccgacgagca gctgaagtcc ggcaccgcct ccgtggtgtg cctgctgaac     480
```

| aacttctacc | cccgggaggc | caaggtgcag | tggaaggtgg | acaacgccct | gcagtccggc | 540 |
| aactcccagg | agtccgtgac | cgagcaggac | tccaaggact | ccacctactc | cctgtcctcc | 600 |
| accctgaccc | tgtccaaggc | cgactacgag | aagcacaagg | tgtacgcctg | cgaggtgacc | 660 |
| caccagggcc | tgtcctcccc | cgtgaccaag | tccttcaacc | ggggcgagtg | ctgagcggcc | 720 |
| gcctcgag | | | | | | 728 |

<210> SEQ ID NO 12
<211> LENGTH: 1445
<212> TYPE: DNA
<213> ORGANISM: Artificial Sequence
<220> FEATURE:
<223> OTHER INFORMATION: bevacizumab heavy chain

<400> SEQUENCE: 12

| gctagcgcca | ccatgggctg | gtcctgcatc | atcctgttcc | tggtggccac | cgccaccggc | 60 |
| gtgcactccg | aggtgcagct | ggtggagtcc | ggcggcggcc | tggtgcagcc | cggcggctcc | 120 |
| ctgcggctgt | cctgcgccgc | ctccggctac | accttcacca | actacggcat | gaactgggtg | 180 |
| cggcaggccc | ccggcaaggg | cctggagtgg | gtgggctgga | tcaacaccta | caccggcgag | 240 |
| cccacctacg | ccgccgactt | caagcggcgg | ttcaccttct | ccctggacac | ctccaagtcc | 300 |
| accgcctacc | tgcagatgaa | ctccctgcgg | gccgaggaca | ccgccgtgta | ctactgcgcc | 360 |
| aagtaccccc | actactacgg | ctcctcccac | tggtacttcg | acgtgtgggg | ccagggcacc | 420 |
| ctggtgaccg | tgtcctccgc | ctccaccaag | ggcccctccg | tgttccccct | ggccccctcc | 480 |
| tccaagtcca | cctccggcgg | caccgccgcc | ctgggctgcc | tggtgaagga | ctacttcccc | 540 |
| gagcccgtga | ccgtgtcctg | gaactccggc | gccctgacct | ccggcgtgca | caccttcccc | 600 |
| gccgtgctgc | agtcctccgg | cctgtactcc | ctgtcctccg | tggtgaccgt | gccctcctcc | 660 |
| tccctgggca | cccagaccta | catctgcaac | gtgaaccaca | agccctccaa | caccaaggtg | 720 |
| gacaagaagg | tggagcccaa | gtcctgcgac | aagacccaca | cctgcccccc | ctgccccgcc | 780 |
| cccgagctgc | tgggcggccc | ctccgtgttc | ctgttccccc | ccaagcccaa | ggacaccctg | 840 |
| atgatctccc | ggacccccga | ggtgacctgc | gtggtggtgg | acgtgtccca | cgaggacccc | 900 |
| gaggtgaagt | tcaactggta | cgtggacggc | gtggaggtgc | acaacgccaa | gaccaagccc | 960 |
| cgggaggagc | agtacaactc | cacctaccgg | gtggtgtccg | tgctgaccgt | gctgcaccag | 1020 |
| gactggctga | acggcaagga | gtacaagtgc | aaggtgtcca | acaaggccct | gcccgccccc | 1080 |
| atcgagaaga | ccatctccaa | ggccaagggc | cagccccggg | agccccaggt | gtacaccctg | 1140 |
| cccccctccc | gggaggagat | gaccaagaac | caggtgtccc | tgacctgcct | ggtgaagggc | 1200 |
| ttctacccct | ccgacatcgc | cgtggagtgg | gagtccaacg | gccagcccga | gaacaactac | 1260 |
| aagaccaccc | cccccgtgct | ggactccgac | ggctccttct | tcctgtactc | caagctgacc | 1320 |
| gtggacaagt | cccggtggca | gcagggcaac | gtgttctcct | gctccgtgat | gcacgaggcc | 1380 |
| ctgcacaacc | actacaccca | gaagtccctg | tccctgtccc | ccggcaagtg | agcggccgcc | 1440 |
| tcgag | | | | | | 1445 |

<210> SEQ ID NO 13
<211> LENGTH: 214
<212> TYPE: PRT
<213> ORGANISM: Artificial Sequence
<220> FEATURE:
<223> OTHER INFORMATION: bevacizumab light chain

<400> SEQUENCE: 13

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 14
<211> LENGTH: 453
<212> TYPE: PRT
<213> ORGANISM: Artificial Sequence
<220> FEATURE:
<223> OTHER INFORMATION: bevacizumab heavy chain

<400> SEQUENCE: 14

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
                260                 265                 270

Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn Ser
        290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
                340                 345                 350

Gln Val Tyr Thr Leu Pro Pro Ser Arg Glu Glu Met Thr Lys Asn Gln
            355                 360                 365

Val Ser Leu Thr Cys Leu Val Lys Gly Phe Tyr Pro Ser Asp Ile Ala
        370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
                420                 425                 430

Val Met His Glu Ala Leu His Asn His Tyr Thr Gln Lys Ser Leu Ser
            435                 440                 445

Leu Ser Pro Gly Lys
    450

<210> SEQ ID NO 15
<211> LENGTH: 739
<212> TYPE: DNA
<213> ORGANISM: Artificial Sequence
<220> FEATURE:
<223> OTHER INFORMATION: tocilizumab light chain

<400> SEQUENCE: 15
gctagcaagc ttgccaccat gggctggtcc tgcatcatcc tgttcctggt ggccaccgcc      60
accggcgtgc actccgacat ccagatgacc cagtcccccc tctccctgtc cgcctccgtg     120
ggcgaccggg tgaccatcac ctgccgggcc tcccaggaca tctcctccta cctgaactgg     180
taccagcaga agcccggcaa ggccccccaag ctgctgatct actacacctc ccggctgcac     240

```
tccggcgtgc cctcccggtt ctccggctcc ggctccggca ccgacttcac cttcaccatc      300
tcctccctgc agcccgagga catcgccacc tactactgcc agcagggcaa caccctgccc      360
tacaccttcg gccagggcac caaggtggag atcaagcgga ccgtggccgc ccctccgtg       420 ttcatcttcc ccccctccga cgagcagctg aagtccggca ccgcctccgt ggtgtgcctg      480
ctgaacaact tctaccccg ggaggccaag gtgcagtgga aggtggacaa cgccctgcag       540
tccggcaact cccaggagtc cgtgaccgag caggactcca aggactccac ctactccctg      600
tcctccaccc tgaccctgtc caaggccgac tacgagaagc acaaggtgta cgcctgcgag      660
gtgacccacc agggcctgtc ctcccccgtg accaagtcct caaccggggg cgagtgctga      720
gaattcgcgg ccgctcgag                                                  739
```

```
<210> SEQ ID NO 16
<211> LENGTH: 1444
<212> TYPE: DNA
<213> ORGANISM: Artificial Sequence
<220> FEATURE:
<223> OTHER INFORMATION: tocilizumab heavy chain

<400> SEQUENCE: 16
gctagcaagc ttgccaccat gggctggtcc tgcatcatcc tgttcctggt ggccaccgcc       60
accggcgtgc actcccaggt gcagctgcag gagtccggcc ccggcctggt gcggccctcc      120
cagaccctgt ccctgacctg caccgtgtcc ggctactcca tcacctccga ccacgcctgg      180
tcctgggtgc ggcagccccc cggccggggc ctggagtgga tcggctacat tcctactcc       240 ggcatcacca cctacaaccc ctccctgaag tcccgggtga ctatgctgcg ggacacctcc      300
aagaaccagt tctccctgcg gctgtcctcc gtgaccgccg ccgacaccgc cgtgtactac      360
tgcgcccggt ccctggcccg gaccaccgct atggactact ggggccaggg ctccctggtg      420
accgtgtcct ccgcctccac caagggcccc tccgtgttcc cctggcccc ctcctccaag       480 tccacctccg gcggcaccgc cgccctgggc tgcctggtga aggactactt ccccgagccc      540
gtgaccgtgt cctggaactc cggcgccctg acctccggcg tgcacacctt ccccgccgtg      600
ctgcagtcct ccggcctgta ctccctgtcc tccgtggtga ctgtgccctc ctcctccctg      660
ggcacccaga cctacatctg caacgtgaac cacaagccct ccaacaccaa ggtggacaag      720
aaggtggagc ccaagtcctg cgacaagacc cacacctgcc cccctgccc cgcccccgag       780 ctgctgggcg gccctccgt gttcctgttc ccccccaagc ccaaggacac cctgatgatc       840
tcccggaccc ccgaggtgac ttgcgtggtg gtggacgtgt cccacgagga ccccgaggtg      900
aagttcaact ggtacgtgga cggcgtggag gtgcacaacg ccaagaccaa gccccgggag      960
gagcagtaca actccaccta ccgggtggtg tccgtgctga ccgtgctgca ccaggactgg     1020
ctgaacggca aggagtacaa gtgcaaggtg tccaacaagg ccctgcccgc ccccatcgag     1080
aagaccatct ccaaggccaa gggccagccc cgggagcccc aggtgtacac cctgccccc      1140 tcccgggacg agctgaccaa gaaccaggtg tccctgacct gcctggtgaa gggcttctac     1200
ccctccgaca tcgccgtgga gtgggagtcc aacggccagc cgagaacaa ctacaagacc      1260 acccccccg tgctggactc cgacggctcc ttcttcctgt actccaagct gaccgtggac      1320
aagtcccggt ggcagcaggg caacgtgttc tcctgctccg tgatgcacga ggccctgcac     1380
aaccactaca cccagaagtc cctgtccctg tcccccggca agtgagaatt cgcggccgct     1440
cgag                                                                 1444
```

-continued

```
<210> SEQ ID NO 17
<211> LENGTH: 233
<212> TYPE: PRT
<213> ORGANISM: Artificial Sequence
<220> FEATURE:
<223> OTHER INFORMATION: ocilizumab light chain

<400> SEQUENCE: 17
```

Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Arg Ala Ser Gln Asp Ile
        35                  40                  45

Ser Ser Tyr Leu Asn Trp Tyr Gln Gln Lys Pro Gly Lys Ala Pro Lys
    50                  55                  60

Leu Leu Ile Tyr Tyr Thr Ser Arg Leu His Ser Gly Val Pro Ser Arg
65                  70                  75                  80

Phe Ser Gly Ser Gly Ser Gly Thr Asp Phe Thr Phe Thr Ile Ser Ser
                85                  90                  95

Leu Gln Pro Glu Asp Ile Ala Thr Tyr Tyr Cys Gln Gln Gly Asn Thr
            100                 105                 110

Leu Pro Tyr Thr Phe Gly Gln Gly Thr Lys Val Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230

```
<210> SEQ ID NO 18
<211> LENGTH: 468
<212> TYPE: PRT
<213> ORGANISM: Artificial Sequence
<220> FEATURE:
<223> OTHER INFORMATION: tocilizumab heavy chain

<400> SEQUENCE: 18
```

Met Gly Trp Ser Cys Ile Ile Leu Phe Leu Val Ala Thr Ala Thr Gly
1               5                   10                  15

Val His Ser Gln Val Gln Leu Gln Glu Ser Gly Pro Gly Leu Val Arg
            20                  25                  30

Pro Ser Gln Thr Leu Ser Leu Thr Cys Thr Val Ser Gly Tyr Ser Ile
        35                  40                  45

Thr Ser Asp His Ala Trp Ser Trp Val Arg Gln Pro Pro Gly Arg Gly
    50                  55                  60

Leu Glu Trp Ile Gly Tyr Ile Ser Tyr Ser Gly Ile Thr Thr Tyr Asn
65                  70                  75                  80

Pro Ser Leu Lys Ser Arg Val Thr Met Leu Arg Asp Thr Ser Lys Asn
            85                  90                  95

Gln Phe Ser Leu Arg Leu Ser Ser Val Thr Ala Ala Asp Thr Ala Val
        100                 105                 110

Tyr Tyr Cys Ala Arg Ser Leu Ala Arg Thr Thr Ala Met Asp Tyr Trp
        115                 120                 125

Gly Gln Gly Ser Leu Val Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Lys Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
        355                 360                 365

Val Tyr Thr Leu Pro Pro Ser Arg Asp Glu Leu Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
        435                 440                 445

Met His Glu Ala Leu His Asn His Tyr Thr Gln Lys Ser Leu Ser Leu
    450                 455                 460

Ser Pro Gly Lys
465

<210> SEQ ID NO 19
<211> LENGTH: 742
<212> TYPE: DNA

```
<213> ORGANISM: Artificial Sequence
<220> FEATURE:
<223> OTHER INFORMATION: denosumab light chain

<400> SEQUENCE: 19
gctagcaagc ttgccaccat gggctggtcc tgcatcatcc tgttcctggt ggccaccgcc      60
accggcgtgc actccgagat cgtgctgacc cagtccccg gcaccctgtc cctgtccccc     120
ggcgagcggg ccaccctgtc ctgccgggcc tcccagtccg tgcggggccg gtacctggcc     180
tggtaccagc agaagcccgg ccaggccccc cggctgctga tctacggcgc ctcctcccgg     240
gccaccggca tccccgaccg gttctccggc tccggctccg gcaccgactt caccctgacc     300
atctcccggc tggagcccga ggacttcgcc gtgttctact gccagcagta cggctcctcc     360 cccccggacct tcggccaggg caccaaggtg gagatcaagc ggaccgtggc cgccccctcc     420
gtgttcatct tcccccccctc cgacgagcag ctgaagtccg gcaccgcctc cgtggtgtgc     480
ctgctgaaca acttctaccc ccgggaggcc aaggtgcagt ggaaggtgga caacgccctg     540
cagtccggca actcccagga gtccgtgacc gagcaggact ccaaggactc cacctactcc     600
ctgtcctcca ccctgaccct gtccaaggcc gactacgaga gcacaaggt gtacgcctgc     660 gaggtgaccc accagggcct gtcctccccc gtgaccaagt ccttcaaccg gggcgagtgc     720
tgagaattcg cggccgctcg ag                                              742

<210> SEQ ID NO 20
<211> LENGTH: 1441
<212> TYPE: DNA
<213> ORGANISM: Artificial Sequence
<220> FEATURE:
<223> OTHER INFORMATION: denosumab heavy chain

<400> SEQUENCE: 20
gctagcaagc ttgccaccat gggctggtcc tgcatcatcc tgttcctggt ggccaccgcc      60
accggcgtgc actccgaggt gcagctgctg gagtccggcg gcggcctggt gcagcccggc     120
ggctccctgc ggctgtcctg cgccgcctcc ggcttcacct tctcctccta cgccatgtcc     180
tgggtgcggc aggccccccgg caagggcctg gagtgggtgt ccggcatcac cggctccggc     240
ggctccacct actacgccga ctccgtgaag ggccggttca ccatctcccg ggacaactcc     300
aagaacaccc tgtacctgca gatgaactcc ctgcgggccg aggacaccgc cgtgtactac     360
tgcgccaagg accccggcac caccgtgatt atgtcctggt tcgacccctg gggccagggc     420
accctggtga ccgtgtcctc cgcctccacc aagggccccct ccgtgttccc cctggccccc     480
tgctcccggt ccacctccga gtccaccgcc gccctgggct gcctggtgaa ggactacttc     540
cccgagcccg tgaccgtgtc ctggaactcc ggcgccctga cctccggcgt gcacaccttc     600
cccgccgtgc tgcagtcctc cggcctgtac tccctgtcct ccgtggtgac cgtgccctcc     660
tccaacttcg gcacccagac ctacacctgc aacgtggacc acaagccctc caacaccaag     720
gtggacaaga ccgtggagcg gaagtgctgc gtggagtgcc ccccctgccc cgcccccccc     780
gtggccggcc cctccgtgtt cctgttcccc cccaagccca ggacaccct gatgatctcc     840 cggacccccg aggtgacttg cgtggtggtg gacgtgtccc acgaggaccc cgaggtgcag     900
ttcaactggt acgtggacgg cgtggaggtg cacaacgcca agaccaagcc ccgggaggag     960
cagttcaact ccaccttccg ggtggtgtcc gtgctgaccg tggtgcacca ggactggctg    1020
aacggcaagg agtacaagtg caaggtgtcc aacaagggcc tgcccgcccc catcgagaag    1080
accatctcca gaccaaggg ccagccccgg gagcccagg tgtacaccct gcccccctcc    1140
```

```
cgggaggaga tgaccaagaa ccaggtgtcc ctgacctgcc tggtgaaggg cttctacccc      1200
tccgacatcg ccgtggagtg ggagtccaac ggccagccg agaacaacta caagaccacc      1260
ccccccatgc tggactccga cggctccttc ttcctgtact ccaagctgac cgtggacaag      1320
tcccggtggc agcagggcaa cgtgttctcc tgctccgtga tgcacgaggc cctgcacaac      1380
cactacaccc agaagtccct gtccctgtcc cccggcaagt gagaattcgc ggccgctcga      1440
g                                                                      1441

<210> SEQ ID NO 21
<211> LENGTH: 234
<212> TYPE: PRT
<213> ORGANISM: Artificial Sequence
<220> FEATURE:
<223> OTHER INFORMATION: denosumab light chain

<400> SEQUENCE: 21

Met Gly Trp Ser Cys Ile Ile Leu Phe Leu Val Ala Thr Ala Thr Gly
1               5                   10                  15

Val His Ser Glu Ile Val Leu Thr Gln Ser Pro Gly Thr Leu Ser Leu
            20                  25                  30

Ser Pro Gly Glu Arg Ala Thr Leu Ser Cys Arg Ala Ser Gln Ser Val
        35                  40                  45

Arg Gly Arg Tyr Leu Ala Trp Tyr Gln Gln Lys Pro Gly Gln Ala Pro
    50                  55                  60

Arg Leu Leu Ile Tyr Gly Ala Ser Ser Arg Ala Thr Gly Ile Pro Asp
65                  70                  75                  80

Arg Phe Ser Gly Ser Gly Ser Gly Thr Asp Phe Thr Leu Thr Ile Ser
                85                  90                  95

Arg Leu Glu Pro Glu Asp Phe Ala Val Phe Tyr Cys Gln Gln Tyr Gly
            100                 105                 110

Ser Ser Pro Arg Thr Phe Gly Gln Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 22
<211> LENGTH: 467
<212> TYPE: PRT
<213> ORGANISM: Artificial Sequence
<220> FEATURE:
<223> OTHER INFORMATION: denosumab heavy chain

<400> SEQUENCE: 22

Met Gly Trp Ser Cys Ile Ile Leu Phe Leu Val Ala Thr Ala Thr Gly
```

-continued

```
1               5                   10                  15
Val His Ser Glu Val Gln Leu Leu Glu Ser Gly Gly Gly Leu Val Gln
                20                  25                  30
Pro Gly Gly Ser Leu Arg Leu Ser Cys Ala Ala Ser Gly Phe Thr Phe
                35                  40                  45
Ser Ser Tyr Ala Met Ser Trp Val Arg Gln Ala Pro Gly Lys Gly Leu
                50                  55                  60
Glu Trp Val Ser Gly Ile Thr Gly Ser Gly Gly Ser Thr Tyr Tyr Ala
65                      70                  75                  80
Asp Ser Val Lys Gly Arg Phe Thr Ile Ser Arg Asp Asn Ser Lys Asn
                    85                  90                  95
Thr Leu Tyr Leu Gln Met Asn Ser Leu Arg Ala Glu Asp Thr Ala Val
                100                 105                 110
Tyr Tyr Cys Ala Lys Asp Pro Gly Thr Thr Val Ile Met Ser Trp Phe
                115                 120                 125
Asp Pro Trp Gly Gln Gly Thr Leu Val Thr Val Ser Ser Ala Ser Thr
            130                 135                 140
Lys Gly Pro Ser Val Phe Pro Leu Ala Pro Cys Ser Arg Ser Thr Ser
145                 150                 155                 160
Glu Ser Thr Ala Ala Leu Gly Cys Leu Val Lys Asp Tyr Phe Pro Glu
                165                 170                 175
Pro Val Thr Val Ser Trp Asn Ser Gly Ala Leu Thr Ser Gly Val His
                180                 185                 190
Thr Phe Pro Ala Val Leu Gln Ser Ser Gly Leu Tyr Ser Leu Ser Ser
                195                 200                 205
Val Val Thr Val Pro Ser Ser Asn Phe Gly Thr Gln Thr Tyr Thr Cys
            210                 215                 220
Asn Val Asp His Lys Pro Ser Asn Thr Lys Val Asp Lys Thr Val Glu
225                 230                 235                 240
Arg Lys Cys Cys Val Glu Cys Pro Pro Cys Pro Ala Pro Pro Val Ala
                245                 250                 255
Gly Pro Ser Val Phe Leu Phe Pro Pro Lys Pro Lys Asp Thr Leu Met
                260                 265                 270
Ile Ser Arg Thr Pro Glu Val Thr Cys Val Val Val Asp Val Ser His
                275                 280                 285
Glu Asp Pro Glu Val Gln Phe Asn Trp Tyr Val Asp Gly Val Glu Val
            290                 295                 300
His Asn Ala Lys Thr Lys Pro Arg Glu Glu Gln Phe Asn Ser Thr Phe
305                 310                 315                 320
Arg Val Val Ser Val Leu Thr Val Val His Gln Asp Trp Leu Asn Gly
                325                 330                 335
Lys Glu Tyr Lys Cys Lys Val Ser Asn Lys Gly Leu Pro Ala Pro Ile
                340                 345                 350
Glu Lys Thr Ile Ser Lys Thr Lys Gly Gln Pro Arg Glu Pro Gln Val
                355                 360                 365
Tyr Thr Leu Pro Pro Ser Arg Glu Glu Met Thr Lys Asn Gln Val Ser
            370                 375                 380
Leu Thr Cys Leu Val Lys Gly Phe Tyr Pro Ser Asp Ile Ala Val Glu
385                 390                 395                 400
Trp Glu Ser Asn Gly Gln Pro Glu Asn Asn Tyr Lys Thr Thr Pro Pro
                405                 410                 415
Met Leu Asp Ser Asp Gly Ser Phe Phe Leu Tyr Ser Lys Leu Thr Val
                420                 425                 430
```

Asp Lys Ser Arg Trp Gln Gln Gly Asn Val Phe Ser Cys Ser Val Met
            435                 440                 445

His Glu Ala Leu His Asn His Tyr Thr Gln Lys Ser Leu Ser Leu Ser
    450                 455                 460

Pro Gly Lys
465

<210> SEQ ID NO 23
<211> LENGTH: 739
<212> TYPE: DNA
<213> ORGANISM: Artificial Sequence
<220> FEATURE:
<223> OTHER INFORMATION: Belimumab light chain

<400> SEQUENCE: 23
gctagcaagc ttgccaccat gggctggtcc tgcatcatcc tgttcctggt ggccaccgcc       60
accggcgtgc actcctcctc cgagctgacc caggaccccg ccgtgtccgt ggccctgggc      120
cagaccgtgc gggtgacctg ccaggcgac tccctgcggt cctactacgc ctcctggtac       180
cagcagaagc ccggccaggc ccccgtgctg gtgatctacg caagaacaa ccggccctcc       240 ggcatccccg accggttctc cggctcctcc tccggcaaca ccgcctccct gaccatcact      300
ggcgcccagg ccgaggacga ggccgactac tactgctcct cccgggactc ctccggcaac      360
cactgggtgt tcggcggcgg caccgagctg accgtgctgg ccagcccaa ggccgccccc       420 tccgtgaccc tgttcccccc ctcctccgag gagctgcagg ccaacaaggc caccctggtg      480
tgcctgatct ccgacttcta ccccggcgcc gtgaccgtgg cctggaaggc cgactcctcc      540
cccgtgaagg ccggcgtgga gaccaccacc ccctccaagc agtccaacaa caagtacgcc      600
gcctcctcct acctgtccct gacccccgag cagtggaagt cccaccggtc ctactcctgc      660
caggtgaccc acgagggctc caccgtggag aagaccgtgg cccccaccga gtgctcctga     720
gaattcgcgg ccgctcgag                                                   739

<210> SEQ ID NO 24
<211> LENGTH: 1456
<212> TYPE: DNA
<213> ORGANISM: Artificial Sequence
<220> FEATURE:
<223> OTHER INFORMATION: Belimumab heavy chain

<400> SEQUENCE: 24
gctagcaagc ttgccaccat gggctggtcc tgcatcatcc tgttcctggt ggccaccgcc       60
accggcgtgc actcccaggt gcagctgcag cagtccggcg ccgaggtgaa gaagcccggc      120
tcctccgtgc gggtgtcctg caaggcctcc ggcggcacct tcaacaacaa cgccatcaac      180
tgggtgcggc aggcccccgg ccagggcctg gagtggatgg gcggcatcat ccccatgttc      240
ggcaccgcca agtactccca gaacttccag ggcggggtgg ccatcaccgc cgacgagtcc      300
accggcaccg cctccatgga gctgtcctcc ctgcggtccg aggacaccgc cgtgtactac      360
tgcgcccggt cccggggacct gctgctgttc ccccaccacg ccctgtcccc ctggggccgg      420
ggcaccatgg tgaccgtgtc ctccgcctcc accaagggcc cctccgtgtt ccccctggcc      480
ccctcctcca gtccacctc cggcggcacc gccgccctgg gctgcctggt gaaggactac      540
ttccccgagc ccgtgaccgt gtcctggaac tccggcgccc tgacctccgg cgtgcacacc      600
ttccccgccg tgctgcagtc ctccggcctg tactccctgt cctccgtggt gactgtgccc      660
tcctcctccc tgggcaccca gacctacatc tgcaacgtga accacaagcc ctccaacacc     720

```
aaggtggaca agaaggtgga gcccaagtcc tgcgacaaga cccacacctg cccccctgc    780
cccgccccg agctgctggg cggcccctcc gtgttcctgt tccccccaa gcccaaggac     840
accctgatga tctcccggac ccccgaggtg acttgcgtgg tggtggacgt gtcccacgag   900
gaccccgagg tgaagttcaa ctggtacgtg gacggcgtgg aggtgcacaa cgccaagacc   960
aagccccggg aggagcagta caactccacc taccgggtgg tgtccgtgct gaccgtgctg  1020
caccaggact ggctgaacgg caaggagtac aagtgcaagg tgtccaacaa ggccctgccc  1080
gcccccatcg agaagaccat ctccaaggcc aagggccagc ccgggagcc ccaggtgtac   1140
accctgcccc cctcccggga cgagctgacc aagaaccagg tgtccctgac ctgcctggtg  1200
aagggcttct accccctcga catcgccgtg gagtgggagt ccaacggcca gcccgagaac  1260
aactacaaga ccacccccc cgtgctggac tccgacggct ccttcttcct gtactccaag   1320
ctgaccgtgg acaagtcccg gtggcagcag ggcaacgtgt tctcctgctc cgtgatgcac  1380
gaggccctgc acaaccacta cacccagaag tccctgtccc tgtccccgg caagtgagaa   1440
ttcgcggccg ctcgag                                                  1456
```

<210> SEQ ID NO 25
<211> LENGTH: 233
<212> TYPE: PRT
<213> ORGANISM: Artificial Sequence
<220> FEATURE:
<223> OTHER INFORMATION: Belimumab light chain

<400> SEQUENCE: 25

```
Met Gly Trp Ser Cys Ile Ile Leu Phe Leu Val Ala Thr Ala Thr Gly
1               5                   10                  15
Val His Ser Ser Glu Leu Thr Gln Asp Pro Ala Val Ser Val Ala
            20                  25                  30
Leu Gly Gln Thr Val Arg Val Thr Cys Gln Gly Asp Ser Leu Arg Ser
        35                  40                  45
Tyr Tyr Ala Ser Trp Tyr Gln Gln Lys Pro Gly Gln Ala Pro Val Leu
    50                  55                  60
Val Ile Tyr Gly Lys Asn Asn Arg Pro Ser Gly Ile Pro Asp Arg Phe
65                  70                  75                  80
Ser Gly Ser Ser Ser Gly Asn Thr Ala Ser Leu Thr Ile Thr Gly Ala
                85                  90                  95
Gln Ala Glu Asp Glu Ala Asp Tyr Tyr Cys Ser Ser Arg Asp Ser Ser
            100                 105                 110
Gly Asn His Trp Val Phe Gly Gly Gly Thr Glu Leu Thr Val Leu Gly
        115                 120                 125
Gln Pro Lys Ala Ala Pro Ser Val Thr Leu Phe Pro Pro Ser Ser Glu
    130                 135                 140
Glu Leu Gln Ala Asn Lys Ala Thr Leu Val Cys Leu Ile Ser Asp Phe
145                 150                 155                 160
Tyr Pro Gly Ala Val Thr Val Ala Trp Lys Ala Asp Ser Ser Pro Val
                165                 170                 175
Lys Ala Gly Val Glu Thr Thr Thr Pro Ser Lys Gln Ser Asn Asn Lys
            180                 185                 190
Tyr Ala Ala Ser Ser Tyr Leu Ser Leu Thr Pro Glu Gln Trp Lys Ser
        195                 200                 205
His Arg Ser Tyr Ser Cys Gln Val Thr His Glu Gly Ser Thr Val Glu
    210                 215                 220
```

-continued

Lys Thr Val Ala Pro Thr Glu Cys Ser
225                 230

<210> SEQ ID NO 26
<211> LENGTH: 472
<212> TYPE: PRT
<213> ORGANISM: Artificial Sequence
<220> FEATURE:
<223> OTHER INFORMATION: Belimumab heavy chain

<400> SEQUENCE: 26

Met Gly Trp Ser Cys Ile Ile Leu Phe Leu Val Ala Thr Ala Thr Gly
1               5                   10                  15

Val His Ser Gln Val Gln Leu Gln Gln Ser Gly Ala Glu Val Lys Lys
            20                  25                  30

Pro Gly Ser Ser Val Arg Val Ser Cys Lys Ala Ser Gly Gly Thr Phe
        35                  40                  45

Asn Asn Asn Ala Ile Asn Trp Val Arg Gln Ala Pro Gly Gln Gly Leu
    50                  55                  60

Glu Trp Met Gly Gly Ile Ile Pro Met Phe Gly Thr Ala Lys Tyr Ser
65                  70                  75                  80

Gln Asn Phe Gln Gly Arg Val Ala Ile Thr Ala Asp Glu Ser Thr Gly
                85                  90                  95

Thr Ala Ser Met Glu Leu Ser Ser Leu Arg Ser Glu Asp Thr Ala Val
            100                 105                 110

Tyr Tyr Cys Ala Arg Ser Arg Asp Leu Leu Leu Phe Pro His His Ala
        115                 120                 125

Leu Ser Pro Trp Gly Arg Gly Thr Met Val Thr Val Ser Ser Ala Ser
    130                 135                 140

Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Ser Leu Gly Thr Gln Thr Tyr Ile
    210                 215                 220

Cys Asn Val Asn His Lys Pro Ser Asn Thr Lys Val Asp Lys Lys Val
225                 230                 235                 240

Glu Pro Lys Ser Cys Asp Lys Thr His Thr Cys Pro Pro Cys Pro Ala
                245                 250                 255

Pro Glu Leu Leu Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser His Glu Asp Pro Glu Val Lys Phe Asn Trp Tyr Val
    290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
            340                 345                 350

```
Leu Pro Ala Pro Ile Glu Lys Thr Ile Ser Lys Ala Lys Gly Gln Pro
            355                 360                 365

Arg Glu Pro Gln Val Tyr Thr Leu Pro Pro Ser Arg Asp Glu Leu Thr
    370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Tyr
            420                 425                 430

Ser Lys Leu Thr Val Asp Lys Ser Arg Trp Gln Gln Gly Asn Val Phe
        435                 440                 445

Ser Cys Ser Val Met His Glu Ala Leu His Asn His Tyr Thr Gln Lys
    450                 455                 460

Ser Leu Ser Leu Ser Pro Gly Lys
465                 470

<210> SEQ ID NO 27
<211> LENGTH: 742
<212> TYPE: DNA
<213> ORGANISM: Artificial Sequence
<220> FEATURE:
<223> OTHER INFORMATION: golimumab light chain

<400> SEQUENCE: 27
gctagcaagc ttgccaccat gggctggtcc tgcatcatcc tgttcctggt ggccaccgcc      60
accggcgtgc actccgagat cgtgctgacc cagtcccccg ccaccctgtc cctgtccccc     120
ggcgagcggg ccaccctgtc ctgccggggc tcccagtccg tgtactccta cctggcctgg     180
taccagcaga agcccggcca ggccccccgg ctgctgatct acgacgcctc caaccgggcc     240
accggcatcc ccgcccggtt ctccggctcc ggctccggca ccgacttcac cctgaccatc     300
tcctccctgg agcccgagga cttcgccgtg tactactgcc agcagcggtc caactggccc     360
cccttcacct tcggccccgg caccaaggtg gacatcaagc ggaccgtggc cgccccctcc     420
gtgttcatct tccccccctc cgacgagcag ctgaagtccg gcaccgcctc cgtggtgtgc     480
ctgctgaaca acttctaccc ccgggaggcc aaggtgcagt ggaaggtgga caacgccctg     540
cagtccggca actcccagga gtccgtgacc gagcaggact ccaaggactc cacctactcc     600
ctgtcctcca ccctgaccct gtccaaggcc gactacgaga gcacaaggt gtacgcctgc     660 gaggtgaccc accagggcct gtcctccccc gtgaccaagt ccttcaaccg ggcgagtgc     720 tgagaattcg cggccgctcg ag                                              742

<210> SEQ ID NO 28
<211> LENGTH: 1465
<212> TYPE: DNA
<213> ORGANISM: Artificial Sequence
<220> FEATURE:
<223> OTHER INFORMATION: golimumab heavy chain

<400> SEQUENCE: 28
gctagcaagc ttgccaccat gggctggtcc tgcatcatcc tgttcctggt ggccaccgcc      60
accggcgtgc actcccaggt gcagctggtg gagtccggcg cgggcgtggt gcagcccggc     120
cggtccctgc ggctgtcctg cgccgcctcc ggcttcatct ctcctcctca cgccatgcac     180
tgggtgcggc aggcccccgg caacggcctg gagtgggtgg ccttcatgtc ctacgacggc     240
tccaacaaga agtacgccga ctccgtgaag ggccggttca ccatctcccg ggacaactcc     300
```

-continued

```
aagaacacccc tgtacctgca gatgaactcc ctgcgggccg aggacaccgc cgtgtactac    360
tgcgcccggg accggggcat cgccgctggc ggcaactact actactacgg catggacgtg    420
tggggccagg gcaccaccgt gaccgtgtcc tccgcctcca ccaagggccc ctccgtgttc    480
cccctggccc cctcctccaa gtccacctcc ggcggcaccg ccgccctggg ctgcctggtg    540
aaggactact cccccgagcc cgtgaccgtg tcctggaact ccggcgccct gacctccggc    600
gtgcacacct cccccgccgt gctgcagtcc tccggcctgt actccctgtc ctccgtggtg    660
actgtgccct cctcctccct gggcacccag acctacatct gcaacgtgaa ccacaagccc    720
tccaacacca aggtggacaa gaaggtggag cccaagtcct gcgacaagac ccacacctgc    780
cccccctgcc ccgccccccga gctgctgggc ggcccctccg tgttcctgtt cccccccaag    840
cccaaggaca ccctgatgat ctcccggacc cccgaggtga cttgcgtggt ggtggacgtg    900
tcccacgagg accccgaggt gaagttcaac tggtacgtgg acggcgtgga ggtgcacaac    960
gccaagacca gccccggga ggagcagtac aactccaccct accgggtggt gtccgtgctg   1020
accgtgctgc accaggactg gctgaacggc aaggagtaca agtgcaaggt gtccaacaag   1080
gccctgcccg cccccatcga aagaccatc tccaaggcca agggcagcc ccgggagccc   1140 caggtgtaca ccctgccccc ctcccgggac gagctgacca gaaccaggt gtccctgacc   1200 tgcctggtga agggcttcta ccctcccgac atcgccgtgg agtgggagtc caacggccag   1260
cccgagaaca actacaagac caccccccc gtgctggact ccgacggctc cttcttcctg   1320
tactccaagc tgaccgtgga caagtccgg tggcagcagg gcaacgtgtt ctcctgctcc   1380
gtgatgcacg aggccctgca caaccactac acccagaagt ccctgtccct gtcccccggc   1440
aagtgagaat tcgcggccgc tcgag                                         1465
```

<210> SEQ ID NO 29
<211> LENGTH: 234
<212> TYPE: PRT
<213> ORGANISM: Artificial Sequence
<220> FEATURE:
<223> OTHER INFORMATION: golimumab light chain

<400> SEQUENCE: 29

```
Met Gly Trp Ser Cys Ile Ile Leu Phe Leu Val Ala Thr Ala Thr Gly
1               5                   10                  15

Val His Ser Glu Ile Val Leu Thr Gln Ser Pro Ala Thr Leu Ser Leu
            20                  25                  30

Ser Pro Gly Glu Arg Ala Thr Leu Ser Cys Arg Ala Ser Gln Ser Val
        35                  40                  45

Tyr Ser Tyr Leu Ala Trp Tyr Gln Gln Lys Pro Gly Gln Ala Pro Arg
    50                  55                  60

Leu Leu Ile Tyr Asp Ala Ser Asn Arg Ala Thr Gly Ile Pro Ala Arg
65                  70                  75                  80

Phe Ser Gly Ser Gly Ser Gly Thr Asp Phe Thr Leu Thr Ile Ser Ser
                85                  90                  95

Leu Glu Pro Glu Asp Phe Ala Val Tyr Tyr Cys Gln Gln Arg Ser Asn
            100                 105                 110

Trp Pro Pro Phe Thr Phe Gly Pro Gly Thr Lys Val Asp Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
```

```
                145                 150                 155                 160
Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 30
<211> LENGTH: 475
<212> TYPE: PRT
<213> ORGANISM: Artificial Sequence
<220> FEATURE:
<223> OTHER INFORMATION: golimumab heavy chain

<400> SEQUENCE: 30

Met Gly Trp Ser Cys Ile Ile Leu Phe Leu Val Ala Thr Ala Thr Gly
1               5                   10                  15

Val His Ser Gln Val Gln Leu Val Glu Ser Gly Gly Gly Val Val Gln
            20                  25                  30

Pro Gly Arg Ser Leu Arg Leu Ser Cys Ala Ala Ser Gly Phe Ile Phe
        35                  40                  45

Ser Ser Tyr Ala Met His Trp Val Arg Gln Ala Pro Gly Asn Gly Leu
    50                  55                  60

Glu Trp Val Ala Phe Met Ser Tyr Asp Gly Ser Asn Lys Lys Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Asp Arg Gly Ile Ala Ala Gly Gly Asn Tyr Tyr
        115                 120                 125

Tyr Tyr Gly Met Asp Val Trp Gly Gln Gly Thr Thr Val Thr Val Ser
    130                 135                 140

Ser Ala Ser Thr Lys Gly Pro Ser Val Phe Pro Leu Ala Pro Ser Ser
145                 150                 155                 160

Lys Ser Thr Ser Gly Gly Thr Ala Ala Leu Gly Cys Leu Val Lys Asp
                165                 170                 175

Tyr Phe Pro Glu Pro Val Thr Val Ser Trp Asn Ser Gly Ala Leu Thr
            180                 185                 190

Ser Gly Val His Thr Phe Pro Ala Val Leu Gln Ser Ser Gly Leu Tyr
        195                 200                 205

Ser Leu Ser Ser Val Val Thr Val Pro Ser Ser Leu Gly Thr Gln
    210                 215                 220

Thr Tyr Ile Cys Asn Val Asn His Lys Pro Ser Asn Thr Lys Val Asp
225                 230                 235                 240

Lys Lys Val Glu Pro Lys Ser Cys Asp Lys Thr His Thr Cys Pro Pro
                245                 250                 255

Cys Pro Ala Pro Glu Leu Leu Gly Gly Pro Ser Val Phe Leu Phe Pro
            260                 265                 270

Pro Lys Pro Lys Asp Thr Leu Met Ile Ser Arg Thr Pro Glu Val Thr
```

```
            275                 280                 285
Cys Val Val Asp Val Ser His Glu Asp Pro Glu Val Lys Phe Asn
    290                 295                 300

Trp Tyr Val Asp Gly Val Glu Val His Asn Ala Lys Thr Lys Pro Arg
305                 310                 315                 320

Glu Glu Gln Tyr Asn Ser Thr Tyr Arg Val Val Ser Val Leu Thr Val
                325                 330                 335

Leu His Gln Asp Trp Leu Asn Gly Lys Glu Tyr Lys Cys Lys Val Ser
                340                 345                 350

Asn Lys Ala Leu Pro Ala Pro Ile Glu Lys Thr Ile Ser Lys Ala Lys
                355                 360                 365

Gly Gln Pro Arg Glu Pro Gln Val Tyr Thr Leu Pro Pro Ser Arg Asp
370                 375                 380

Glu Leu Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
                405                 410                 415

Asn Asn Tyr Lys Thr Thr Pro Pro Val Leu Asp Ser Asp Gly Ser Phe
                420                 425                 430

Phe Leu Tyr Ser Lys Leu Thr Val Asp Lys Ser Arg Trp Gln Gln Gly
                435                 440                 445

Asn Val Phe Ser Cys Ser Val Met His Glu Ala Leu His Asn His Tyr
450                 455                 460

Thr Gln Lys Ser Leu Ser Leu Ser Pro Gly Lys
465                 470                 475

<210> SEQ ID NO 31
<211> LENGTH: 739
<212> TYPE: DNA
<213> ORGANISM: Artificial Sequence
<220> FEATURE:
<223> OTHER INFORMATION: Ustekinumab light chain

<400> SEQUENCE: 31
gctagcaagc ttgccaccat gggctggtcc tgcatcatcc tgttcctggt ggccaccgcc        60
accggcgtgc actccgacat ccagatgacc cagtccccct cctccctgtc cgcctccgtg       120
ggcgaccggg tgaccatcac ctgccgggcc tcccagggca tctcctcctg gctggcctgg       180
taccagcaga agcccgagaa ggccccaag tccctgatct acgccgcctc ctccctgcag       240
tccggcgtgc cctccggtt ctccggctcc ggctccggca ccgacttcac cctgaccatc       300
tcctccctgc agcccgagga cttcgccacc tactactgcc agcagtacaa catctacccc       360
tacaccttcg gccagggcac caagctggag atcaagcgga ccgtggccgc ccctccgtg        420 ttcatcttcc cccctccga cgagcagctg aagtccggca ccgcctccgt ggtgtgcctg       480
ctgaacaact tctaccccg ggaggccaag gtgcagtgga aggtggacaa cgccctgcag       540
tccggcaact cccaggagtc cgtgaccgag caggactcca aggactccac ctactccctg       600
tcctccaccc tgaccctgtc caaggccgac tacgagaagc acaaggtgta cgcctgcgag       660
gtgacccacc agggcctgtc ctcccccgtg accaagtcct tcaaccgggg cgagtgctga       720
gaattcgcgg ccgctcgag                                                  739

<210> SEQ ID NO 32
<211> LENGTH: 1426
<212> TYPE: DNA
<213> ORGANISM: Artificial Sequence
```

<220> FEATURE:
<223> OTHER INFORMATION: Ustekinumab heavy chain

<400> SEQUENCE: 32

```
atgggctggt cctgcatcat cctgttcctg gtggccaccg ccaccggcgt gcactccgag      60
gtgcagctgg tgcagtccgg cgccgaggtg aagaagcccg cgagtccct gaagatctcc     120
tgcaagggct ccggctactc cttcaccacc tactggctgg gctgggtgcg gcagatgccc     180
ggcaagggcc tggactggat cggcatcatg tcccccgtgg actccgacat ccggtactcc    240
ccctccttcc agggccaggt gactatgtcc gtggacaagt ccatcaccac cgcctacctg    300
cagtggaact ccctgaaggc ctccgacacc gccatgtact actgcgcccg cggcggcccc    360
ggccagggct acttcgactt ctggggccag ggcaccctgg tgaccgtgtc ctcctcctcc    420
accaagggcc cctccgtgtt ccccctggcc cctcctcca gtccacctc cggcggcacc      480
gccgccctgg gctgcctggt gaaggactac ttccccgagc ccgtgaccgt gtcctggaac    540
tccggcgccc tgacctccgg cgtgcacacc ttccccgccg tgctgcagtc ctccggcctg    600
tactccctgt cctccgtggt gactgtgccc tcctcctccc tgggcaccca gacctacatc    660
tgcaacgtga accacaagcc ctccaacacc aaggtggaca gcggggtgga gcccaagtcc    720
tgcgacaaga cccacacctg cccccctgc cccgcccccg agctgctggg cggcccctcc    780
gtgttcctgt tcccccccaa gcccaaggac accctgatga tctcccggac ccccgaggtg    840
acttgcgtgg tggtggacgt gtcccacgag gaccccgagg tgaagttcaa ctggtacgtg    900
gacggcgtgg aggtgcacaa cgccaagacc aagcccgg aggagcagta caactccacc     960
taccgggtgg tgtccgtgct gaccgtgctg caccaggact ggctgaacgg caaggagtac  1020
aagtgcaagg tgtccaacaa ggccctgccc gcccccatcg agaagaccat ctccaaggcc  1080
aagggccagc cccgggagcc ccaggtgtac accctgcccc cctcccggga cgagctgacc  1140
aagaaccagg tgtccctgac ctgcctggtg aagggcttct accctccga catcgccgtg   1200
gagtgggagt ccaacggcca gcccgagaac aactacaaga ccacccccc cgtgctggac  1260
tccgacggct ccttcttcct gtactccaag ctgaccgtgg acaagtcccg gtggcagcag  1320
ggcaacgtgt tctcctgctc cgtgatgcac gaggccctgc acaaccacta cacccagaag  1380
tccctgtccc tgtccccgg caagtgagaa ttcgcggccg ctcgag                  1426
```

<210> SEQ ID NO 33
<211> LENGTH: 233
<212> TYPE: PRT
<213> ORGANISM: Artificial Sequence
<220> FEATURE:
<223> OTHER INFORMATION: Ustekinumab light chain

<400> SEQUENCE: 33

```
Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Arg Ala Ser Gln Gly Ile
        35                  40                  45

Ser Ser Trp Leu Ala Trp Tyr Gln Gln Lys Pro Glu Lys Ala Pro Lys
    50                  55                  60

Ser Leu Ile Tyr Ala Ala Ser Ser Leu Gln Ser Gly Val Pro Ser Arg
65                  70                  75                  80

Phe Ser Gly Ser Gly Ser Gly Thr Asp Phe Thr Leu Thr Ile Ser Ser
```

```
              85                  90                  95
Leu Gln Pro Glu Asp Phe Ala Thr Tyr Tyr Cys Gln Gln Tyr Asn Ile
            100                 105                 110

Tyr Pro Tyr Thr Phe Gly Gln Gly Thr Lys Leu Glu Ile Lys Arg Thr
            115                 120                 125

Val Ala Ala Pro Ser Val Phe Ile Phe Pro Pro Ser Asp Glu Gln Leu
        130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230
```

<210> SEQ ID NO 34
<211> LENGTH: 468
<212> TYPE: PRT
<213> ORGANISM: Artificial Sequence
<220> FEATURE:
<223> OTHER INFORMATION: Ustekinumab heavy chain

<400> SEQUENCE: 34

```
Met Gly Trp Ser Cys Ile Ile Leu Phe Leu Val Ala Thr Ala Thr Gly
1               5                   10                  15

Val His Ser Glu Val Gln Leu Val Gln Ser Gly Ala Glu Val Lys Lys
            20                  25                  30

Pro Gly Glu Ser Leu Lys Ile Ser Cys Lys Gly Ser Gly Tyr Ser Phe
        35                  40                  45

Thr Thr Tyr Trp Leu Gly Trp Val Arg Gln Met Pro Gly Lys Gly Leu
    50                  55                  60

Asp Trp Ile Gly Ile Met Ser Pro Val Asp Ser Asp Ile Arg Tyr Ser
65                  70                  75                  80

Pro Ser Phe Gln Gly Gln Val Thr Met Ser Val Asp Lys Ser Ile Thr
                85                  90                  95

Thr Ala Tyr Leu Gln Trp Asn Ser Leu Lys Ala Ser Asp Thr Ala Met
            100                 105                 110

Tyr Tyr Cys Ala Arg Arg Arg Pro Gly Gln Gly Tyr Phe Asp Phe Trp
        115                 120                 125

Gly Gln Gly Thr Leu Val Thr Val Ser Ser Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
```

His Lys Pro Ser Asn Thr Lys Val Asp Lys Arg Val Glu Pro Lys Ser
225                 230                 235                 240

Cys Asp Lys Thr His Thr Cys Pro Pro Cys Pro Ala Pro Glu Leu Leu
            245                 250                 255

Gly Gly Pro Ser Val Phe Leu Phe Pro Pro Lys Pro Lys Asp Thr Leu
        260                 265                 270

Met Ile Ser Arg Thr Pro Glu Val Thr Cys Val Val Val Asp Val Ser
    275                 280                 285

His Glu Asp Pro Glu Val Lys Phe Asn Trp Tyr Val Asp Gly Val Glu
290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
            325                 330                 335

Gly Lys Glu Tyr Lys Cys Lys Val Ser Asn Lys Ala Leu Pro Ala Pro
        340                 345                 350

Ile Glu Lys Thr Ile Ser Lys Ala Lys Gly Gln Pro Arg Glu Pro Gln
    355                 360                 365

Val Tyr Thr Leu Pro Pro Ser Arg Asp Glu Leu Thr Lys Asn Gln Val
370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
            405                 410                 415

Pro Val Leu Asp Ser Asp Gly Ser Phe Phe Leu Tyr Ser Lys Leu Thr
        420                 425                 430

Val Asp Lys Ser Arg Trp Gln Gln Gly Asn Val Phe Ser Cys Ser Val
    435                 440                 445

Met His Glu Ala Leu His Asn His Tyr Thr Gln Lys Ser Leu Ser Leu
450                 455                 460

Ser Pro Gly Lys
465

<210> SEQ ID NO 35
<211> LENGTH: 742
<212> TYPE: DNA
<213> ORGANISM: Artificial Sequence
<220> FEATURE:
<223> OTHER INFORMATION: ipilimumab light chain

<400> SEQUENCE: 35
gctagcaagc ttgccaccat gggctggtcc tgcatcatcc tgttcctggt ggccaccgcc        60
accggcgtgc actccgagat cgtgctgacc cagtcccccg gcaccctgtc cctgtccccc       120
ggcgagcggg ccaccctgtc ctgccgggcc tcccagtccg tgggctcctc ctacctggcc       180
tggtaccagc agaagcccgg ccaggccccc cggctgctga tctacggcgc cttctcccgg       240
gccaccggca tccccgaccg gttctccggc tccggctccg gcaccgactt caccctgacc       300
atctcccggc tggagcccga ggacttcgcc gtgtactact gccagcagta cggctcctcc       360
ccctggacct tcggccaggg caccaaggtg gagatcaagc ggaccgtggc cgccccctcc       420
gtgttcatct cccccccctc cgacgagcag ctgaagtccg gcaccgcctc cgtggtgtgc       480
ctgctgaaca acttctaccc ccgggaggcc aaggtgcagt ggaaggtgga caacgccctg       540
cagtccggca actcccagga gtccgtgacc gagcaggact ccaaggactc cacctactcc       600

```
ctgtcctcca ccctgaccct gtccaaggcc gactacgaga agcacaaggt gtacgcctgc      660
gaggtgaccc accagggcct gtcctccccc gtgaccaagt ccttcaaccg gggcgagtgc      720
tgagaattcg cggccgctcg ag                                               742
```

<210> SEQ ID NO 36
<211> LENGTH: 1423
<212> TYPE: DNA
<213> ORGANISM: Artificial Sequence
<220> FEATURE:
<223> OTHER INFORMATION: ipilimumab heavy chain

<400> SEQUENCE: 36

```
atgggctggt cctgcatcat cctgttcctg gtggccaccg ccaccggcgt gcactcccag       60
gtgcagctgg tggagtccgg cggcggcgtg gtgcagcccg ccggtccct gcggctgtcc      120 tgcgccgcct ccggcttcac cttctcctcc tacaccatgc actgggtgcg gcaggccccc      180
ggcaagggcc tggagtgggt gactttcatc tcctacgacg gcaacaacaa gtactacgcc      240
gactccgtga agggccggtt caccatctcc cgggacaact ccaagaacac cctgtacctg      300
cagatgaact ccctgcgggc cgaggacacc gccatctact actgcgcccg gaccggctgg      360
ctgggcccct tcgactactg gggccagggc accctggtga ccgtgtcctc cgcctccacc      420
aagggcccct ccgtgttccc cctggccccc tcctccaagt ccacctccgg cggcaccgcc      480
gccctgggct gcctggtgaa ggactacttc cccgagcccg tgaccgtgtc ctggaactcc      540
ggcgccctga cctccggcgt gcacaccttc cccgccgtgc tgcagtcctc cggcctgtac      600
tccctgtcct ccgtggtgac tgtgccctcc tcctccctgg gcacccagac ctacatctgc      660
aacgtgaacc acaagccctc caacaccaag gtggacaagc gggtggagcc caagtcctgc      720
gacaagaccc acacctgccc ccctgcccc gcccccgagc tgctgggcgg ccctccgtg       780 ttcctgttcc ccccaagcc caaggacacc ctgatgatct cccggacccc cgaggtgact      840
tgcgtggtgg tggacgtgtc ccacgaggac cccgaggtga agttcaactg gtacgtggac      900
ggcgtggagg tgcacaacgc caagaccaag cccgggagg agcagtacaa ctccacctac      960
cgggtggtgt ccgtgctgac cgtgctgcac caggactggc tgaacggcaa ggagtacaag     1020
tgcaaggtgt ccaacaaggc cctgcccgcc ccatcgaga agaccatctc caaggccaag     1080
ggccagcccc gggagcccca ggtgtacacc ctgccccct cccgggacga gctgaccaag     1140
aaccaggtgt ccctgacctg cctggtgaag ggcttctacc cctccgacat cgccgtggag     1200
tgggagtcca acggccagcc cgagaacaac tacaagacca ccccccccgt gctggactcc     1260
gacggctcct tcttcctgta ctccaagctg accgtggaca gtcccggtg gcagcagggc     1320 aacgtgttct cctgctccgt gatgcacgag gccctgcaca accactacac ccagaagtcc     1380
ctgtccctgt cccccggcaa gtgagaattc gcggccgctc gag                      1423
```

<210> SEQ ID NO 37
<211> LENGTH: 234
<212> TYPE: PRT
<213> ORGANISM: Artificial Sequence
<220> FEATURE:
<223> OTHER INFORMATION: ipilimumab light chain

<400> SEQUENCE: 37

```
Met Gly Trp Ser Cys Ile Ile Leu Phe Leu Val Ala Thr Ala Thr Gly
1               5                   10                  15

Val His Ser Glu Ile Val Leu Thr Gln Ser Pro Gly Thr Leu Ser Leu
```

```
                    20                  25                  30
Ser Pro Gly Glu Arg Ala Thr Leu Ser Cys Arg Ala Ser Gln Ser Val
                35                  40                  45
Gly Ser Ser Tyr Leu Ala Trp Tyr Gln Gln Lys Pro Gly Gln Ala Pro
            50                  55                  60
Arg Leu Leu Ile Tyr Gly Ala Phe Ser Arg Ala Thr Gly Ile Pro Asp
65                  70                  75                  80
Arg Phe Ser Gly Ser Gly Ser Gly Thr Asp Phe Thr Leu Thr Ile Ser
                85                  90                  95
Arg Leu Glu Pro Glu Asp Phe Ala Val Tyr Tyr Cys Gln Gln Tyr Gly
            100                 105                 110
Ser Ser Pro Trp Thr Phe Gly Gln Gly Thr Lys Val Glu Ile Lys Arg
        115                 120                 125
Thr Val Ala Ala Pro Ser Val Phe Ile Phe Pro Pro Ser Asp Glu Gln
    130                 135                 140
Leu Lys Ser Gly Thr Ala Ser Val Val Cys Leu Leu Asn Asn Phe Tyr
145                 150                 155                 160
Pro Arg Glu Ala Lys Val Gln Trp Lys Val Asp Asn Ala Leu Gln Ser
                165                 170                 175
Gly Asn Ser Gln Glu Ser Val Thr Glu Gln Asp Ser Lys Asp Ser Thr
            180                 185                 190
Tyr Ser Leu Ser Ser Thr Leu Thr Leu Ser Lys Ala Asp Tyr Glu Lys
        195                 200                 205
His Lys Val Tyr Ala Cys Glu Val Thr His Gln Gly Leu Ser Ser Pro
    210                 215                 220
Val Thr Lys Ser Phe Asn Arg Gly Glu Cys
225                 230

<210> SEQ ID NO 38
<211> LENGTH: 467
<212> TYPE: PRT
<213> ORGANISM: Artificial Sequence
<220> FEATURE:
<223> OTHER INFORMATION: ipilimumab heavy chain

<400> SEQUENCE: 38

Met Gly Trp Ser Cys Ile Ile Leu Phe Leu Val Ala Thr Ala Thr Gly
1               5                   10                  15
Val His Ser Gln Val Gln Leu Val Glu Ser Gly Gly Val Val Gln
                20                  25                  30
Pro Gly Arg Ser Leu Arg Leu Ser Cys Ala Ala Ser Gly Phe Thr Phe
            35                  40                  45
Ser Ser Tyr Thr Met His Trp Val Arg Gln Ala Pro Gly Lys Gly Leu
        50                  55                  60
Glu Trp Val Thr Phe Ile Ser Tyr Asp Gly Asn Asn Lys Tyr Tyr Ala
65                  70                  75                  80
Asp Ser Val Lys Gly Arg Phe Thr Ile Ser Arg Asp Asn Ser Lys Asn
                85                  90                  95
Thr Leu Tyr Leu Gln Met Asn Ser Leu Arg Ala Glu Asp Thr Ala Ile
            100                 105                 110
Tyr Tyr Cys Ala Arg Thr Gly Trp Leu Gly Pro Phe Asp Tyr Trp Gly
        115                 120                 125
Gln Gly Thr Leu Val Thr Val Ser Ser Ala Ser Thr Lys Gly Pro Ser
    130                 135                 140
Val Phe Pro Leu Ala Pro Ser Ser Lys Ser Thr Ser Gly Gly Thr Ala
```

```
                145                 150                 155                 160
        Ala Leu Gly Cys Leu Val Lys Asp Tyr Phe Pro Glu Pro Val Thr Val
                        165                 170                 175

Ser Trp Asn Ser Gly Ala Leu Thr Ser Gly Val His Thr Phe Pro Ala
                    180                 185                 190

Val Leu Gln Ser Ser Gly Leu Tyr Ser Leu Ser Ser Val Val Thr Val
                        195                 200                 205

Pro Ser Ser Ser Leu Gly Thr Gln Thr Tyr Ile Cys Asn Val Asn His
                210                 215                 220

Lys Pro Ser Asn Thr Lys Val Asp Lys Arg Val Glu Pro Lys Ser Cys
        225                 230                 235                 240

Asp Lys Thr His Thr Cys Pro Pro Cys Pro Ala Pro Glu Leu Leu Gly
                            245                 250                 255

Gly Pro Ser Val Phe Leu Phe Pro Pro Lys Pro Lys Asp Thr Leu Met
                        260                 265                 270

Ile Ser Arg Thr Pro Glu Val Thr Cys Val Val Val Asp Val Ser His
                    275                 280                 285

Glu Asp Pro Glu Val Lys Phe Asn Trp Tyr Val Asp Gly Val Glu Val
                290                 295                 300

His Asn Ala Lys Thr Lys Pro Arg Glu Glu Gln Tyr Asn Ser Thr Tyr
        305                 310                 315                 320

Arg Val Val Ser Val Leu Thr Val Leu His Gln Asp Trp Leu Asn Gly
                            325                 330                 335

Lys Glu Tyr Lys Cys Lys Val Ser Asn Lys Ala Leu Pro Ala Pro Ile
                        340                 345                 350

Glu Lys Thr Ile Ser Lys Ala Lys Gly Gln Pro Arg Glu Pro Gln Val
                    355                 360                 365

Tyr Thr Leu Pro Pro Ser Arg Asp Glu Leu Thr Lys Asn Gln Val Ser
                370                 375                 380

Leu Thr Cys Leu Val Lys Gly Phe Tyr Pro Ser Asp Ile Ala Val Glu
        385                 390                 395                 400

Trp Glu Ser Asn Gly Gln Pro Glu Asn Asn Tyr Lys Thr Thr Pro Pro
                            405                 410                 415

Val Leu Asp Ser Asp Gly Ser Phe Phe Leu Tyr Ser Lys Leu Thr Val
                        420                 425                 430

Asp Lys Ser Arg Trp Gln Gln Gly Asn Val Phe Ser Cys Ser Val Met
                    435                 440                 445

His Glu Ala Leu His Asn His Tyr Thr Gln Lys Ser Leu Ser Leu Ser
                450                 455                 460

Pro Gly Lys
        465

<210> SEQ ID NO 39
<211> LENGTH: 19
<212> TYPE: PRT
<213> ORGANISM: Artificial Sequence
<220> FEATURE:
<223> OTHER INFORMATION: Signal Sequence

<400> SEQUENCE: 39

Met Gly Trp Ser Cys Ile Ile Leu Phe Leu Val Ala Thr Ala Thr Gly
        1               5                   10                  15

Val His Ser
```

BICISTRONIC EXPRESSION VECTOR FOR ANTIBODY EXPRESSION AND METHOD FOR PRODUCING ANTIBODY USING SAME

This application is a U.S. National Phase of PCT/KR2014/009398, filed Oct. 7, 2014, which claims the benefit of priority to Korean Patent Application No. 10-2014-0085934, filed Jul. 9, 2014, Korean Patent Application No. 10-2014-0085933, filed Jul. 9, 2014, and Korean Patent Application No. 10-2014-0085932, filed Jul. 9, 2014, Korean Patent Application No. 10-2014-0019782, filed Feb. 20, 2014, Korean Patent Application No. 10-2014-0019781, filed Feb. 20, 2014, Korean Patent Application No. 10-2014-0019780, filed Feb. 20, 2014, and Korean Patent Application No. 10-2013-0119511, filed Oct. 7, 2013.

INCORPORATION BY REFERENCE

The instant application contains a Sequence Listing which has been submitted in ASCII format via EFS-Web and is hereby incorporated by reference in its entirety. Said ASCII copy was amended on Mar. 9, 2021, is named SEQUENCE_LISTING_(PRESTIGE_2US)07_ST25.txt, and is 77,428 bytes in size.

FIELD OF THE INVENTION

The present invention relates to a bicistronic expression vector for antibody expression, an animal cell transfected with the expression vector, and a method for producing an antibody including culturing the animal cell, in which the expression vector includes a first expression cassette including 'promoter-untranslated region (UTR)-intron-antibody light chain gene-polyA' and a second expression cassette including 'promoter-UTR-intron-antibody heavy chain gene-internal ribosome entry site (IRES)-amplification gene-polyA'.

BACKGROUND OF THE INVENTION

Various human proteins have been produced by genetic recombination. However, more often than not, proteins with normal biological activities appear to be synthesized only when mammalian cells are used, due to a series of processes specific to eukaryotic cells, such as glycosylation and phosphorylation. An immunoglobulin G (IgG) gene, often used as a therapeutic antibody, consists of a heavy chain gene and a light chain gene. The heavy and light chains produced by the respective genes are linked during a folding process within a cell and discharged from the cell. Chinese hamster ovary (CHO) cells as mammalian cells are frequently used for the production of recombinant antibodies (Kaufman, et al., *Mol. Cell. Biol.* (1985) 5, 1750).

Among the various methods used for the construction of a recombinant expression vector capable of inducing a more powerful and stable gene expression in mammalian cells, the representative method is to increase the gene expression efficiency by selecting a strong promoter. A promoter is a site on DNA, in which RNA polymerase can bind and initiate mRNA synthesis due to the presence of binding sites for various transcription factors and TATA box, and the level of gene expression level varies a lot depending on the performance of the promoter. For the improvement of expression of an antibody, it is suitable to induce a high constitutive expression, and examples of representative strong promoters may include simian virus 40 (SV40) promoter, cytomegalovirus (CMV) promoter, elongation factor 1-α (EF1-α) promoter, etc.

In addition to the method of increasing the capability of a vector itself for mRNA synthesis using a strong promoter, a gene amplification system may be employed for increasing therapeutic protein productivity. A brief overview of this method is as follows. Cells are transfected with a foreign gene and only the cells, which are incorporated with the foreign gene into the chromosome, are selectively cultured by adding a chemical. Then, the selectively cultured cells are separated and an increased amount of the chemical is added to a cell culture to induce the amplification of the foreign gene incorporated into the chromosome of the selectively cultured cells. The representative genes used in gene amplification include dihydrofolate reductase (hereinafter, DHFR) and glutamine synthetase (hereinafter, GS). The type of chemicals used for amplifying the amplification genes includes methotrexate (hereinafter, MTX) for DHFR and methionine sulfoximine (hereinafter, MSX) for GS. The cell lines with more than 1,000 copies of the amplified foreign gene can be prepared by the gene amplification process.

The conventional methods for the construction of cell lines capable of constitutive expression of an antibody gene include a method, in which a plasmid vector DNA including the gene for a desired heavy chain and light chain and a vector DNA having an amplification gene are co-transfected into a cell, and the cell line incorporated with both of the two vector DNAs in the chromosome is separated (Kaufman, *Methods in Enz.* (1990) 185, 487), or a method, in which a vector for expressing an amplification gene is constructed using SV40 promoter and then the cell line with the vector incorporated into the chromosome is separated.

As another method for expressing an amplification gene, a bicistronic vector may be used. Unlike prokaryotic cells, eukaryotic cells in principle produce a single mRNA by one promoter and only the corresponding gene is translated to synthesize a protein. However, some viruses have a sequence for ribosome-binding in the middle of their mRNA sequences, and thus multiple proteins can be synthesized from a single mRNA. When an antibody gene and an amplification gene are expressed by different promoters, only the amplification gene, but not the antibody gene, may be amplified during gene amplification. However, this problem can be solved using the internal ribosome entry site (IRES) thereby expressing the genes using the same promoter. Nevertheless, the method of using the bicistronic vector also has a disadvantage in that a desired protein cannot be prepared in large-scale thus requiring a more powerful method.

Meanwhile, bevacizumab (also called Avastin) is a humanized antibody for VEGF developed by Genentech (USA) and plays a role of an angiogenesis inhibitor, and has been highlighted as an antibody therapeutic mainly used for the treatment of colorectal cancer, lung cancer, kidney cancer, brain cancer, etc. Tocilizumab (also called Actemra®) is a human monoclonal antibody for IL-6 receptors developed by Roche, a Swiss pharmaceutical company, and has been approved in USA, Europe, and Japan as a treatment for rheumatoid arthritis under the product name of Actemra. Denosumab (also called Prolia®) is a human monoclonal antibody for the receptor activator of NF-kB ligand (RANKL) developed by Amgen (USA) and has been approved in USA, Canada, and Europe as a treatment for osteoporosis under the product name of Prolia, and has also been approved in Europe as a drug for the prevention of fracture in patients with bone metastasis from solid cancer under the product name of Xgeva.

Meanwhile, belimumab (also called Benlysta®) is a human monoclonal antibody for B lymphocyte stimulator (BLyS) developed by GlaxoSmithKline (GSK), a multinational pharmaceutical company, and has been approved in USA, Canada, and Europe as a treatment for lupus (systemic lupus erythematosus, SLE). Golimumab (also called Simponi®) is a human monoclonal antibody for TNFα developed by Janssen Biotech, Inc., (formerly Centocor), a subsidiary of Johnson & Johnson, a global pharmaceutical company, and has been approved in USA, Canada, and Korea as a treatment for rheumatoid arthritis, psoriatic arthritis, and ankylosing spondylitis under the product name of Simponi.

Meanwhile, ustekinumab (also called Stelara®) is a human monoclonal antibody for interleukin-12 (IL-12) and interleukin-23 (IL-23) developed by Janssen Pharmaceuticals, Inc., a multinational pharmaceutical company, and has been approved by the U.S. Food and Drug Administration (FDA) as a treatment for psoriatic arthritis, and the drug is in clinical trials for the treatment of severe psoriasis, moderate-to-severe plaque psoriasis, multiple sclerosis, sarcoidosis, etc. Ipilimumab (also called Yervoy®) is a human monoclonal antibody for cytotoxic T-lymphocyte antigen (CTLA-4) developed by Bristol-Myers Squibb Co. (BMS), a U.S. pharmaceutical company, and has been approved by the U.S. Food and Drug Administration (FDA) as a treatment for melanoma and skin cancer under the product name of Yervoy, and the drug is in clinical trials for the treatment of non-small cell lung carcinoma (NSCLC), small cell lung cancer (SCLC), bladder cancer, and metastatic hormone-refractory prostate cancer.

There is a need for the development of a method for large-scale production of these blockbuster antibody therapeutics.

SUMMARY OF THE INVENTION

Technical Problem

The present inventors have endeavored to find a method for inducing a more powerful and stable gene expression in various mammalian cells, and as a result, they have constructed a bicistronic expression vector, which includes an untranslated region (UTR) and an intron to a conventional expression vector, and they have confirmed that the bicistronic expression vector can co-express in high yield the light and heavy chains of various antibody therapeutics along with the amplification gene, thereby completing the present invention.

Technical Solution

An object of the present invention is to provide a bicistronic expression vector for antibody expression, which includes a first expression cassette including 'promoter-untranslated region (UTR)-intron-antibody light chain gene-polyA', and a second expression cassette including 'promoter-UTR-intron-antibody heavy chain gene-internal ribosome entry site (IRES)-amplification gene-polyA'.

Another object of the present invention is to provide an animal cell transfected with the expression vector.

A further object of the present invention is to provide a method for producing an antibody including culturing the animal cell.

Advantageous Effects of the Invention

An expression vector capable of expressing a desired antibody with high expression efficiency can be constructed using the bicistronic expression vector including an intron for antibody expression according to the present invention, and the expression vector can produce the antibody with stability and high efficiency by culturing the transfected animal cell.

BEST MODE

Figure 1:
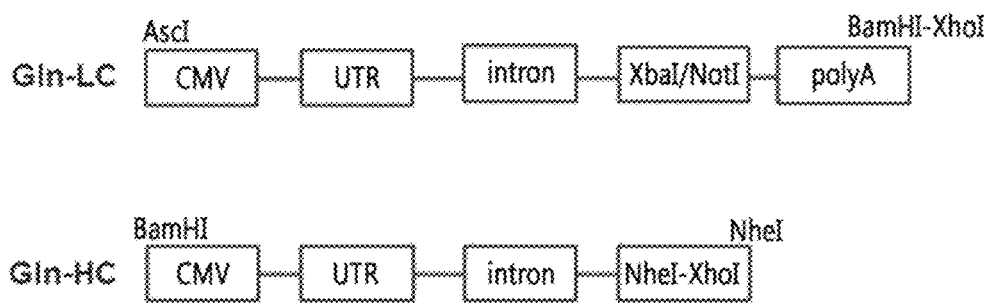
FIG. 1 shows schematic diagrams illustrating the constructed constitutions of gene fragments, the Gln-LC and the Gln-HC, according to the present invention.

In order to achieve the above objects, in an aspect, the present invention provides a bicistronic expression vector for antibody expression, including: (i) a first expression cassette including 'promoter-untranslated region (UTR)-intron-antibody light chain gene-polyA'; and (ii) a second expression cassette including 'promoter-UTR-intron-antibody heavy chain gene-internal ribosome entry site (IRES)-amplification gene-polyA'.

The present invention is directed to providing a bicistronic expression vector, which is designed to express an antibody gene for the heavy and light chains and an amplification gene as if they were a single gene, by including a UTR and an intron to enable a more powerful and stable gene expression in various mammalian cells. In particular, the present invention provides a novel expression cassette which includes a UTR and an intron.

Specifically, the present invention provides a bicistronic expression vector for antibody expression, including: (i) a first expression cassette including 'promoter-untranslated region (UTR)-intron-bevacizumab light chain gene-polyA'; and (ii) a second expression cassette including 'promoter-UTR-intron-bevacizumab heavy chain gene-internal ribosome entry site (IRES)-amplification gene-polyA'. The present invention provides a bicistronic expression vector for antibody expression, including: (i) a first expression cassette including 'promoter-untranslated region (UTR)-intron-tocilizumab light chain gene-polyA'; and (ii) a second expression cassette including 'promoter-UTR-intron-tocilizumab heavy chain gene-internal ribosome entry site (IRES)-amplification gene-polyA'. The present invention provides a bicistronic expression vector for antibody expression, including: (i) a first expression cassette including 'promoter-untranslated region (UTR)-intron-denosumab light chain gene-polyA'; and (ii) a second expression cassette including 'promoter-UTR-intron-denosumab heavy chain gene-internal ribosome entry site (IRES)-amplification gene-polyA'. The present invention provides a bicistronic expression vector for antibody expression, including: (i) a first expression cassette including 'promoter-untranslated region (UTR)-intron-belimumab light chain gene-polyA'; and (ii) a second expression cassette including 'promoter-UTR-intron-belimumab heavy chain gene-internal ribosome entry site (IRES)-amplification gene-polyA'. The present invention provides a bicistronic expression vector for antibody expression, including: (i) a first expression cassette including 'promoter-untranslated region (UTR)-intron-golimumab light chain gene-polyA'; and (ii) a second expression cassette including 'promoter-UTR-intron-golimumab heavy chain gene-internal ribosome entry site (IRES)-amplification gene-polyA'. The present invention provides a bicistronic expression vector for antibody expression, including: (i) a first expression cassette including 'promoter-untranslated region (UTR)-intron-ustekinumab light chain gene-polyA'; and (ii) a second expression cassette including 'promoter-UTR-intron-ustekinumab heavy chain gene-internal ribosome entry site (IRES)-amplification gene-polyA'. The present invention provides a bicistronic expression vector for antibody expression, including: (i) a first expression cassette including 'promoter-untranslated region (UTR)-intron-ipilimumab light chain gene-polyA'; and (ii) a second expression cassette including 'promoter-UTR-intron-ipilimumab heavy chain gene-internal ribosome entry site (IRES)-amplification gene-polyA'.

As used herein, the term "bicistronic" refers to a system, in which a ribosome can synthesize a polypeptide within mRNA in a eukaryotic cell, thus enabling the synthesis of multiple proteins from a single mRNA. In the present invention, a vector was designed so that an antibody gene and an amplification gene can be expressed simultaneously.

Unlike the prokaryotic cells such as *E. coli* having a polycistronic system, in which multiple proteins can be synthesized simultaneously from a single mRNA by the multiple binding of ribosome to various site of the mRNA, in eukaryotic cells, ribosome binds to the 5' end of an mRNA and looks for a start codon AUG via scanning during the protein translation from the mRNA. Since protein synthesis starts only from this AUG codon, eukaryotic cells have a monocistronic system in which only a single polypeptide can be synthesized from a single mRNA, and Kozac sequence is known to play an important role in the recognition of ATG and initiation of protein synthesis. However, in the case of encephalomyocarditis virus (hereinafter, EMCV), which has an RNA sequence with a specialized structure called internal ribosome entry site (hereinafter, IRES), multiple proteins can be translated from a single mRNA in a eukaryotic cell (Jang, et al., *J. Virol.* (1989) 63, 1651). In the present invention, for the simultaneous expression of an antibody gene and an amplification gene, a vector was designed so that IRES can be positioned downstream of a heavy chain gene of an antibody, followed by the amplification gene.

As used herein, the term "vector" refers to a gene construct including essential regulatory factors such as a promoter for expressing a target gene in an appropriate host cell, and preferably, for the purpose of the present invention, the vector refers to one for expressing an antibody, and it may be a bicistronic expression vector.

In an exemplary embodiment, the vector of the present invention may be a bicistronic expression vector for expressing bevacizumab, including: (i) a first expression cassette including 'promoter-untranslated region (UTR)-intron-bevacizumab light chain gene-polyA'; and (ii) a second expression cassette including 'promoter-UTR-intron-bevacizumab heavy chain gene-internal ribosome entry site (IRES)-amplification gene-polyA'.

In another exemplary embodiment, the vector of the present invention may be a bicistronic expression vector for expressing tocilizumab, including: (i) a first expression cassette including 'promoter-untranslated region (UTR)-intron-tocilizumab light chain gene-polyA'; and (ii) a second expression cassette including 'promoter-UTR-intron-tocilizumab heavy chain gene-internal ribosome entry site (IRES)-amplification gene-polyA'.

In still another exemplary embodiment, the vector of the present invention may be a bicistronic expression vector for expressing denosumab, including: (i) a first expression cassette including 'promoter-untranslated region (UTR)-intron-denosumab light chain gene-polyA'; and (ii) a second expression cassette including 'promoter-UTR-intron-denosumab heavy chain gene-internal ribosome entry site (IRES)-amplification gene-polyA'.

In still another exemplary embodiment, the vector of the present invention may be a bicistronic expression vector for expressing golimumab, including: (i) a first expression cassette including 'promoter-untranslated region (UTR)-intron-golimumab light chain gene-polyA'; and (ii) a second expression cassette including 'promoter-UTR-intron-golimumab heavy chain gene-internal ribosome entry site (IRES)-amplification gene-polyA'.

In still another exemplary embodiment, the vector of the present invention may be a bicistronic expression vector for expressing belimumab, including: (i) a first expression cassette including 'promoter-untranslated region (UTR)-intron-belimumab light chain gene-polyA'; and (ii) a second expression cassette including 'promoter-UTR-intron-belimumab heavy chain gene-internal ribosome entry site (IRES)-amplification gene-polyA'.

In still another exemplary embodiment, the vector of the present invention may be a bicistronic expression vector for expressing ustekinumab, including: (i) a first expression cassette including 'promoter-untranslated region (UTR)-intron-ustekinumab light chain gene-polyA'; and (ii) a second expression cassette including 'promoter-UTR-intron-ustekinumab heavy chain gene-internal ribosome entry site (IRES)-amplification gene-polyA'.

In still another exemplary embodiment, the vector of the present invention may be a bicistronic expression vector for expressing ipilimumab, including: (i) a first expression cassette including 'promoter-untranslated region (UTR)-intron-ipilimumab light chain gene-polyA'; and (ii) a second expression cassette including 'promoter-UTR-intron-ipilimumab heavy chain gene-internal ribosome entry site (IRES)-amplification gene-polyA'.

As used herein, the term "promoter" refers to an area of DNA nucleotide sequence to which transcription regulatory factors bind, and for the purpose of the present invention, a promoter capable of inducing a powerful and stable gene expression may be used to increase the efficiency of gene expression.

The promoter may preferably be one selected from the group consisting of simian virus 40 (SV40) early promoter, cytomegalovirus (CMV) promoter, and elongation factor1-α (EF1-α) promoter, although not limited thereto. In particular, the EF1-α may be human elongation factor1-α (hEF1-α). More preferably, the promoter may be a CMV promoter, and most preferably, the promoter of cytomegalovirus strain AD169. In an exemplary embodiment of the present invention, an expression vector was constructed by inserting the CMV promoter, which is one of the strongest promoters known so far on the sequence of the cytomegalovirus strain AD169 genome (GenBank: X17403.1), for inducing high antibody expression.

As used herein, the term "untranslated region (UTR)", which is an untranslated region of mRNA, generally refers to both ends of a coding region. Specifically, the 5' end portion is called 5' UTR and the 3' end is called 3'UTR. More specifically, as used herein, the UTR is included in the bicistronic vector of the present invention and is not particularly limited as long as it has the effect of increasing the amount of gene expression. Even more specifically, the UTR may be a UTR derived from CMV. The present inventors first verified that the bicistronic expression vector, which includes an expression cassette containing both the UTR and an intron simultaneously, can increase the expression level of a gene incorporated into the vector, and thus the present invention is directed to providing a novel antibody expression vector.

The UTR of the present invention may preferably be the UTR of the cytomegalovirus strain AD169 of SEQ ID NO: 2, although not limited thereto. In an exemplary embodiment of the present invention, an expression vector was constructed using the UTR on the sequence of the cytomegalovirus strain AD169 genome (GenBank: X17403.1) for stronger gene expression, by inserting the UTR between the promoter and the antibody gene for light and heavy chains, respectively.

As used herein, the term "intron" refers to a characteristic sequence in a DNA region found in eukaryotic cells which does not encode a protein due to lack of genetic information. Intron is transcribed during mRNA synthesis by RNA polymerase in a nucleus and excised from the mRNA sequence via splicing while being transported out of the nucleus. More and more study results have been accumulated to support that a plasmid can have a higher gene expression level when it includes an intron and an untranslated exon. As a result, more improved vectors capable of stable and constitutive gene expression have been developed for use by introducing a heterologous intron into a recombinant expression vector. However, the intron insertion had been applied to monocistronic vectors, and thus only one gene could be expressed by the vector. In order to overcome the limitation, the present inventors have endeavored to insert a foreign intron gene into a bicistronic vector system in a position downstream of a promoter for inducing gene expression with high efficiency. In particular, the intron of the present invention may be an intron derived from CMV.

The intron of the present invention may preferably be the UTR of cytomegalovirus strain AD169 of SEQ ID NO: 3, although not limited thereto. In an exemplary embodiment of the present invention, an expression vector was constructed using the UTR on the sequence of the cytomegalovirus strain AD169 genome (GenBank: X17403.1) for stronger gene expression, by inserting the UTR between the promoter and the antibody gene for light and heavy chains, respectively.

The promoter, the UTR, and the intron included in the expression vector of the present invention may have the same or different origin. For example, the promoter may be SV40 early promoter and the UTR and the intron may be derived from SV40; the promoter may be CMV promoter and the UTR and the intron may be derived from CMV; and the promoter may be hEF1-α promoter and the UTR and the intron may be derived from hEF1-α.

As used herein, the term "amplification gene" refers to a gene that is amplified for inducing the gene to be co-expressed along with a desired antibody gene, which is to be expressed with stability and high efficiency, in the present invention. An amplification gene can be amplified using a chemical based on the principle that cells without the incorporated amplification gene cannot grow in the presence of the chemical, thereby allowing the growth of only those having both the amplification gene and the antibody gene incorporated into their chromosomes. The bicistronic expression vector of the present invention can induce the amplification gene and the antibody gene to be co-expressed as if they were a single gene, thereby allowing high expression of the target antibody gene.

The amplification gene may preferably be glutamine synthetase (GS) or dihydrofolate reductase (DHFR), but is not limited thereto. In an exemplary embodiment of the present invention, the pCYB204IG expression vector including GS as an amplification gene and the pCYB204ID expression vector including DHFR as an amplification gene, (FIGS. 5 and 6) were constructed, and it was confirmed that the expression vectors pCYBBSS001 (FIG. 8), pCYBBSS002 (FIG. 9), pCYBBSS003 (FIG. 10), pCYBBSS004 (FIG. 11), pCYBBSS005 (FIG. 12), and pCYBBSS006 (FIG. 13) are useful for high-level expression of an antibody gene.

As used herein, the term "antibody" refers to a material, which is produced by an antigenic stimulus in an immune system and specifically binds to a particular antigen and circulates freely in the bloodstream and the lymph thereby causing antigen-antibody interactions. For the purpose of the present invention, the antibody is to be constitutively expressed at high level. The expression vector of the present invention can induce a strong and stable expression of the antibody gene, and the antibody can be efficiently produced using an animal cell transfected with the expression vector.

The antibody is a protein consisting of amino acids and a sugar chain, and forms a Y-shaped protein by disulfide bonds between two light chains and two heavy chains. In an exemplary embodiment of the present invention, an expression vector capable of producing an antibody having both light and heavy chains were constructed, by constructing a vector, which includes an antibody light chain-expressing cassette with a UTR and an intron, and an antibody heavy chain-expressing cassette with a UTR and an intron.

The antibody of the present invention may preferably be any therapeutic antibody conventionally used in the art, although not limited thereto. For example, the antibody may be one selected from the group consisting of bevacizumab, an antibody targeting vascular endothelial Growth Factor-A (VEGF-A); tocilizumab, an antibody targeting IL-6 receptors; denosumab, an antibody targeting receptor activator of NF-kB ligand (RANKL); belimumab, an antibody targeting B lymphocyte stimulator (BLyS); golimumab, an antibody targeting TNFα; ustekinumab, an antibody targeting interleukin-12 (IL-12) and interleukin-23 (IL-23); and ipilimumab, an antibody targeting cytotoxic T lymphocyte Antigen-4.

Bevacizumab, also called Avastin, is a humanized antibody which is known as a antibody therapeutic for the treatment of colorectal cancer, lung cancer, kidney cancer, and brain cancer, developed by Genentech (USA). In an exemplary embodiment of the present invention, it was confirmed that the introduction of bevacizumab, the representative antibody therapeutic, into the bicistronic expression vector for antibody expression of the present invention effectively produced the antibody.

Tocilizumab is a human monoclonal antibody developed by Chugai, which is a Japanese subsidiary of Roche (a Swiss pharmaceutical company), and has been approved as a treatment for rheumatoid arthritis in USA, Europe, and Japan under the product name of Actemra. In an exemplary embodiment of the present invention, it was confirmed that the introduction of tocilizumab into the bicistronic expression vector for antibody expression of the present invention effectively produced the antibody. As a result, it was confirmed that the bicistronic expression vector of the present invention is a system capable of high-level expression of the antibody, tocilizumab.

Denosumab is a human monoclonal antibody developed by Amgen (USA), which has been approved as a treatment for osteoporosis in USA, Canada, and Europe, under the product name of Prolia, and has also been approved in Europe as a drug for the prevention of fracture in patients with bone metastasis from solid cancer under the product name of Xgeva. In an exemplary embodiment of the present invention, it was confirmed that the introduction of denosumab into the bicistronic expression vector for antibody expression of the present invention effectively produced the antibody. As a result, it was confirmed that the bicistronic expression vector of the present invention is a system capable of high-level expression of the antibody, denosumab.

Belimumab is a human monoclonal antibody developed by for B lymphocyte stimulator (BLyS) developed by GlaxoSmithKline (GSK), a multinational pharmaceutical company, and has been approved in USA, Canada, and Europe as a treatment for lupus (systemic lupus erythematosus, SLE). In an exemplary embodiment of the present invention, it was confirmed that the introduction of belimumab into the bicistronic expression vector for antibody expression of the present invention effectively produced the antibody. As a result, it was confirmed that the bicistronic expression vector of the present invention is a system capable of high-level expression of the antibody, belimumab.

Golimumab is a human monoclonal antibody developed by Janssen Biotech, Inc., (formerly Centocor), a subsidiary of Johnson & Johnson, a global pharmaceutical company, and has been approved in USA, Canada, and Korea as a treatment for rheumatoid arthritis, psoriatic arthritis, and ankylosing spondylitis under the product name of Simponi. In an exemplary embodiment of the present invention, it was confirmed that the introduction of golimumab into the bicistronic expression vector for antibody expression of the present invention effectively produced the antibody. As a result, it was confirmed that the bicistronic expression vector of the present invention is a system capable of high-level expression of the antibody, golimumab.

Uustekinumab is a human monoclonal antibody for interleukin-12 (IL-12) and interleukin-23 (IL-23) developed by Janssen Pharmaceuticals, Inc., a multinational pharmaceutical company, and has been approved by the U.S. Food and Drug Administration (FDA) as a treatment for psoriatic arthritis, and the drug is in clinical trials for the treatment of severe psoriasis, moderate-to-severe plaque psoriasis, multiple sclerosis, sarcoidosis, etc. In an exemplary embodiment of the present invention, it was confirmed that the introduction of ustekinumab into the bicistronic expression vector for antibody expression of the present invention effectively produced the antibody. As a result, it was confirmed that the bicistronic expression vector of the present invention is a system capable of high-level expression of the antibody, ustekinumab.

Ipilimumab is a human monoclonal antibody for cytotoxic T-lymphocyte antigen (CTLA-4) developed by Bristol-Myers Squibb Co. (BMS), a U.S. pharmaceutical company, and has been approved by the U.S. Food and Drug Administration (FDA) as a treatment for melanoma and skin cancer under the product name of Yervoy, and the drug is in clinical trials for the treatment of non-small cell lung carcinoma (NSCLC), small cell lung cancer (SCLC), bladder cancer, and metastatic hormone-refractory prostate cancer. In particular, Yervoy, approved as a treatment for melanoma by the FDA, is administered in the form of an intravenous injection, and it exhibits pharmaceutical efficacies by assisting the human immune system to attack the melanoma-forming tumor cells by recognizing them as targets. In an exemplary embodiment of the present invention, it was confirmed that the introduction of ipilimumab into the bicistronic expression vector for antibody expression of the present invention effectively produced the antibody. As a result, it was confirmed that the bicistronic expression vector of the present invention is a system capable of high-level expression of the antibody, ipilimumab.

As used herein, the term "antibody light chain gene" refers to a gene encoding the light chain region in an antibody, which is a Y-shaped protein linked by amino acids and sugar chains between two light chains and two heavy chains. In the present invention, the antibody light chain gene may include without limitation any light chain gene for any antibody, in which the expression level can be increased using the bicistronic vector of the present invention, and for example, the light chain gene may be a nucleotide sequence encoding the light chain region of antibody therapeutics, i.e., bevacizumab, tocilizumab, denosumab, belimumab, golimumab, ustekinumab, or ipilimumab.

Specifically, the antibody light chain gene may be one consisting of a nucleotide sequence encoding an amino acid selected from the group consisting of SEQ ID NO: 13 for the light chain region of bevacizumab; SEQ ID NO: 17 for the light chain region of tocilizumab; SEQ ID NO: 21 for the light chain region of denosumab; SEQ ID NO: 25 for the light chain region of belimumab; SEQ ID NO: 29 for the light chain region of golimumab; SEQ ID NO: 33 for the light chain region of ustekinumab; and SEQ ID NO: 37 for the light chain region of ipilimumab. More specifically, the antibody light chain gene may be one consisting of a nucleotide sequence selected from the group consisting of SEQ ID NO: 11 encoding the light chain region of bevacizumab; SEQ ID NO: 15 encoding the light chain region of tocilizumab; SEQ ID NO: 19 encoding the light chain region of denosumab; SEQ ID NO: 23 encoding the light chain region of belimumab; SEQ ID NO: 27 encoding the light chain region of golimumab; SEQ ID NO: 31 encoding the light chain region of ustekinumab; and SEQ ID NO: 35 encoding the light chain region of ipilimumab.

As used herein, the term "antibody heavy chain gene" refers to a gene encoding the heavy chain region in an antibody, which is a Y-shaped protein linked by amino acids and sugar chains between two light chains and two heavy chains. In the present invention, the antibody heavy chain gene may include without limitation any heavy chain gene for any antibody, in which the expression level can be increased using the bicistronic vector of the present invention, and for example, the heavy chain gene may be a nucleotide sequence encoding the heavy chain region of antibody therapeutics, i.e., bevacizumab, tocilizumab, denosumab, belimumab, golimumab, ustekinumab, or ipilimumab.

Specifically, the antibody light chain gene may be one consisting of a nucleotide sequence encoding an amino acid selected from the group consisting of SEQ ID NO: 14 for the heavy chain region of bevacizumab; SEQ ID NO: 18 for the heavy chain region of tocilizumab; SEQ ID NO: 22 for the heavy chain region of denosumab; SEQ ID NO: 26 for the heavy chain region of belimumab; SEQ ID NO: 30 for the heavy chain region of golimumab; SEQ ID NO: 34 for the heavy chain region of ustekinumab; and SEQ ID NO: 38 for the heavy chain region of ipilimumab. More specifically, the antibody heavy chain gene may be one consisting of a nucleotide sequence selected from the group consisting of SEQ ID NO: 12 encoding the heavy chain region of bevacizumab; SEQ ID NO: 16 encoding the heavy chain region of tocilizumab; SEQ ID NO: 20 encoding the heavy chain region of denosumab; SEQ ID NO: 24 encoding the heavy chain region of belimumab; SEQ ID NO: 28 encoding the heavy chain region of golimumab; SEQ ID NO: 32 encoding the heavy chain region of ustekinumab; and SEQ ID NO: 36 encoding the heavy chain region of ipilimumab.

As used herein, the term "internal ribosome entry site (IRES), SEQ ID NO: 4)" refers to a particular region present inside of mRNA of a eukaryotic cell, to which ribosome directly binds, thereby capable of synthesizing multiple proteins from a single mRNA. In the present invention, IRES serves to prepare the expression vector of the present invention to be a bicistronic expression vector.

Translation of mRNA in eukaryotic cells is normally dependent on the cap structure at the 5' end of mRNA. However, when translation is independent of the cap structure, ribosome may directly bind to a particular region inside of mRNA and start translation therefrom, which is called an internal initiation site. In the internal initiation site, the ribosome-binding site on mRNA is called IRES, which is found in mRNAs of viruses such as poliovirus and encephalomyocarditis (EMC) virus, and also in cellular mRNAs such as binding immunoglobulin protein (BiP) mRNA and *Drosophila antennapedia* homeobox gene (Antp) mRNA.

As used herein, the term "polyA", which is also called polyadenylic acid or polyadenylic acid fragment, refers to a continuous sequence of adenylic acids that are normally present at the 3' end of mRNA in eukaryotic cells. The length thereof is from 10- to 200 nucleotides and may be controlled variously depending on the allowable size of the backbone of the expression vector. PolyA is known to be involved in stabilization, translation, and transport of mRNA from nucleus to cytoplasm.

Figure 5:
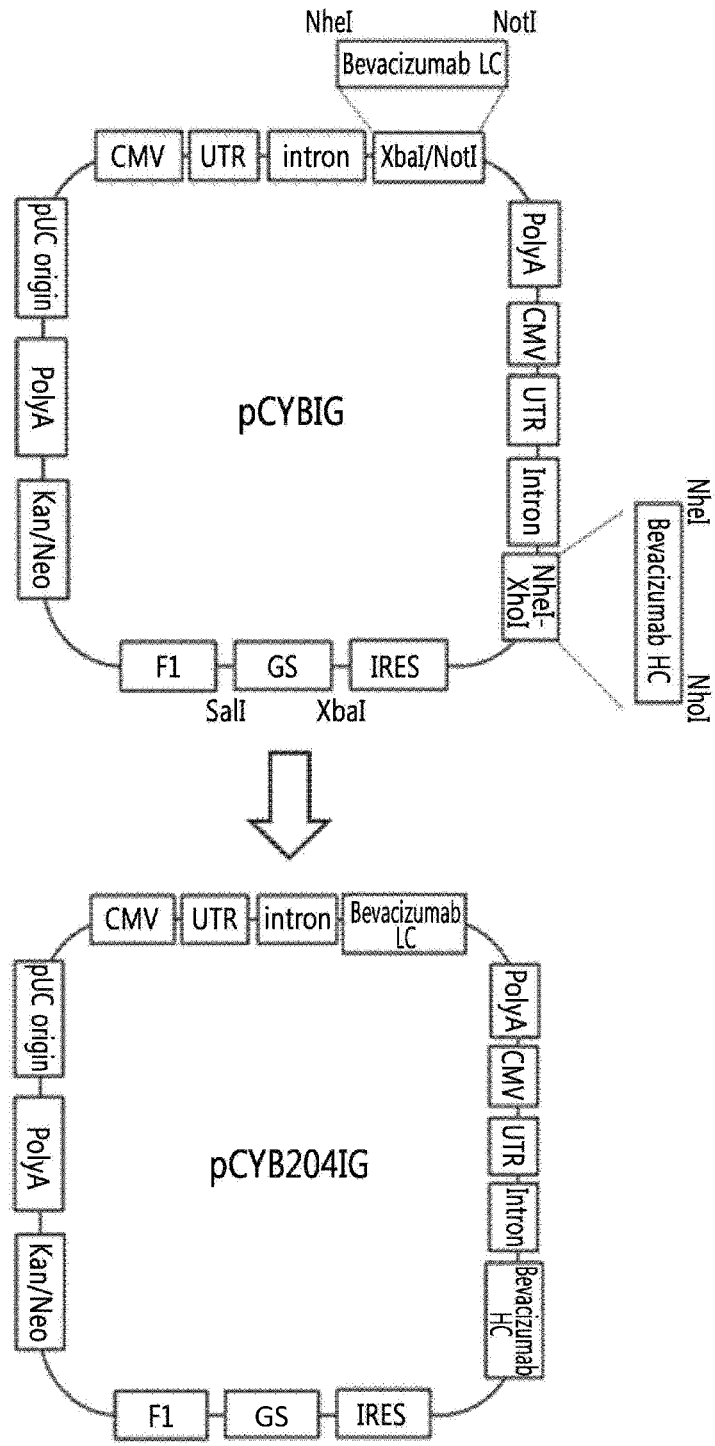
FIG. 5 shows a schematic diagram illustrating the process of constructing the pCYB204IG vector, which is an expression vector for the light chain/heavy chains of bevacizumab containing the GS gene according to the present invention.
Figure 6:
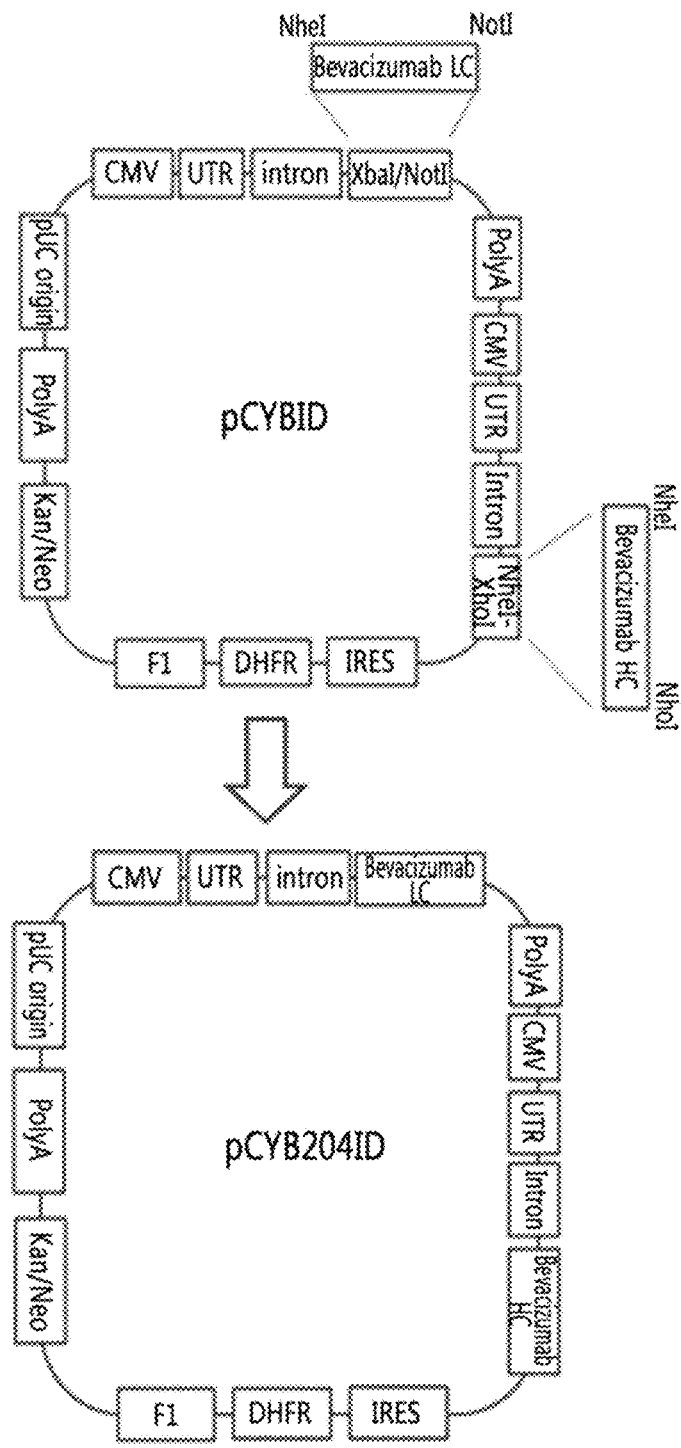
FIG. 6 shows a schematic diagram illustrating the process of constructing the pCYB204ID vector, which is an expression vector for the light chain/heavy chains of bevacizumab containing the DHFR gene according to the present invention.
Figure 8:
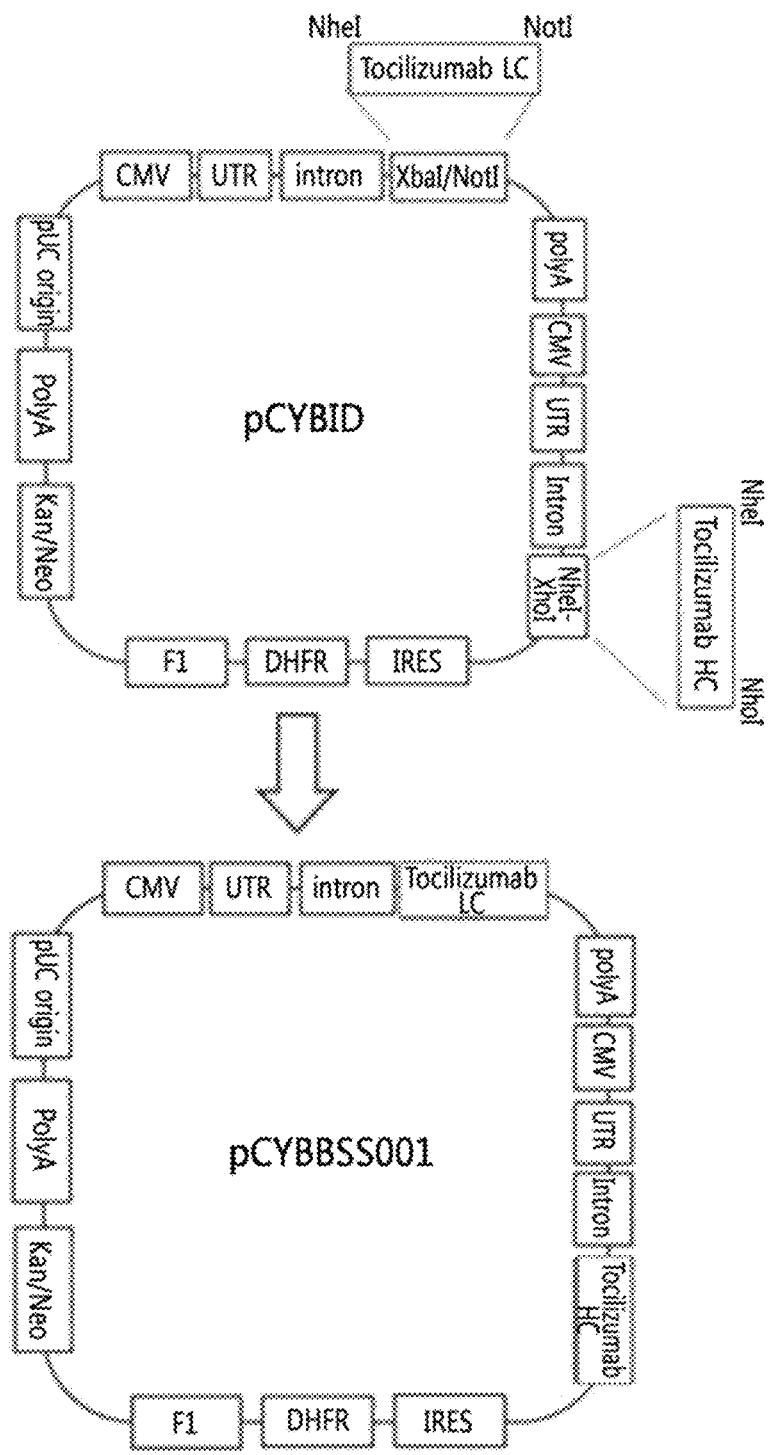
FIG. 8 shows a schematic diagram illustrating the restriction map of the expression vector pCYBBSS001 used in the present invention.
Figure 9:
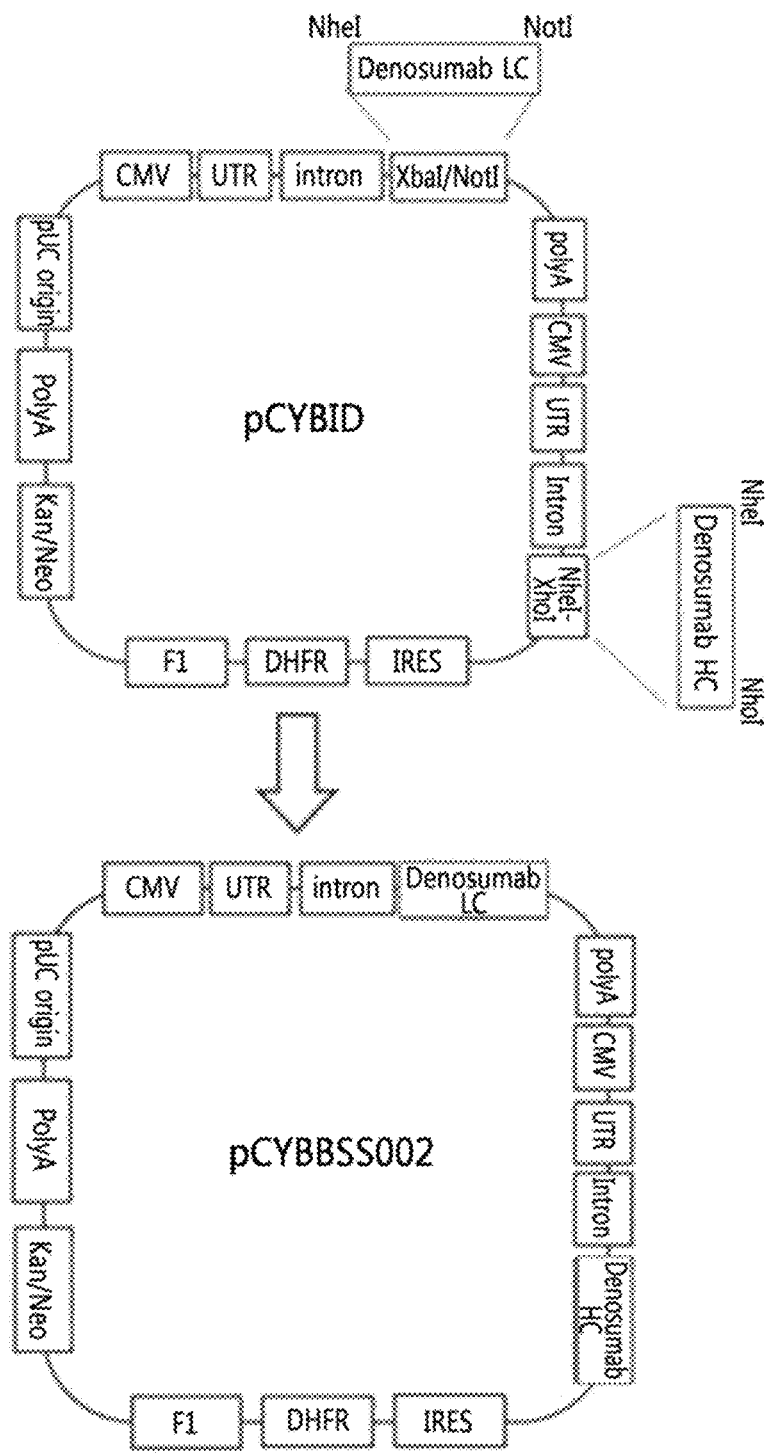
FIG. 9 shows a schematic diagram illustrating the restriction map of the expression vector pCYBBSS002 used in the present invention.
Figure 10:
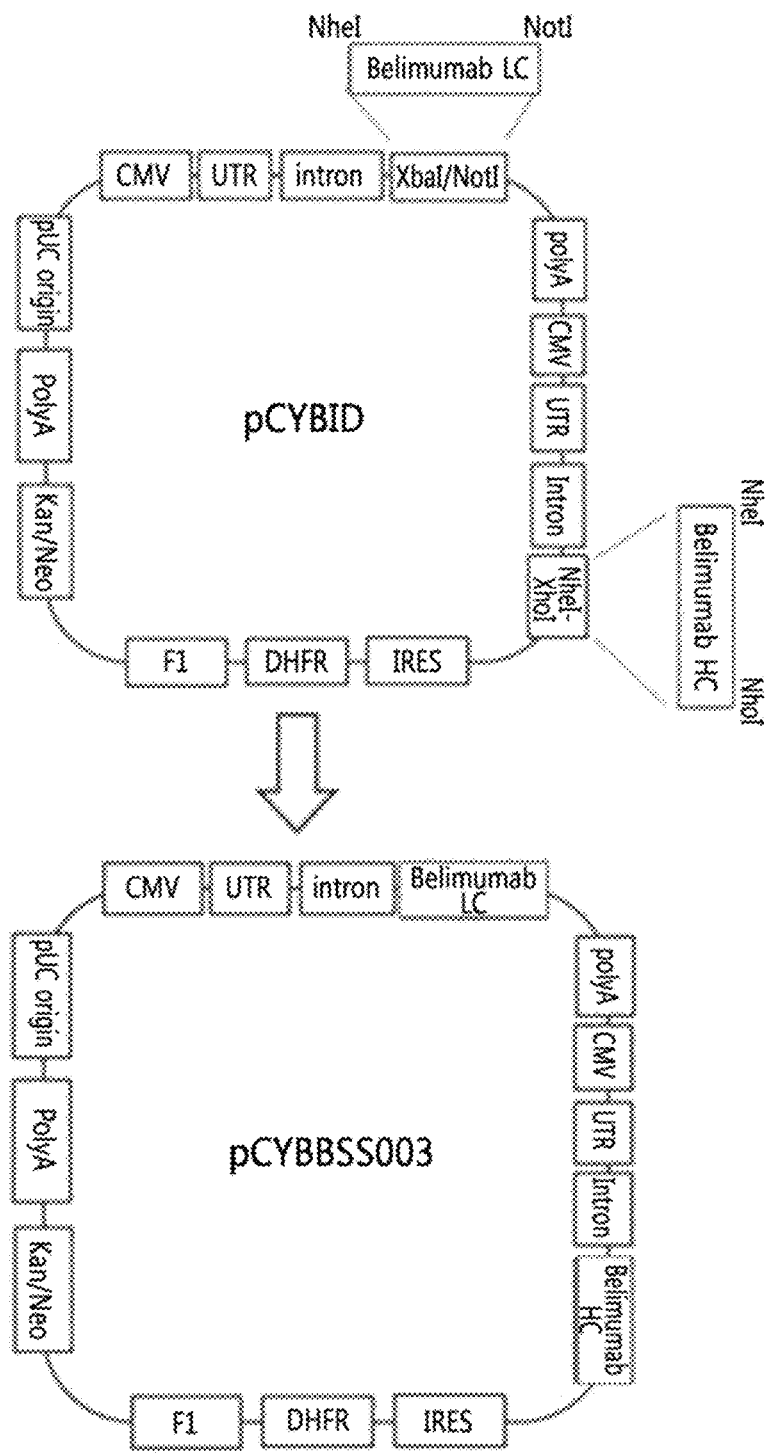
FIG. 10 shows a schematic diagram illustrating the restriction map of the expression vector pCYBBSS003 used in the present invention.
Figure 11:
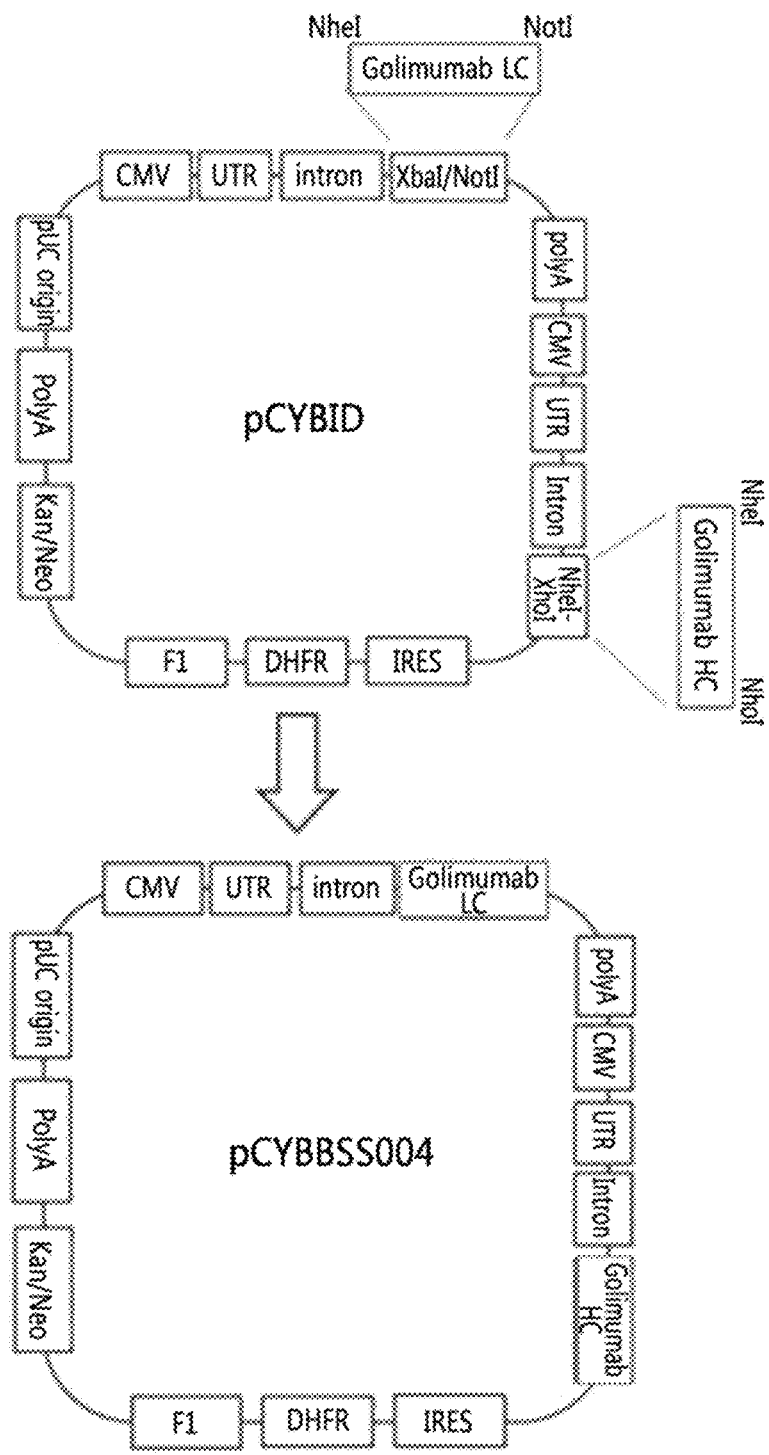
FIG. 11 shows a schematic diagram illustrating the restriction map of the expression vector pCYBBSS004 used in the present invention.
Figure 12:
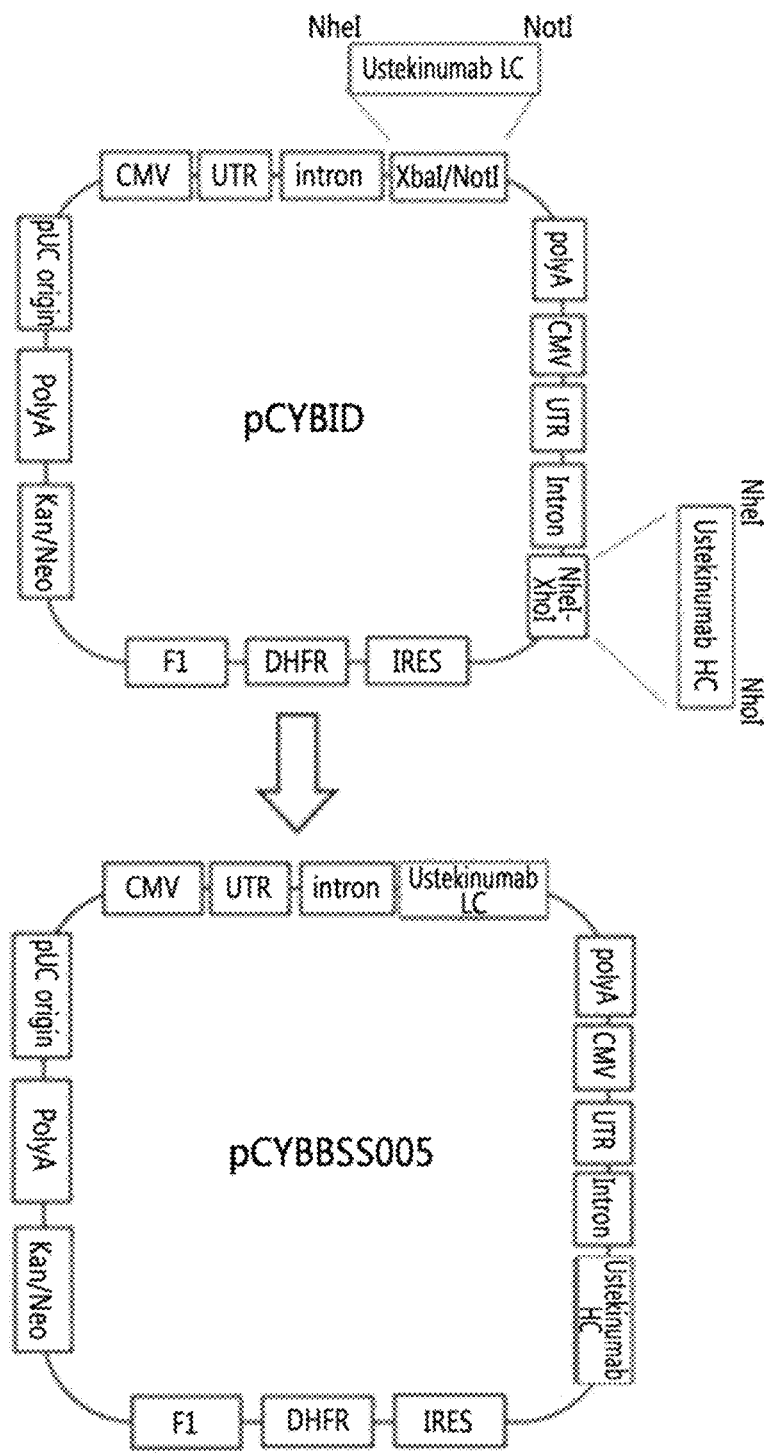
FIG. 12 shows a schematic diagram illustrating the restriction map of the expression vector pCYBBSS005 used in the present invention.
Figure 13:
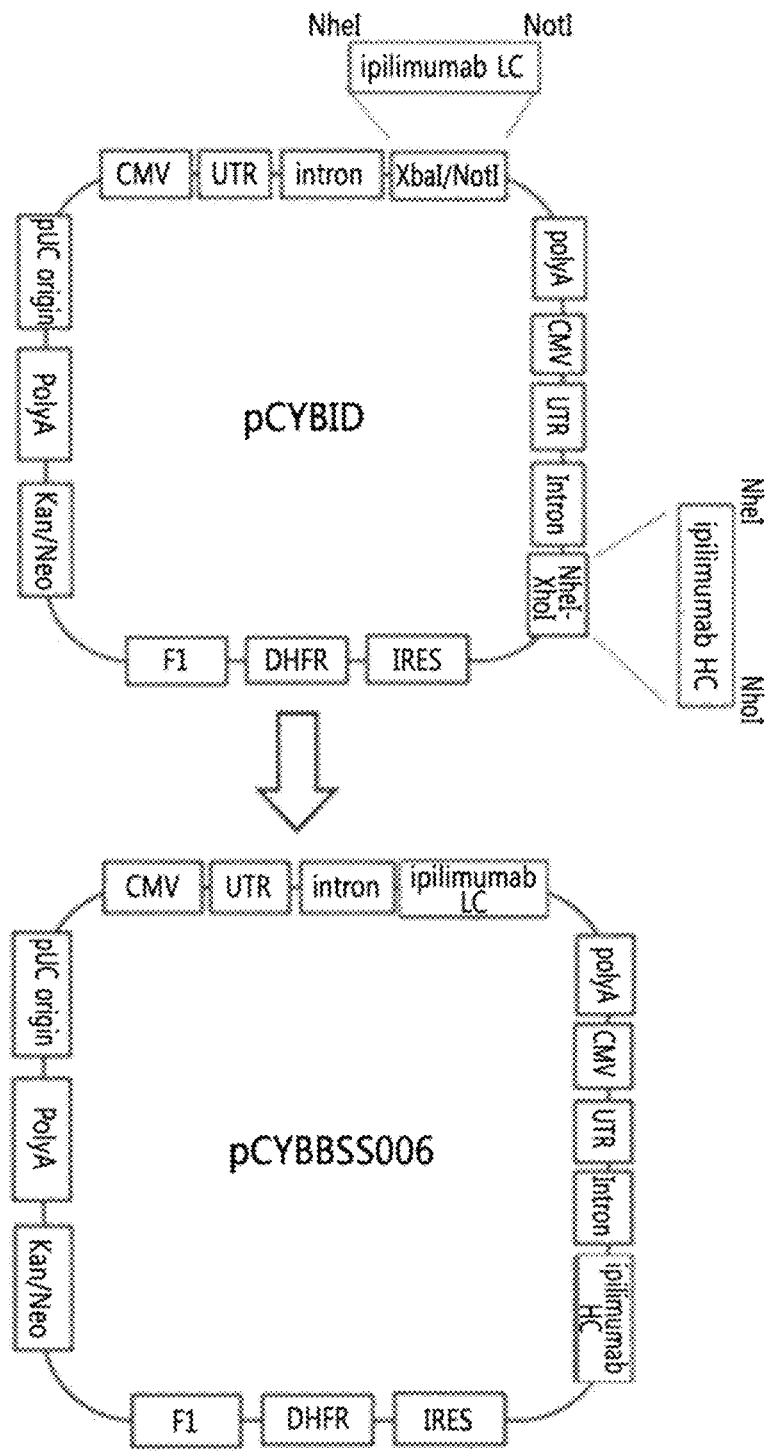
FIG. 13 shows a schematic diagram illustrating the restriction map of the expression vector pCYBBSS006 used in the present invention.

The bicistronic expression vector for antibody production of the present invention may preferably be pCYB204IG illustrated in FIG. 5, pCYB204ID illustrated in FIG. 6, pCYBBSS001 illustrated in FIG. 8, pCYBBSS002 illustrated in FIG. 9, pCYBBSS003 illustrated in FIG. 10, pCYBBSS004 illustrated in FIG. 11, pCYBBSS005 illustrated in FIG. 12, or pCYBBSS006 illustrated in FIG. 13, although not limited thereto.

The pCYB204IG expression vector is an expression vector, which includes a first expression cassette including 'CMV promoter-UTR-intron-bevacizumab light chain gene-polyA', and a second expression cassette including 'CMV promoter-UTR-intron-bevacizumab heavy chain gene-IRES-GS-polyA'. The pCYB204ID expression vector is an expression vector, which includes a first expression cassette including 'CMV promoter-UTR-intron-bevacizumab light chain gene-polyA', and a second expression cassette including 'CMV promoter-UTR-intron-bevacizumab heavy chain gene-IRES-DHFR-polyA'. The pCYBBSS001 expression vector is an expression vector, which includes a first expression cassette including 'CMV promoter-UTR-intron-tocilizumab light chain gene-polyA', and a second expression cassette including 'CMV promoter-UTR-intron-tocilizumab heavy chain gene-IRES-DHFR-polyA'. The pCYBBSS002 expression vector is an expression vector, which includes a first expression cassette including 'CMV promoter-UTR-intron-denosumab light chain gene-polyA', and a second expression cassette including 'CMV promoter-UTR-intron-denosumab heavy chain gene-IRES-DHFR-polyA'. The pCYBBSS003 expression vector is an expression vector, which includes a first expression cassette including 'CMV promoter-UTR-intron-belimumab light chain gene-polyA', and a second expression cassette including 'CMV promoter-UTR-intron-belimumab heavy chain gene-IRES-DHFR-polyA'. The pCYBBSS004 expression vector is an expression vector, which includes a first expression cassette including 'CMV promoter-UTR-intron-golimumab light chain gene-polyA', and a second expression cassette including 'CMV promoter-UTR-intron-golimumab heavy chain gene-IRES-DHFR-polyA'. The pCYBBSS005 expression vector is an expression vector, which includes a first expression cassette including 'CMV promoter-UTR-intron-ustekinumab light chain gene-polyA', and a second expression cassette including 'CMV promoter-UTR-intron-ustekinumab heavy chain gene-IRES-DHFR-polyA'. Additionally, the pCYBBSS006 expression vector is an expression vector, which includes a first expression cassette including 'CMV promoter-UTR-intron-ipilimumab light chain gene-polyA', and a second expression cassette including 'CMV promoter-UTR-intron-ipilimumab heavy chain gene-IRES-DHFR-polyA'.

In an exemplary embodiment of the present invention, the pCYBIG expression vector was constructed using GS as the amplification gene along with a light chain an expression cassette and a heavy chain expression cassette, and the pCYBID expression vector, which includes DHFR instead of GS as the amplification gene, was constructed from the pCYBIG expression vector.

The bicistronic expression vector of the present invention is designed so that the antibody gene for the heavy chain and the light chain can be expressed along with the amplification gene as if they were a single gene, as described above, and thus the expression vector can be used for expressing the antibody with stability and high efficiency.

In an exemplary embodiment, the present invention provides an animal cell transfected with the expression vector.

In the present invention, the expression vector transfected into the animal cell is a bicistronic expression vector for antibody expression, as explained above.

As used herein, the term "transfection" refers to genetic alteration of a cell by direct insertion of DNA into a cultured animal cell, and generally the target gene is inserted into a carrier such as a plasmid to be introduced into the cell. The transfection may be performed according to a conventional method known in the art. Preferably, examples of the transfection method may include calcium phosphate co-precipitation, DEAE-dextran, electroporation, and redistribution (a method for fusing an artificial membrane called ribosome with a cell for preparing a DNA complex). In an exemplary embodiment of the present invention, animal cells were transfected with a light chain/heavy chain expression vector using lipofectamine.

The animal cell may be any type of animal cells used in the art without limitation as long as they are capable of producing an antibody, and preferably the animal cell may be a Chinese hamster ovary (CHO) cell.

In an exemplary embodiment of the present invention, pCYB204IG and pCYB204GS bicistronic vectors for the expression of antibody bevacizumab were constructed by inserting the light and heavy chain genes of bevacizumab into a vector, in which the amplification gene varied to be either GS or DHFR. Upon examining the amount of the expression of antibody bevacizumab in each cell line transfected with the above two vectors, the cell line transfected with the pCYB204ID vector showed at least a 2-fold higher expression of bevacizumab than the cell line transfected with the pCYB204IG vector.

Additionally, in an exemplary embodiment of the present invention, pCYBBSS001 bicistronic vector for the expression of antibody tocilizumab was constructed by inserting the light and heavy chain genes of tocilizumab into a vector, which includes DHFR as the amplification gene. Upon examination of the amount of the expression of antibody tocilizumab in the cell line transfected with the pCYBBSS001 bicistronic vector, high expression of 50.8 µg/mL and 51.7 µg/mL were confirmed under the gene amplification condition with 800 nM methotrexate (MTX).

In an exemplary embodiment of the present invention, pCYBBSS002 bicistronic vector for the expression of antibody denosumab was constructed by inserting the light and heavy chain genes of denosumab into a vector, which includes DHFR as the amplification gene. Upon examination of the amount of the expression of antibody denosumab in the cell line transfected with the pCYBBSS002 bicistronic vector, high expression of 81.4 µg/mL was confirmed under the gene amplification condition with 800 nM MTX.

In an exemplary embodiment of the present invention, pCYBBSS003 bicistronic vector for the expression of antibody belimumab was constructed by inserting the light and heavy chain genes of belimumab into a vector, which includes DHFR as the amplification gene. Upon examination of the amount of the expression of antibody belimumab in the cell line transfected with the pCYBBSS003 bicistronic vector, high expression of 4 µg/mL was confirmed.

In an exemplary embodiment of the present invention, pCYBBSS004 bicistronic vector for the expression of antibody golimumab was constructed by inserting the light and heavy chain genes of golimumab into a vector, which includes DHFR as the amplification gene. Upon examination of the amount of the expression of antibody golimumab in the cell line transfected with the pCYBBSS004 bicistronic vector, high expression of 120.3 µg/mL was confirmed under the gene amplification condition with 500 nM MTX.

In an exemplary embodiment of the present invention, pCYBBSS005 bicistronic vector for the expression of antibody ustekinumab was constructed by inserting the light and heavy chain genes of ustekinumab into a vector, which includes DHFR as the amplification gene. Upon examination of the amount of the expression of antibody ustekinumab in the cell line transfected with the pCYBBSS005 bicistronic vector, high expression of 2.5 µg/mL was confirmed.

Additionally, in an exemplary embodiment of the present invention, pCYBBSS006 bicistronic vector for the expression of antibody ipilimumab was constructed by inserting the light and heavy chain genes of ipilimumab into a vector, which includes DHFR as the amplification gene. Upon examination of the amount of the expression of antibody ipilimumab in the cell line transfected with the pCYBBSS006 bicistronic vector, high expression of 8 µg/mL was confirmed under the gene amplification condition with 500 nM MTX.

In summary, as explained above, the amount of antibody expression was measured by applying the bicistronic expression vector for antibody expression of the present invention to various antibody therapeutics, and as a result, it was confirmed that the expression vector of the present invention improved the expression capability of various antibodies.

In another aspect, the present invention provides a method for producing an antibody, including culturing the animal cell.

The animal cell of the present invention is the one transfected with a bicistronic expression vector including an intron according to the present invention, as described above.

The method for producing antibody of the present invention can produce an antibody with stability and high efficiency. The method may further include purifying the antibody from the culture product in which the animal cell was cultured.

The antibodies that can be produced according to the present invention are the same as described above, and they may be bevacizumab, tocilizumab, denosumab, belimumab, golimumab, ustekinumab, or ipilimumab, although not limited thereto.

DETAILED DESCRIPTION

Hereinafter, the present invention will be described in more detail with reference to the following Examples. However, these Examples are for illustrative purposes only, and the invention is not intended to be limited by these Examples.

Example 1

Construction of Gln-LC, a Gene Set for the Expression of Light Chain

The DNA sequence of a CMV promoter, which includes the UTR and an intron, was obtained based on the nucleotide sequence of the complete genome (GenBank: X17403.1) of human cytomegalovirus strain AD169. Since a promoter, a cloning site, and a poly A element are required at least for the expression of the target protein, the DNAs for the CMV promoter, the UTR, the intron, the cloning site, and the SV40 poly A were synthesized by requesting to Genotech (Korea).

Additionally, XbaI and NotI restriction sites were inserted between the intron and the poly A for the cloning of the light chain of the antibody protein, respectively; an AscI restriction site was inserted at the 5' end of the CMV promoter; and BamHI and XhoI restriction sites were inserted at the 3' end to be used for the subsequent cloning process.

Through the process described above, a gene set Gln-LC having the constitution of [AscI]-CMVpromoter-UTR-intron-[XbaI/NotI]-polyA-[BamHI/XhoI] for the expression of the light chain was constructed (FIG. 1).

Example 2

Construction of Gln-HC, a Gene Set for the Expression of Heavy Chain

PCR was performed using the Gln-LC gene set constructed in Example 1 as a template along with the BamHI Gln-F primer (SEQ ID NO: 7) and the NheI Gln-R primer (SEQ ID NO: 8) summarized in Table 1 below.

TABLE 1

| Primer | Nucleotide Sequence | SEQ ID NO |
|---|---|---|
| BamHI Gln-F | GGC CGG ATC CGG CGC GCC TGC AGT GAA T | 7 |
| NheI Gln-R | GGC CCT CGA GAA AGA TCT GGG CTA GCC GTG TCA AGG ACG GTG ACT GCA G | 8 |

In the gene set Gln-HC for the expression of a heavy chain, a BamHI restriction site was inserted at the 3' end of the CMV promoter, and NheI and XhoI restriction sites were inserted downstream of the CMV promoter for the cloning of the UTR, the intron, and the heavy chain region of the antibody protein to be used for the subsequent cloning process.

PCR was performed by denaturation at 94° C. for 5 min; 30 cycles consisting of denaturation at 94° C. for 50 s, annealing at 50° C. for 30 s, and extension at 72° C. for 2 m; and polymerization at 72° C. for 7 m. The PCR reaction solution contained 25 μL of Premix Taq (Ex Taq version) (TAKARA Co., Ltd.), 2 μL each of SEQ ID NOS: 7 and 8 (10 μmole/μL), and added with distilled water to a final volume of 50 μL.

Through the process described above, a gene set Gln-HC having the constitution of [BamHI]-CMV promoter-UTR-intron-[NheI/XhoI]-[NheI] for the expression of the heavy chain was prepared (FIG. 1).

The Gln-HC gene amplified by PCR was inserted into the pGEM T-easy vector (Promega Corporation) according to the manufacturer's manual.

Example 3

Construction of GS-Gln-LC Plasmid Via GS Vector of a Gene Set for the Expression of a Light Chain For the construction of an expression vector containing a glutamine synthetase (GS) as an amplification gene, the IRES-GS vector developed by the company of the present inventors was used. The IRES-GS vector containing the IRES, the GS gene, and poly A was treated with MluI and XhoI at 37° C. for 4 hours, and the DNA fragment containing the IRES-GS gene-f1 origin-Kanamycin/neomycin resistant gene resistant gene-Poly A-pUC origin was recovered.

Meanwhile, the gene set for the expression of a light chain, Gln-LC, constructed in Example 1 was cleaved by digesting with AscI and XhoI.

Figure 2:
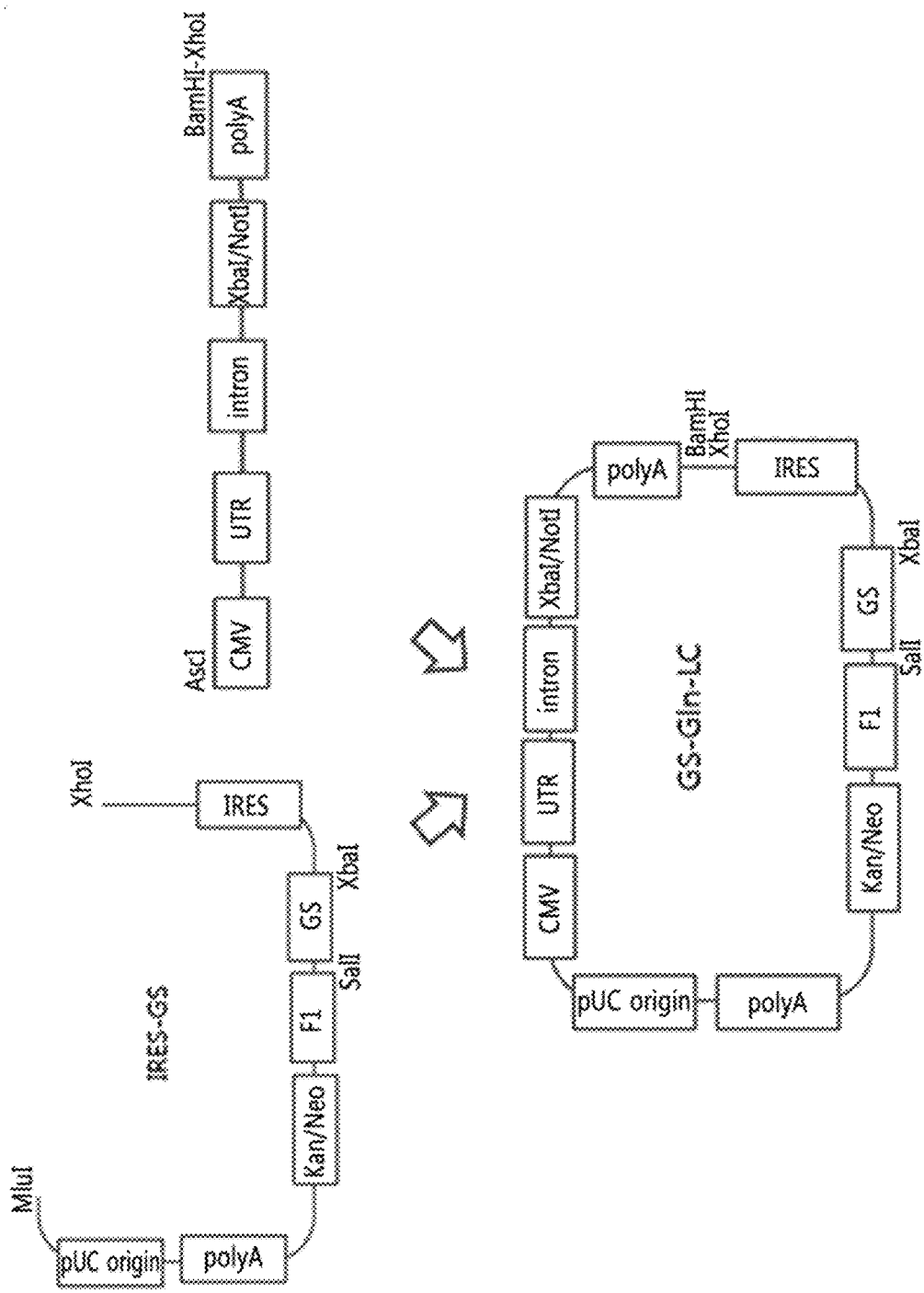
FIG. 2 shows a schematic diagram illustrating the process of constructing the GS-Gln-LC according to the present invention.

The cleaved IRES-GS vector fragment and the Gln-LC gene set fragment were respectively subjected to 1% agarose gel electrophoresis and recovered by gel extraction. The recovered DNA fragments were linked to construct a GS-Gln-LC plasmid (FIG. 2).

Example 4

Construction of pCYBIG, a Plasmid for the Expression of Light Chain and Heavy Chain To obtain the DNA of the Gln-HC, a gene set for the expression of a light chain inserted into the T-easy vector constructed in Example 2, the constructed vector was cleaved by treating with BamHI and XhoI at 37° C. for 4 hours. The treated DNA was subjected to 1% agaroge gel electrophoresis and the DNA fragment corresponding to the size of the Gln-HC was recovered.

Meanwhile, the GS-Gln-LC plasmid constructed in Example 3 was cleaved by treating with BamHI and XhoI at 37° C. for 4 hours. The DNA treated with the restriction enzymes was subjected to 1% agaroge gel electrophoresis and the DNA fragment corresponding to the size of the GS-Gln-LC plasmid was recovered.

Figure 3:
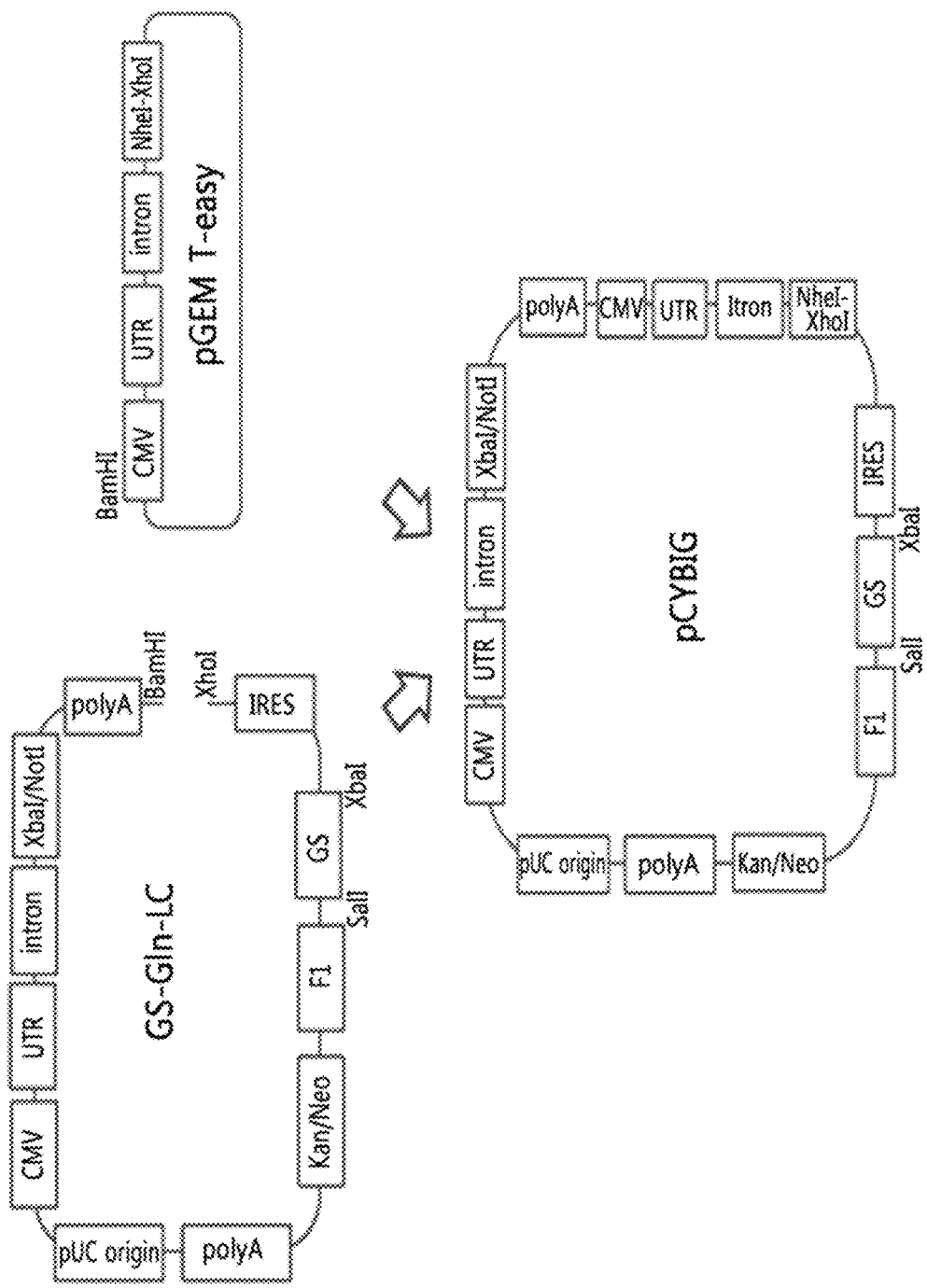
FIG. 3 shows a schematic diagram illustrating the process of constructing the pCYBIG vector containing the GS gene according to the present invention by inserting the Gln-HC to the GS-Gln-LC of the present invention.

The Gln-HC gene set fragment and the GS-Gln-LC plasmid fragment recovered above were linked to construct the pCYBIG vector (FIG. 3).

Example 5

Construction of pCYBID, a Plasmid for the Expression of Light Chain and Heavy Chain The construction of pCYBID vector, in which the GS amplification gene in the pCYBIG vector constructed in Example 4 was substituted with the DHFR gene, was attempted.

Specifically, PCR was performed using the DHFR gene as a template along with the saiI DHFR-F primer (SEQ ID NO: 9) and the NheI DHFR-R primer (SEQ ID NO: 10) summarized in Table 2 below.

TABLE 2

| Primer | Nucleotide Sequence | SEQ ID NO |
|---|---|---|
| SalI DHFR-F | GGC CGT CGA CAT GGT TCG ACC GCT G | 9 |
| NheI DHFR-R | GGC CGC TAG CTT AGC CTT TCT TCT CAT AGA C | 10 |

PCR was performed by denaturation at 94° C. for 5 min; 30 cycles consisting of denaturation at 94° C. for 50 s, annealing at 50° C. for 30 s, and extension at 72° C. for 2 m; and polymerization at 72° C. for 7 m. The PCR reaction solution contained 25 μL of Premix Taq (Ex Taq version)

(TAKARA Co., Ltd.), 2 μL each of SEQ ID NOS: 9 and 10 (10 pmole/μL), and added with distilled water to a final volume of 50 μL. The DHFR gene amplified by PCR as described above was inserted into the pGEM T-easy vector (Promega Corporation) according to the manufacturer's manual.

Meanwhile, the DNA of the pCYBIG vector constructed in Example 4 was cleaved by treating with sail and XbaI and the DNA of the DHFR gene cloned into the T-easy vector was cleaved by treating with sail and NheI.

Figure 4:
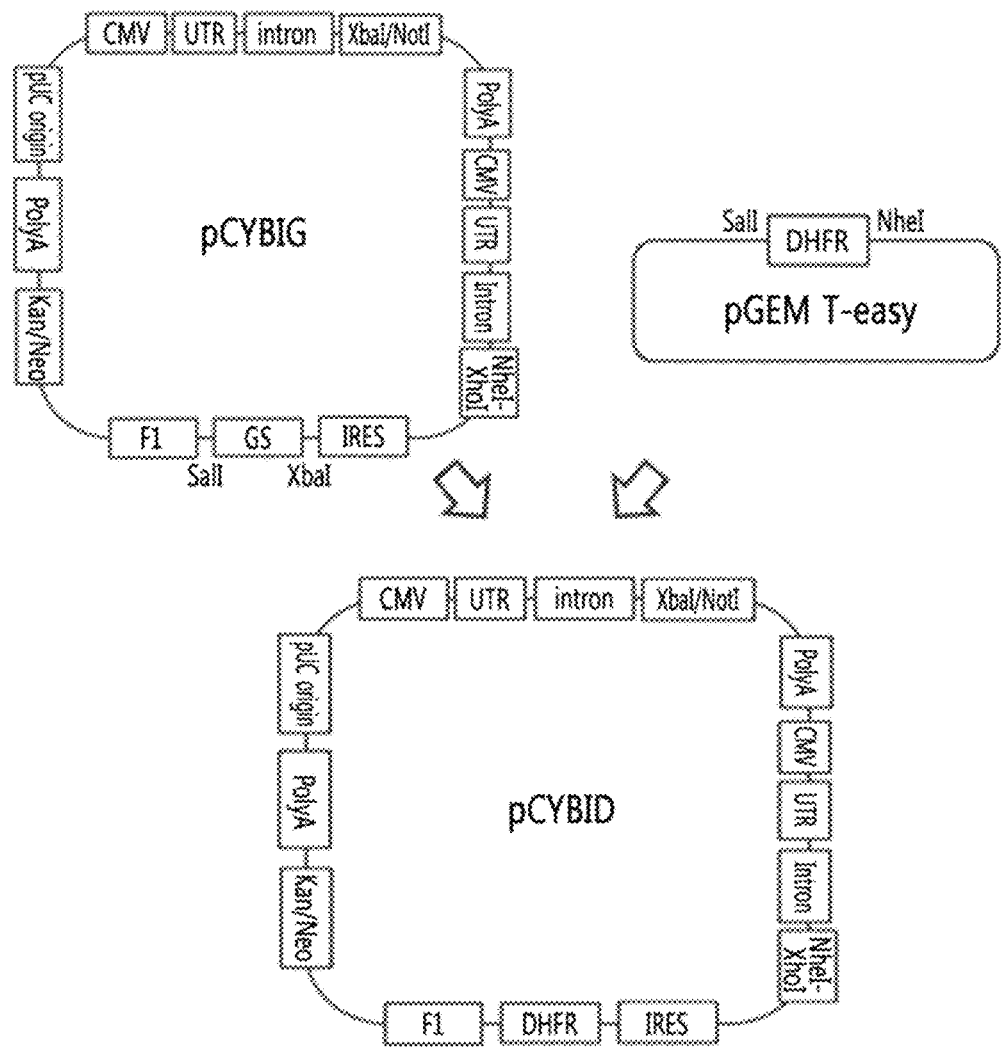
FIG. 4 shows a schematic diagram illustrating the process of constructing the pCYBID vector containing the DHFR gene according to the present invention from the pCYBIG vector of the present invention.

Each of the cleaved DNAs was recovered via 1% agarose gel electrophoresis, and the two DNAs were linked to construct pCYBID vector, in which the GS gene was substituted with the DHFR gene (FIG. 4).

Example 6

Construction of a Plasmid for the Expression of Bevacizumab 6-1. Insertion of a Gene for the Light Chain of Bevacizumab The pCYBIG vector and the pCYBID vector constructed in Examples 4 and 5, respectively, were inserted with the gene for the bevacizumab light chain to construct plasmids for the expression of the bevacizumab light chain.

Specifically, the pCYBIG vector and the pCYBID vector were cleaved with XbaI and NotI.

Regarding the gene for the bevacizumab light chain, the amino acid sequence (SEQ ID NO: 13) of bevacizumab was substituted with a DNA nucleotide sequence (SEQ ID NO: 11).

The substitution of the DNA nucleotide sequence was performed using a DNA nucleotide sequence optimized for CHO cells, which is an antibody-expressing cell line, and NheI and NotI restriction sites were inserted at both 5'- and 3' ends.

The Kozak sequence (GCCACC) was inserted upstream of the start codon, ATG, for inducing the increase of expression level, and SEQ ID NO: 39 'MGWSCIILFL-VATATGVHS' was inserted as a signal sequence for gene synthesis. The thus-synthesized gene was cleaved by treating with NheI and NotI.

Each of the cleaved DNAs was recovered by subjecting to 1% agarose gel electrophoresis, and the two DNAs were linked to construct the pCYBIG vector and the pCYBID vector respectively inserted with the gene for bevacizumab light chain.

6-2. Insertion of a Gene for the Heavy Chain of Bevacizumab

The pCYBIG-bevacizumab light chain gene vector and the pCYBID-bevacizumab light chain gene vector, the vectors constructed in Example 6-1 for the expression of light chain, were cleaved with NheI and XhoI. The amino acid sequence (SEQ ID NO: 14) of bevacizumab was substituted with a DNA nucleotide sequence (SEQ ID NO: 12). Then, the vectors were designed by inserting the Kozak sequence (GCCACC) upstream of the start codon, ATG, as in Example 6-1, and a gene was synthesized by inserting NheI and XhoI restriction sites at both ends, and cleaved by treating with NheI and XhoI. Each of the cleaved DNAs was recovered by subjecting to 1% agarose gel electrophoresis, and the two DNAs were linked to construct vectors in which the light chain and the heavy chain gene of bevacizumab were inserted, respectively (FIGS. 5 and 6).

FIGS. 5 and 6 are schematic diagrams illustrating the pCYB204IG vector and the pCYB204ID vector regarding the method of cloning the light chain and the heavy chain of bevacizumab.

Example 7

Measurement of the Efficiency of Antibody Expression by pCYB204IG Vector 7-1. Transfection For the development of a cell line capable of stably expressing an antibody protein, first, GS-deficient CHO-K1 cells were aliquoted into 6-well plates at a concentration of $4 \times 10^5$ cells the day before the transfection and cultured in a $CO_2$ incubator at 37° C. Upon confirmation of the cell viability of 98% or higher, the pCYB204IG vector was transfected into cells using lipofectamine (Invitrogen Corporation). In particular, the transfection was performed using a medium, which contains 20 μg of the expression vector DNA and 10 μL of lipofectamine in the Opti-MEM-1 (Invitrogen Corporation), and the CHO-K1 cells transfected with the pCYB204IG were selected therefrom.

7-2. Amplification of Antibody Gene

Figure 7A:
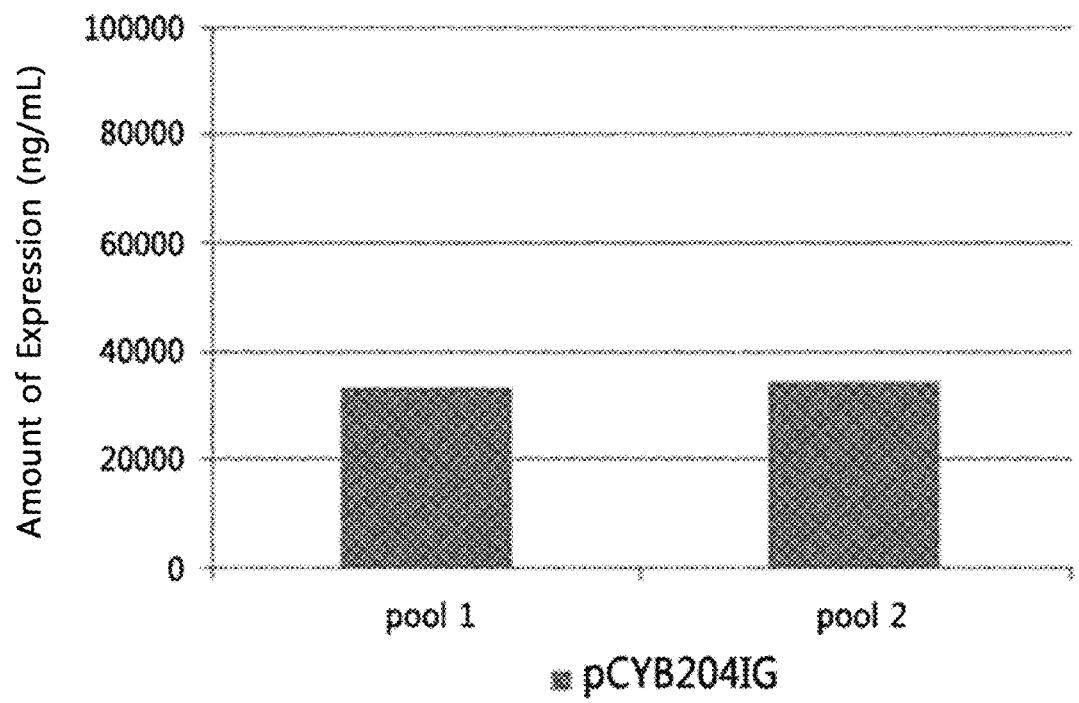
FIG. 7A shows the result of the amount of antibody expression in a cell line transfected with the pCYB204IG at 500 μM MSX.

The CHO-K1 cell line transfected with the pCYB204IG in Example 7-1 was treated with methionine sulfoximine (MSX) at the initial concentration of 25 μM, and the progress of the growth was observed until the cell growth recovered to normal. After the treatment with 25 μM MSX, the MSX concentration for treatment was increased to 250 μM in the subculture after the day 7. In the same manner, the MSX concentration for treatment was finally increased to 500 μM by increasing the MSX concentration at the time-point of subculturing, in which the growth was recovered by the external pressure due to MSX. The expression level of cell line pools (pool 1 and pool 2) prepared at 500 μM MSX were measured. The measurement of the expression level was confirmed via ELISA using anti-Fc (FIG. 7A).

Example 8

Measurement of the Efficiency of Antibody Expression by pCYB204ID Vector 8-1: Transfection For the comparison of expression levels of cell lines transfected with the pCYB204ID expression vector containing, as the amplification gene, the DHFR gene instead of the GS gene of the pCUB204IG vector, the CHO-DG44 cells (Gibco, 12609-012) were transfected with the pCYB204ID, and the transfected CHO-DG44 cells were selected.

8-2: Amplification of Antibody Gene

Figure 7B:
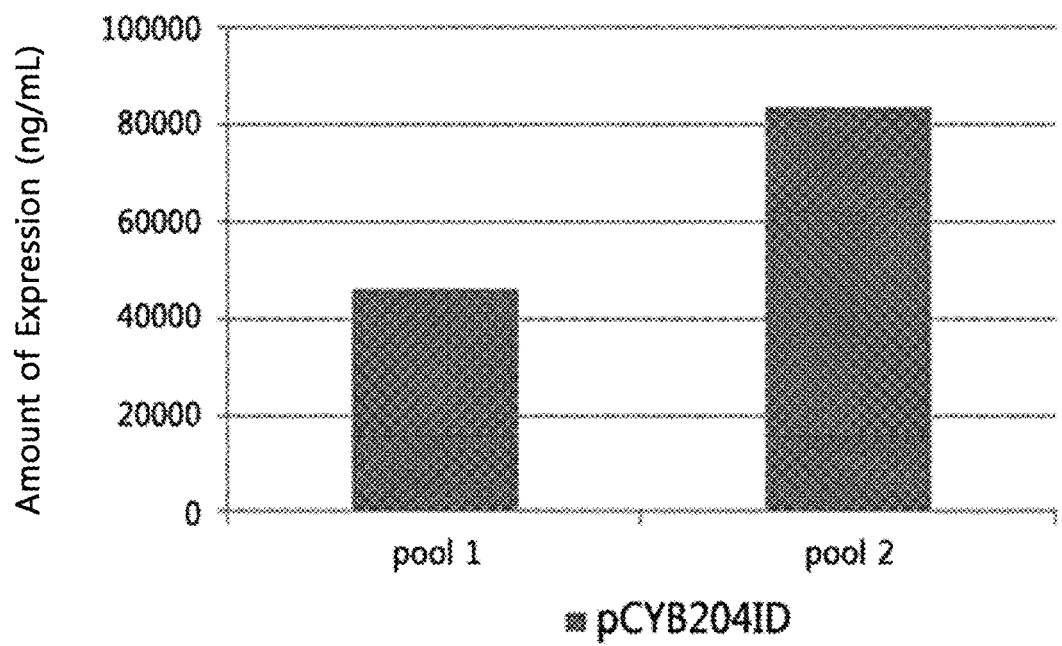
FIG. 7B shows the result of the amount of antibody expression in a cell line transfected with the pCYB204ID at 800 nM MTX.

The CHO-DG44 cell line transfected with the pCYB204ID in Example 8-1 was amplified by treating with methotrexate (MTX). In the same manner as in Example 7-2, the expression level was measured by the method of increasing the MTX concentration when the cell growth was recovered to normal. The MTX concentrations for treatment were 50 nM, 200 nM, and 800 nM. The measurement of the expression level was confirmed via ELISA using anti-Fc (FIG. 7B).

Upon comparison of the expression levels of antibody measured per each vector in Examples 7-2 and 8-2, it was confirmed that the cell line transfected with the pCYB204ID vector had at least 2-fold higher expression than the cell line transfected with the pCYB204IG vector.

Example 9

Construction of a Plasmid for the Expression of Tocilizumab 9-1. Insertion of a Gene for the Light Chain of Tocilizumab The pCYBID vector constructed in Example 5 was inserted with the gene for the tocilizumab light chain to construct a plasmid for the expression of the tocilizumab light chain.

Specifically, the pCYBID vector was cleaved with XbaI and NotI.

The gene for the tocilizumab light chain was substituted with a DNA nucleotide sequence (SEQ ID NO: 15) which encodes the amino acid sequence (SEQ ID NO: 17) of tocilizumab. The substitution of the DNA nucleotide sequence was performed using a DNA nucleotide sequence optimized for CHO cells, which is an antibody-expressing cell line, and NheI and NotI restriction sites were inserted at both 5'- and 3' ends. The Kozak sequence (GCCACC) was inserted upstream of the start codon, ATG, for inducing the increase of expression level, and SEQ ID NO: 39 'MGWSCIILFLVATATGVHS' was inserted as a signal sequence for gene synthesis. The thus-synthesized gene was cleaved by treating with NheI and NotI.

Each of the cleaved DNAs was recovered by subjecting to 1% agarose gel electrophoresis, and the two DNAs were linked to construct a vector, which is the pCYBID vector inserted with the gene for tocilizumab light chain.

9-2. Insertion of a Gene for the Heavy Chain of Tocilizumab

The pCYBID-tocilizumab light chain gene vector constructed in Example 9-1 for the expression of light chain was cleaved with NheI and XhoI. The amino acid sequence (SEQ ID NO: 18) of tocilizumab was substituted with a DNA nucleotide sequence (SEQ ID NO: 16). Then, the vector was designed by inserting the Kozak sequence (GCCACC) upstream of the start codon, ATG, as in Example 9-1, and a gene was synthesized by inserting NheI and XhoI restriction sites at both ends, and cleaved by treating with NheI and XhoI. Each of the cleaved DNAs was recovered by subjecting to 1% agarose gel electrophoresis, and the two DNAs were linked to construct a vector, which is the pCYB vector inserted with the light chain and the heavy chain gene of tocilizumab (FIG. 8).

FIG. 8 is a schematic diagram illustrating the restriction map of the expression vector pCYBBSS001 of the present invention.

Example 10

Measurement of the Efficiency of Antibody Expression by pCYBBSS001 Vector 10-1. Transfection For the development of a cell line capable of stably expressing an antibody protein, first, DHFR-deficient CHO-DG44 cells (Dr. Chasin, Univ. Columbia. USA) were aliquoted into 6-well plates at a concentration of $8 \times 10^5$ cells the day before the transfection and cultured in a $CO_2$ incubator at 37° C. Upon confirmation of the cell growth to 70% to 80% confluency in the plates, the light chain/heavy chain expression vector pCYBBSS001 vector was transfected into the cells using lipofectamine LTX and PLUS reagent (Invitrogen Corporation). In particular, the transfection was performed using a medium, which contains 2.5 µg of the expression vector DNA and 10 µL of lipofectamine LTX in the Opti-MEM-1 (Invitrogen Corporation), and the CHO-DG44 cells transfected with the light chain/heavy chain expression vector pCYBBSS001 were selected therefrom.

10-2. Amplification of Antibody Gene

Gene amplification was performed by treating the CHO-DG44 cell line, which was transfected with the pCYBBSS001 in Example 10-1, with methotrexate (MTX). The expression level was measured by the method of increasing the concentration of MTX when the cell growth was recovered to normal. The MTX treatment was at the concentration of 50 nM, 200 nM, and 800 nM. As a result, the cell line transfected with the pCYBBSS001 vector showed the highest expression level when treated with 800 nM MTX. The expression level was measured via Octet titer assay, and Protein A Dip and Read biosensors (ForteBIO, Cat. No. 18-5010, Lot No. 120716) was equilibrated with 1×PBS for at least 10 minutes and reacted with the culture liquid. The regeneration/neutralization of the biosensor was performed for 3 cycles after the analysis of each sample, and the culture liquid was analyzed after diluting with 1×PBS to be analyzed within the standard range. The expression levels at the concentration of 800 nM MTX in the two pools were confirmed to be 50.8 µg/mL and 51.7 µg/mL, and the result indicates that the transfection of the expression vector inserted with an intron of the present invention enables a constitutive and high expression of a gene.

Example 11

Construction of a Plasmid for the Expression of Denosumab 11-1. Insertion of a Gene for the Light Chain of Denosumab The pCYBID vector constructed in Example 5 was inserted with the gene for the denosumab light chain to construct a plasmid for the expression of the denosumab light chain.

Specifically, the pCYBID vector was cleaved with XbaI and NotI.

Regarding the gene for the denosumab light chain, the amino acid sequence (SEQ ID NO: 21) of tocilizumab was substituted with a DNA nucleotide sequence (SEQ ID NO: 19). The substitution of the DNA nucleotide sequence was performed using a DNA nucleotide sequence optimized for CHO cells, which is an antibody-expressing cell line, and NheI and NotI restriction sites were inserted at both 5'- and 3'ends. The Kozak sequence (GCCACC) was inserted upstream of the start codon, ATG, for inducing the increase of expression level, and SEQ ID NO: 39 'MGWSCIILFLVATATGVHS' was inserted as a signal sequence for gene synthesis. The thus-synthesized gene was cleaved by treating with NheI and NotI.

Each of the cleaved DNAs was recovered by subjecting to 1% agarose gel electrophoresis, and the two DNAs were linked to construct a vector, which is the pCYBID vector inserted with the gene for denosumab light chain.

11-2. Insertion of a Gene for the Heavy Chain of Denosumab

The pCYBID-denosumab light chain gene vector constructed in Example 11-1 for the expression of light chain was cleaved with NheI and XhoI. The amino acid sequence of denosumab (SEQ ID NO: 22) was substituted with a DNA nucleotide sequence (SEQ ID NO: 20). Then, the vector was designed by inserting the Kozak sequence (GCCACC) upstream of the start codon, ATG, as in Example 11-1, and a gene was synthesized by inserting NheI and XhoI restriction sites at both ends, and cleaved by treating with NheI and XhoI. Each of the cleaved DNAs was recovered by subjecting to 1% agarose gel electrophoresis, and the two DNAs were linked to construct a vector, which is the pCYB vector inserted with the light chain and the heavy chain gene of denosumab (FIG. 9).

FIG. 9 is a schematic diagram illustrating the restriction map of the expression vector pCYBBSS002 of the present invention.

Example 12

Measurement of the Efficiency of Antibody Expression by pCYBBSS002 Vector 12-1. Transfection For the development of a cell line capable of stably expressing an antibody protein, first, DHFR-deficient CHO-DG44 cells (Dr. Chasin, Univ. Columbia. USA) were aliquoted into 6-well plates at a concentration of $8 \times 10^5$ cells the day before the transfection and cultured in a $CO_2$ incubator at 37° C. Upon confirmation of the cell growth to 70% to 80% confluency in the plates, the light chain/heavy chain expression vector pCYBBSS002 vector was transfected into the cells using lipofectamine LTX and PLUS reagent (Invitrogen Corporation). In particular, the transfection was performed using a medium, which contains 2.5 µg of the expression vector DNA and 10 µL of lipofectamine LTX in the Opti-MEM-1 (Invitrogen Corporation), and the CHO-DG44 cells transfected with the light chain/heavy chain expression vector pCYBBSS002 were selected therefrom.

12-2. Amplification of Antibody Gene

Gene amplification was performed by treating the CHO-DG44 cell line, which was transfected with the pCYBBSS002 in Example 12-1, with methotrexate (MTX). The expression level was measured by the method of increasing the concentration of MTX when the cell growth was recovered to normal. The MTX treatment was at the concentration of 50 nM, 200 nM, and 800 nM. As a result, the cell line transfected with the pCYBBSS002 vector showed the highest expression level when treated with 800 nM MTX. The expression level was measured via Octet titer assay, and Protein A Dip and Read biosensors (ForteBIO, Cat. No. 18-5010, Lot No. 120716) was equilibrated with 1×PBS for at least 10 minutes and reacted with the culture liquid. The regeneration/neutralization of the biosensor was performed for 3 cycles after the analysis of each sample, and the culture liquid was analyzed after diluting with 1×PBS to be analyzed within the standard range. The expression level at the concentration of 800 nM MTX was confirmed to be 81.4 µg/mL, and the result indicates that the transfection of the expression vector inserted with an intron of the present invention enables a constitutive and high expression of a gene.

Example 13

Construction of a Plasmid for the Expression of Belimumab 13-1. Insertion of a Gene for the Light Chain of Belimumab The pCYBID vector constructed in Example 5 was inserted with the gene for the belimumab light chain to construct a plasmid for the expression of the belimumab light chain.

Specifically, the pCYBID vector was cleaved with XbaI and NotI.

The gene for the belimumab light chain was substituted with a DNA nucleotide sequence (SEQ ID NO: 23) which encodes the amino acid sequence (SEQ ID NO: 25). The substitution of the DNA nucleotide sequence was performed using a DNA nucleotide sequence optimized for CHO cells, which is an antibody-expressing cell line, and NheI and NotI restriction sites were inserted at both 5'- and 3' ends. The Kozak sequence (GCCACC) was inserted upstream of the start codon, ATG, for inducing the increase of expression level, and SEQ ID NO: 39 'MGWSCIILFLVATATGVHS' was inserted as a signal sequence for gene synthesis. The thus-synthesized gene was cleaved by treating with NheI and NotI.

Each of the cleaved DNAs was recovered by subjecting to 1% agarose gel electrophoresis, and the two DNAs were linked to construct a vector, which is the pCYBID vector was inserted with the gene for belimumab light chain.

13-2. Insertion of a Gene for the Heavy Chain of Belimumab

The pCYBID-belimumab light chain gene vector constructed in Example 13-1 for the expression of light chain was cleaved with NheI and XhoI. The amino acid sequence of belimumab (SEQ ID NO: 26) was substituted with a DNA nucleotide sequence (SEQ ID NO: 24). Then, the vector was designed by inserting the Kozak sequence (GCCACC) upstream of the start codon, ATG, as in Example 13-1, and a gene was synthesized by inserting NheI and XhoI restriction sites at both ends, and cleaved by treating with NheI and XhoI. Each of the cleaved DNAs was recovered by subjecting to 1% agarose gel electrophoresis, and the two DNAs were linked to construct a vector, which is the pCYB vector inserted with the light chain and the heavy chain gene of belimumab, respectively (FIG. 10).

FIG. 10 is a schematic diagram illustrating the restriction map of the expression vector pCYBBSS003 of the present invention.

Example 14

Measurement of the Efficiency of Antibody Expression by pCYBBSS003 Vector 14-1. Transfection For the development of a cell line capable of stably expressing an antibody protein, first, DHFR-deficient CHO-DG44 cells (Dr. Chasin, Univ. Columbia. USA) were aliquoted into 6-well plates at a concentration of $8 \times 10^5$ cells the day before the transfection and cultured in a $CO_2$ incubator at 37° C. Upon confirmation of the cell growth to 70% to 80% confluency in the plates, the light chain/heavy chain expression vector pCYBBSS003 vector was transfected into the cells using lipofectamine LTX and PLUS reagent (Invitrogen Corporation). In particular, the transfection was performed using a medium, which contains 2.5 µg of the expression vector DNA and 10 µL of lipofectamine LTX in the Opti-MEM-1 (Invitrogen Corporation), and the CHO-DG44 cells transfected with the light chain/heavy chain expression vector pCYBBSS003 were selected therefrom.

14-2. Measurement of Expression Level of Antibody Gene

The expression level of belimumab in the CHO-DG44 cell line, which was transfected with the pCYBBSS003 in Example 14-1, was measured. The expression level was measured via ELISA using anti-Fc, and the expression level/cell was obtained by the calculation of picograms/cell/day (PCD). As a result, the cell line transfected with the pCYBBSS003 vector showed an expression level of 4 µg/mL, and the result indicates that the transfection of the expression vector inserted with an intron of the present invention enables a constitutive and high expression of a gene.

Example 15

Construction of a Plasmid for the Expression of Golimumab 15-1. Insertion of a Gene for the Light Chain of Golimumab The pCYBID vector constructed in Example 5 was inserted with the gene for the golimumab light chain to construct a plasmid for the expression of the golimumab light chain.

Specifically, the pCYBID vector was cleaved with XbaI and NotI.

The gene for the golimumab light chain was substituted with a DNA nucleotide sequence (SEQ ID NO: 27) which encodes the amino acid sequence (SEQ ID NO: 29) of golimumab. The substitution of the DNA nucleotide sequence was performed using a DNA nucleotide sequence optimized for CHO cells, which is an antibody-expressing cell line, and NheI and NotI restriction sites were inserted at both 5'- and 3' ends. The Kozak sequence (GCCACC) was inserted upstream of the start codon, ATG, for inducing the increase of expression level, and SEQ ID NO: 39 'MGWSCIILFLVATATGVHS' was inserted as a signal sequence for gene synthesis. The thus-synthesized gene was cleaved by treating with NheI and NotI.

Each of the cleaved DNAs was recovered by subjecting to 1% agarose gel electrophoresis, and the two DNAs were linked to construct a vector, which is the pCYBID vector inserted with the gene for golimumab light chain.

15-2. Insertion of a Gene for the Heavy Chain of Golimumab

The pCYBID-golimumab light chain gene vector constructed in Example 15-1 for the expression of light chain was cleaved with NheI and XhoI. The amino acid sequence of golimumab (SEQ ID NO: 30) was substituted with a DNA nucleotide sequence (SEQ ID NO: 28). Then, the vector was designed by inserting the Kozak sequence (GCCACC) upstream of the start codon, ATG, as in Example 15-1, and a gene was synthesized by inserting NheI and XhoI restriction sites at both ends, and cleaved by treating with NheI and XhoI. Each of the cleaved DNAs was recovered by subjecting to 1% agarose gel electrophoresis, and the two DNAs were linked to construct a vector, which is the pCYB vector inserted with the light chain and the heavy chain gene of golimumab (FIG. 11).

FIG. 11 is a schematic diagram illustrating the restriction map of the expression vector pCYBBSS004 of the present invention.

Example 16

Measurement of the Efficiency of Antibody Expression by pCYBBSS004 Vector 16-1. Transfection For the development of a cell line capable of stably expressing an antibody protein, first, DHFR-deficient CHO-DG44 cells (Dr. Chasin, Univ. Columbia. USA) were aliquoted into 6-well plates at a concentration of $8 \times 10^5$ cells the day before the transfection and cultured in a $CO_2$ incubator at 37° C. Upon confirmation of the cell growth to 70% to 80% confluency in the plates, the light chain/heavy chain expression vector pCYBBSS004 vector was transfected into the cells using lipofectamine LTX and PLUS reagent (Invitrogen Corporation). In particular, the transfection was performed using a medium, which contains 2.5 μg of the expression vector DNA and 10 μL of lipofectamine LTX in the Opti-MEM-1 (Invitrogen Corporation), and the CHO-DG44 cells transfected with the light chain/heavy chain expression vector pCYBBSS004 were selected therefrom.

16-2. Amplification of Antibody Gene

Gene amplification was performed by treating the CHO-DG44 cell line, which was transfected with the pCYBBSS004 in Example 16-1, with methotrexate (MTX). The expression level was measured by the method of increasing the concentration of MTX when the cell growth was recovered to normal. The MTX treatment was at the concentration of 50 nM, 200 nM, 500 nM, and 800 nM. As a result, the cell line transfected with the pCYBBSS004 vector showed the highest expression level when treated with 800 nM MTX. The expression level was measured via Octet titer assay, and Protein A Dip and Read biosensors (ForteBIO, Cat. No. 18-5010, Lot No. 120716) was equilibrated with 1×PBS for at least 10 minutes and reacted with the culture liquid. The regeneration/neutralization of the biosensor was performed for 3 cycles after the analysis of each sample, and the culture liquid was analyzed after diluting with 1×PBS to be analyzed within the standard range. The expression level at the concentration of 500 nM MTX was confirmed to be 120.3 μg/mL, and the result indicates that the transfection of the golimumab-expressing vector of the present invention enables a constitutive and high expression of a gene.

Example 17

Construction of a Plasmid for the Expression of Ustekinumab 17-1. Insertion of a Gene for the Light Chain of Ustekinumab The pCYBID vector constructed in Example 5 was inserted with the gene for the ustekinumab light chain to construct a plasmid for the expression of the ustekinumab light chain.

Specifically, the pCYBID vector was cleaved with XbaI and NotI.

The gene for the ustekinumab light chain was substituted with a DNA nucleotide sequence (SEQ ID NO: 31) which encodes the amino acid sequence (SEQ ID NO: 33) of ustekinumab. The substitution of the DNA nucleotide sequence was performed using a DNA nucleotide sequence optimized for CHO cells, which is an antibody-expressing cell line, and NheI and NotI restriction sites were inserted at both 5'- and 3' ends. The Kozak sequence (GCCACC) was inserted upstream of the start codon, ATG, for inducing the increase of expression level, and SEQ ID NO: 39 'MGWSCIILFLVATATGVHS' was inserted as a signal sequence for gene synthesis. The thus-synthesized gene was cleaved by treating with NheI and NotI.

Each of the cleaved DNAs was recovered by subjecting to 1% agarose gel electrophoresis, and the two DNAs were linked to construct a vector, which is the pCYBID vector inserted with the gene for ustekinumab light chain.

17-2. Insertion of a Gene for the Heavy Chain of Ustekinumab

The pCYBID-ustekinumab light chain gene vector constructed in Example 17-1 for the expression of light chain was cleaved with NheI and XhoI. The amino acid sequence of ustekinumab (SEQ ID NO: 34) was substituted with a DNA nucleotide sequence (SEQ ID NO: 32). Then, the vector was designed by inserting the Kozak sequence (GCCACC) upstream of the start codon, ATG, as in Example 17-1, and a gene was synthesized by inserting NheI and XhoI restriction sites at both ends, and cleaved by treating with NheI and XhoI. Each of the cleaved DNAs was recovered by subjecting to 1% agarose gel electrophoresis, and the two DNAs were linked to construct a vector, which is the pCYB vector inserted with the light chain and the heavy chain gene of ustekinumab (FIG. 12).

FIG. 12 is a schematic diagram illustrating the restriction map of the expression vector pCYBBSS005 of the present invention.

Example 18

Measurement of the Efficiency of Antibody Expression by pCYBBSS005 Vector 18-1. Transfection For the development of a cell line capable of stably expressing an antibody protein, first, DHFR-deficient CHO-DG44 cells (Dr. Chasin, Univ. Columbia. USA) were aliquoted into 6-well plates at a concentration of $8 \times 10^5$ cells the day before the transfection and cultured in a $CO_2$ incubator at 37° C. Upon confirmation of the cell growth to 70% to 80% confluency in the plates, the light chain/heavy chain expression vector pCYBBSS005 vector was transfected into the cells using lipofectamine LTX and PLUS reagent (Invitrogen Corporation). In particular, the transfection was performed using a medium, which contains 2.5 μg of the expression vector DNA and 10 μL of lipofectamine LTX in the Opti-MEM-1 (Invitrogen Corporation), and the CHO-DG44 cells transfected with the light chain/heavy chain expression vector pCYBBSS005 were selected therefrom.

18-2. Measurement of Expression Level of Antibody Gene

The expression level of ustekinumab in the CHO-DG44 cell line, which was transfected with the pCYBBSS005 in Example 18-1, was measured. The expression level was measured via ELISA using anti-Fc, and the expression level/cell was obtained by the calculation of picograms/cell/day (PCD). As a result, the cell line transfected with the pCYBBSS005 vector showed an expression level of 2.5 μg/mL, and the result indicates that the transfection of the expression vector inserted with an intron of the present invention enables a constitutive and high expression of a gene.

Example 19

Construction of a Plasmid for the Expression of Ipilimumab 19-1. Insertion of a Gene for the Light Chain of Ipilimumab The pCYBID vector constructed in Example 5 was inserted with the gene for the ipilimumab light chain to construct a plasmid for the expression of the ipilimumab light chain.

Specifically, the pCYBID vector was cleaved with XbaI and NotI.

The gene for the ipilimumab light chain was substituted with a DNA nucleotide sequence (SEQ ID NO: 37) which encodes the amino acid sequence (SEQ ID NO: 35) of ipilimumab. The substitution of the DNA nucleotide sequence was performed using a DNA nucleotide sequence optimized for CHO cells, which is an antibody-expressing cell line, and NheI and NotI restriction sites were inserted at both 5'- and 3' ends. The Kozak sequence (GCCACC) was inserted upstream of the start codon, ATG, for inducing the increase of expression level, and SEQ ID NO: 39 'MGWSCIILFLVATATGVHS' was inserted as a signal sequence for gene synthesis. The thus-synthesized gene was cleaved by treating with NheI and NotI.

Each of the cleaved DNAs was recovered by subjecting to 1% agarose gel electrophoresis, and the two DNAs were linked to construct a vector, which is the pCYBID vector inserted with the gene for ipilimumab light chain.

19-2. Insertion of a Gene for the Heavy Chain of Ipilimumab

The pCYBID-ipilimumab light chain gene vector constructed in Example 19-1 for the expression of light chain was cleaved with NheI and XhoI. The amino acid sequence of ipilimumab (SEQ ID NO: 38) was substituted with a DNA nucleotide sequence (SEQ ID NO: 36). Then, the vector was designed by inserting the Kozak sequence (GCCACC) upstream of the start codon, ATG, as in Example 19-1, and a gene was synthesized by inserting NheI and XhoI restriction sites at both ends, and cleaved by treating with NheI and XhoI. Each of the cleaved DNAs was recovered by subjecting to 1% agarose gel electrophoresis, and the two DNAs were linked to construct a vector, which is the pCYB vector inserted with the light chain and the heavy chain gene of ustekinumab (FIG. 13).

FIG. 13 is a schematic diagram illustrating the restriction map of the expression vector pCYBBSS006 of the present invention.

Example 20

Measurement of the Efficiency of Antibody Expression by pCYBBSS006 Vector 20-1. Transfection For the development of a cell line capable of stably expressing an antibody protein, first, DHFR-deficient CHO-DG44 cells (Dr. Chasin, Univ. Columbia. USA) were aliquoted into 6-well plates at a concentration of $8 \times 10^5$ cells the day before the transfection and cultured in a $CO_2$ incubator at 37° C. Upon confirmation of the cell growth to 70% to 80% confluency in the plates, the light chain/heavy chain expression vector pCYBBSS005 vector was transfected into the cells using lipofectamine LTX and PLUS reagent (Invitrogen Corporation). In particular, the transfection was performed using a medium, which contains 2.5 μg of the expression vector DNA and 10 μL of lipofectamine LTX in the Opti-MEM-1 (Invitrogen Corporation), and the CHO-DG44 cells transfected with the light chain/heavy chain expression vector pCYBBSS006 were selected therefrom.

20-2. Amplification of Antibody Gene

Gene amplification was performed by treating the CHO-DG44 cell line, which was transfected with the pCYBBSS006 in Example 20-1, with methotrexate (MTX). The expression level was measured by the method of increasing the concentration of MTX when the cell growth was recovered to normal. The MTX treatment was at the concentration of 50 nM, 200 nM, 500 nM, and 800 nM. As a result, the cell line transfected with the pCYBBSS006 vector showed the highest expression level when treated with 500 nM MTX. The expression level was measured via Octet titer assay, and Protein A Dip and Read biosensors (ForteBIO, Cat. No. 18-5010, Lot No. 120716) was equilibrated with 1×PBS for at least 10 minutes and reacted with the culture liquid. The regeneration/neutralization of the biosensor was performed for 3 cycles after the analysis of each sample, and the culture liquid was analyzed after diluting with 1×PBS to be analyzed within the standard range. The expression level at the concentration of 500 nM MTX was confirmed to be 8 µg/mL, and the result indicates that the transfection of the expression vector inserted with an intron of the present invention enables a constitutive and high expression of a gene.

Those of ordinary skill in the art will recognize that the present invention may be embodied in other specific forms without departing from its spirit or essential characteristics. The described embodiments are to be considered in all respects only as illustrative and not restrictive. The scope of the present invention is, therefore, indicated by the appended claims rather than by the foregoing description. All changes which come within the meaning and range of equivalency of the claims are to be embraced within the scope of the present invention.

What is claimed is:

1. An expression vector for antibody expression, comprising:
   (i) a first monocistronic expression cassette consisting of, in sequential order, a cytomegalovirus (CMV) promoter, a CMV untranslated region (UTR), a CMV intron, an antibody light chain gene, and a polyA sequence; wherein the CMV promoter consists of the nucleotide sequence of SEQ ID NO: 1, the UTR consists of the nucleotide sequence of SEQ ID NO: 2 and the intron consists of the nucleotide sequence of SEQ ID NO: 3; and
   (ii) a second polycistronic expression cassette consisting of, in sequential order, a promoter, a UTR, an intron, an antibody heavy chain gene, an internal ribosome entry site (IRES), dihydrofolate reductase (DHFR), and a polyA sequence; wherein the promoter is a CMV promoter consisting of the nucleotide sequence of SEQ ID NO: 1, the UTR consists of the nucleotide sequence of SEQ ID NO: 2 and the intron consists of the nucleotide sequence of SEQ ID NO: 3.

2. The expression vector of claim 1, wherein the antibody is bevacizumab, tocilizumab, denosumab, belimumab, golimumab, ustekinumab, or ipilimumab.

3. The expression vector of claim 1, wherein the expression vector comprises a cleavage map selected from the group consisting of pCYB204IG, pCYB204ID, pCYBBSS001 pCYBBSS002, pCYBBSS003 pCYBBSS004, pCYBBSS005, pCYBBSS006.

4. The expression vector of claim 1, wherein the antibody light chain gene consists of a nucleotide sequence selected from the group consisting of SEQ ID NO: 11, SEQ ID NO: 15, SEQ ID NO: 19, SEQ ID NO: 23, SEQ ID NO: 27, SEQ ID NO: 31, and SEQ ID NO: 35.

5. The expression vector of claim 1, wherein the antibody heavy chain gene consists of a nucleotide sequence selected from the group consisting of SEQ ID NO: 12, SEQ ID NO: 16, SEQ ID NO: 20, SEQ ID NO: 24, SEQ ID NO: 28, SEQ ID NO: 32, and SEQ ID NO: 36.

6. An isolated animal cell transfected with the expression vector according to claim 1.

7. The isolated animal cell of claim 6, wherein the isolated animal cell is a Chinese hamster ovary (CHO) cell.

8. A method of producing an antibody comprising culturing the isolated animal cell according to claim 6.

9. The method of claim 8, further comprising purifying the antibody in the culture product in which the isolated animal cell was cultured.

10. The method of claim 8, wherein the antibody is bevacizumab, tocilizumab, denosumab, belimumab, golimumab, ustekinumab, or ipilimumab.

* * * * *